US012559576B2

(12) United States Patent
Shen et al.

(10) Patent No.: US 12,559,576 B2
(45) Date of Patent: *Feb. 24, 2026

(54) CD20-PD1 BINDING MOLECULES AND METHODS OF USE THEREOF

(71) Applicant: Regeneron Pharmaceuticals, Inc., Tarrytown, NY (US)

(72) Inventors: Yang Shen, Scarsdale, NY (US); Bei Wang, Hastings-on-Hudson, NY (US); Naga Suhasini Avvaru, Briarcliff Manor, NY (US); Chia-Yang Lin, Scarsdale, NY (US); Andrew Murphy, Croton-on-Hudson, NY (US); Aynur Hermann, New York, NY (US); Jee H. Kim, Ardsley, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 310 days.

This patent is subject to a terminal disclaimer.

(21) Appl. No.: 18/053,868

(22) Filed: Nov. 9, 2022

(65) Prior Publication Data

US 2023/0279153 A1    Sep. 7, 2023

Related U.S. Application Data

(60) Provisional application No. 63/278,454, filed on Nov. 11, 2021, provisional application No. 63/278,374, filed on Nov. 11, 2021.

(51) Int. Cl.
| | |
|---|---|
| *C07K 16/46* | (2006.01) |
| *A61K 39/00* | (2006.01) |
| *A61P 3/10* | (2006.01) |
| *A61P 37/06* | (2006.01) |
| *C07K 16/28* | (2006.01) |
| *G01N 33/68* | (2006.01) |

(52) U.S. Cl.
CPC .............. *C07K 16/468* (2013.01); *A61P 3/10* (2018.01); *A61P 37/06* (2018.01); *C07K 16/2818* (2013.01); *C07K 16/2887* (2013.01); *G01N 33/6845* (2013.01); *A61K 2039/505* (2013.01); *C07K 2317/31* (2013.01); *C07K 2317/52* (2013.01); *C07K 2317/55* (2013.01); *C07K 2317/622* (2013.01)

(58) Field of Classification Search
CPC .... C07K 16/468; C07K 16/2887; A61P 37/06
See application file for complete search history.

(56) References Cited

U.S. PATENT DOCUMENTS

| | | | |
|---|---|---|---|
| 9,987,500 B2 | 6/2018 | Papadopoulos et al. | |
| 2007/0136826 A1* | 6/2007 | Dunn ................ | C07K 16/2887 536/23.53 |
| 2017/0174781 A1 | 6/2017 | Brownstein | |

| | | | |
|---|---|---|---|
| 2019/0202935 A1* | 7/2019 | Chou ..................... | C07K 16/30 |
| 2020/0172627 A1 | 6/2020 | Bacac et al. | |
| 2021/0008113 A1 | 1/2021 | Zhu et al. | |

FOREIGN PATENT DOCUMENTS

| | | | | |
|---|---|---|---|---|
| CN | 107043425 B | 5/2019 | | |
| CN | 109954138 A | 7/2019 | | |
| EP | 1576014 B1 | 6/2011 | | |
| EP | 3693013 A1 | 8/2020 | | |
| WO | WO2002079474 A2 | 10/2002 | | |
| WO | WO-2011109789 A2 * | 9/2011 | .......... | A61K 31/704 |
| WO | WO2013164694 A1 | 11/2013 | | |
| WO | WO2015095410 A1 | 6/2015 | | |
| WO | WO2017112775 A1 | 6/2017 | | |
| WO | WO2017134592 A1 | 8/2017 | | |
| WO | WO2018058111 A1 | 3/2018 | | |
| WO | WO-2018170021 A1 * | 9/2018 | ............. | A61P 37/02 |
| WO | WO-2018200422 A1 * | 11/2018 | ............. | C07K 16/40 |
| WO | WO2018223004 A1 | 12/2018 | | |
| WO | WO2019219709 A1 | 11/2019 | | |
| WO | WO2021062184 A1 | 4/2021 | | |
| WO | WO2021243028 A1 | 12/2021 | | |
| WO | WO2023086812 A1 | 5/2023 | | |

OTHER PUBLICATIONS

Klein, Christian, et al. "Epitope interactions of monoclonal antibodies targeting CD20 and their relationship to functional properties." MAbs. vol. 5. No. 1. Taylor & Francis, 2013. (Year: 2013).*
Lim, Hocheol, et al. "Investigation of protein-protein interactions and hot spot region between PD-1 and PD-L1 by fragment molecular orbital method." Scientific reports 9.1 (2019): 16727. (Year: 2019).*
Magiera-Mularz, Katarzyna, et al. "Human and mouse PD-L1: similar molecular structure, but different druggability profiles." Iscience 24.1 (2021). (Year: 2021).*
PDB: 2OSL_A; Deposited Apr. 10, 2007; Retrieved Dec. 10, 2024; https://www.ncbi.nlm.nih.gov/protein/146387641 (Year: 2007).*
PDB: 2OSL_B; Deposited Apr. 10, 2007; Retrieved Dec. 10, 2024; https://www.ncbi.nlm.nih.gov/protein/146387640 (Year: 2007).*
NCBI Reference Sequence: NP_068693.1; Deposited Nov. 20, 2000; Retrieved Dec. 10, 2024; https://www.ncbi.nlm.nih.gov/protein/11230798 (Year: 2000).*
Brinkmann, Ulrich, and Roland E. Kontermann. "The making of bispecific antibodies." MAbs. vol. 9. No. 2. Taylor & Francis, 2017. (Year: 2017).*
Curnock, Adam P., et al. "Cell-targeted PD-1 agonists that mimic PD-L1 are potent T cell inhibitors." JCI insight 6.20 (2021).

(Continued)

*Primary Examiner* — Julie Wu
*Assistant Examiner* — Bryan William Heck
(74) *Attorney, Agent, or Firm* — Biospark Intellectual Property Law

(57) ABSTRACT

The present disclosure relates to molecules capable of binding to both CD20 and PD1, as well as pharmaceutical compositions comprising such molecules and methods of use thereof.

20 Claims, 23 Drawing Sheets

Specification includes a Sequence Listing.

(56) References Cited

OTHER PUBLICATIONS

Grebinoski, Stephanie, and Dario AA Vignali. "Inhibitory receptor agonists: the future of autoimmune disease therapeutics ?. " Current opinion in immunology 67 (2020): 1-9.

International Search Report and Written Opinion for PCT/US2022/079530, mailed Feb. 17, 2023.

Grebinoski et al., 2020, "Inhibitory receptor agonists: the future of autoimmune disease therapeutics?," Current Opinion in Immunology, (67): 1-9.

Zhang et al., 2023, "B cell depletion therapies in autoimmune diseases: Monoclonal antibodies or chimeric antigen receptor-based therapy?," Frontiers in Immunology, 14:1126421, 1-9.

International Search Report and Written Opinion mailed Sep. 18, 2024 in connection with PCT application No. PCT/US2024/028852.

Liang, et al. 2017. "High-affinity human PD-L1 variants attenuate the suppression of T cell activation." Oncotarget 8.51: 88360-88375.

Zak, et al. 2015. "Structure of the complex of human programmed death 1, PD-1, and its ligand PD-L1." Structure 23.12: 2341-2348.

\* cited by examiner

CD20:PD1 Ratio
1:1

CD20:PD1 Ratio
1:1

CD20:PD1 Ratio
1:1

CD20:PD1 Ratio
1:1

CD20:PD1 Ratio
2:1

CD20:PD1 Ratio
2:1

CD20:PD1 Ratio
2:2

CD20:PD1 Ratio
1:2

CD20:PD1 Ratio
2:1

CD20:PD1 Ratio
2:2

CD20:PD1 Ratio
2:2

CD20:PD1 Ratio
2:2

Modeled mPDL1 IgV / mPD1 complex

An unpaired Cysteine (C113) at the surface of mPDL1 mPDLi_78_137    78  SNFRGRASLPKDQLLKGNAALQITDVKLQDAGVYCCLISYGGADYKRITLKVNAPYRKIN 137
hPDLi_78_137    78  SSYRQRARLLKDQLSLGNAALQITDVKLQDAGVYRCMISYGGADYKRITVKVNAPYNKIN 137
                    *   *  .  * ***  ******************* .* ****** ** *

HEK293/CD22/mCD20

10k HEK293/CD22/mCD20 + 30k Jurkat/AP1-Luc/mPD-1 (2.5nM CD22 x CD3 bispecific)

10k HEK293/CD22 mCD20 + 30k Jurkat/AP1-Luc/mPD-1 (2.5nM CD22 x CD3 bispecific)

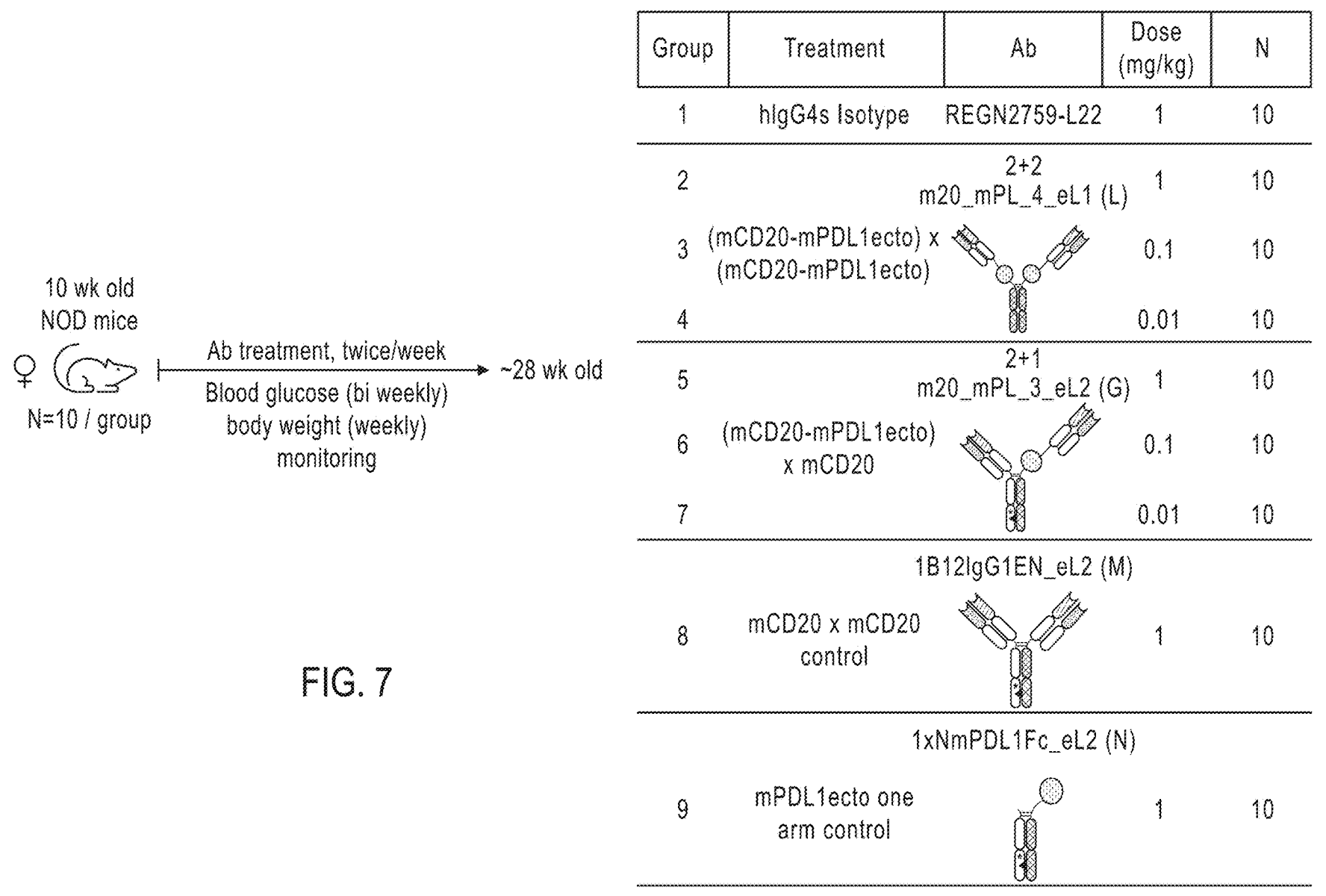

| Group | Treatment | Ab | Dose (mg/kg) | N |
|---|---|---|---|---|
| 1 | hIgG4s Isotype | REGN2759-L22 | 1 | 10 |
| 2 | (mCD20-mPDL1ecto) x (mCD20-mPDL1ecto) | 2+2 m20_mPL_4_eL1 (L) | 1 | 10 |
| 3 | | | 0.1 | 10 |
| 4 | | | 0.01 | 10 |
| 5 | (mCD20-mPDL1ecto) x mCD20 | 2+1 m20_mPL_3_eL2 (G) | 1 | 10 |
| 6 | | | 0.1 | 10 |
| 7 | | | 0.01 | 10 |
| 8 | mCD20 x mCD20 control | 1B12IgG1EN_eL2 (M) | 1 | 10 |
| 9 | mPDL1ecto one arm control | 1xNmPDL1Fc_eL2 (N) | 1 | 10 |

10 wk old NOD mice

♀

N=10 / group

Ab treatment, twice/week

~28 wk old

Blood glucose (bi weekly) body weight (weekly) monitoring

FIG. 7

Control

2 + 2 (L)

1 mg/kg

2 + 1 (G)

1 mg/kg

Control

BG_mPDL1ecto one arm control 1 mg/kg 0.1 mg/kg
BG_mPDL1ecto x mCD20 (2+2) 0.1 mg/kg

2 + 2 (L)

2 + 1 (G)

BG_(mCD20-mPDL1ecto) x mCD20 0.1 mg/kg

Control

BG_mCD20 x mCD20 1 mg/kg

2 + 2 (L)

0.01 mg/kg

BG_mPDL1ecto x mCD20 (2+2) 0.01 mg/kg

2 + 1 (G)

BG_(mCD20-mPDL1ecto) x mCD20 0.01 mg/kg

Less Activated (LA) Cluster

- Isotype
- anti-mCD20 IgG (1 mg/kg)
- mPDL1ecto-Fc (1 mg/kg)
- mCD20 x mPDL1ecto (2+2) (0.1 mg/kg)
- mCD20 x mPDL1ecto (2+2) (1 mg/kg)

Proliferating/Activated (PA) Cluster

- Isotype
- anti-mCD20 IgG (1 mg/kg)
- mPDL1ecto-Fc (1 mg/kg)
- mCD20 x mPDL1ecto (2+2) (0.1 mg/kg)
- mCD20 x mPDL1ecto (2+2) (1 mg/kg)

LA/PA Ratio in Pancreas

● Isotype
▲ anti-mCD20 IgG (1 mg/kg)
▼ mPDL1ecto-Fc (1 mg/kg)
◇ mCD20 x mPDL1ecto (2+2) (0.1 mg/kg)
◆ mCD20 x mPDL1ecto (2+2) (1 mg/kg)

Total CD3+ T cell count

Total CD4+ T cell count

FIG. 11C

SEQUENCE LISTING

```
Sequence total quantity: 56
SEQ ID NO: 1             moltype = AA  length = 15
FEATURE                  Location/Qualifiers
source                   1..15
                         mol_type = protein
                         organism = synthetic construct
SEQUENCE: 1
GGGGSGGGGS GGGGS                                                15

SEQ ID NO: 2             moltype = AA  length = 290
FEATURE                  Location/Qualifiers
source                   1..290
                         mol_type = protein
                         organism = Homo sapiens
SEQUENCE: 2
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPELP LAHPPNERTH  240
LVILGAILLC LGVALTFIFR LRKGRMMDVK KCGIQDTNSK KQSDTHLEET            290

SEQ ID NO: 3             moltype = AA  length = 290
FEATURE                  Location/Qualifiers
source                   1..290
                         mol_type = protein
                         organism = Mus musculus
SEQUENCE: 3
MRIFAGIIFT ACCHLLRAFT ITAPKDLYVV EYGSNVTMEC RFPVERELDL LALVVYWEKE  60
DEQVIQFVAG EEDLKPQHSN FRGRASLPKD QLLKGNAALQ ITDVKLQDAG VYCCIISYGG  120
ADYKRITLKV NAPYRKINQR ISVDPATSEH ELICQAEGYP EAEVIWTNSD HQPVSGKRSV  180
TTSRTEGMLL NVTSSLRVNA TANDVFYCTF WRSQPGQNHT AELIIPELPA THPPQNRTHW  240
VLLGSILLFL IVVSTVLLFL RKQVRMLDVE KCGVEDTSSK NRNDTQFEET            290

SEQ ID NO: 4             moltype = AA  length = 273
FEATURE                  Location/Qualifiers
source                   1..273
                         mol_type = protein
                         organism = Homo sapiens
SEQUENCE: 4
MIFLLLMLSL ELQLHQIAAL FTVTVPKELY IIEHGSNVTL ECNFDTGSHV NLGAITASLQ  60
KVENDTSPHR ERATLLEEQL PLGKASFHIP QVQVRDEGQY QCIIIYGVAW DYKYLTLKVK  120
ASYRKINTHI LKVPETDEVE LTCQATGYPL AEVSWPNVSV PANTSHSRTP EGLYQVTSVL  180
RLKPPPGRNF SCVFWNTHVR ELTLASIDLQ SQMEPRTHPT WLLHIFIPFC IIAFIFIATV  240
IALRKQLCQK LYSSKDTTKR PVTTTKREVN SAI                             273

SEQ ID NO: 5             moltype = AA  length = 247
```

-continued

```
FEATURE                Location/Qualifiers
source                 1..247
                       mol_type = protein
                       organism = Mus musculus
SEQUENCE: 5
MLLLLPILNL SLQLHPVAAL FTVTAPKEVY TVDVGSSVSL ECDFDRRECT ELEGIRASLQ   60
KVENDTSLQS ERATLLEEQL PLGKALFHIP SVQVRDSGQY RCLVICGAAW DYKYLTVKVK  120
ASYMRIDTRI LEVPGTGEVQ LTCQARGYPL AEVSWQNVSV PANTSHIRTP EGLYQVTSVL  180
RLKPQPSRNF SCMFWNAHMK ELTSAIIDPL SRMEPKVPRT WPLHVFIPAC TIALIFLAIV  240
IIQRKRI                                                            247

SEQ ID NO: 6           moltype = AA   length = 231
FEATURE                Location/Qualifiers
source                 1..231
                       mol_type = protein
                       organism = synthetic construct
SEQUENCE: 6
DKRVESKYGP CPPCPAPPVA GPSVFLFPPK PKDTLMISRT PEVTCVVVDV SQEDPEVQFN   60
WYVDGVEVHN AKTKPREEQF NSTYRVVSVL TVLHQDWLNG KEYKCKVSNK GLPSSIEKTI  120
SKAKGQPREP QVYTLPPSQE EMTKNQVSLT CLVKGFYPSD IAVEWESNGQ PENNYKTTPP  180
VLDSDGSFFL YSRLTVDKSR WQEGNVFSCS VMHEALHNHY TQKSLSLSLG K           231

SEQ ID NO: 7           moltype = AA   length = 235
FEATURE                Location/Qualifiers
source                 1..235
                       mol_type = protein
                       organism = synthetic construct
SEQUENCE: 7
DKKVEPKSCD KTHTCPPCPA PPVAGPSVFL FPPKPKDTLM ISRTPEVTCV VVDVSQEDPE   60
VQFNWYVDGV EVHNAKTKPR EEQFNSTYRV VSVLTVLHQD WLNGKEYKCK VSNKGLPSSI  120
EKTISKAKGQ PREPQVYTLP PSRDELTKNQ VSLTCLVKGF YPSDIAVEWE SNGQPENNYK  180
TTPPVLDSDG SFFLYSKLTV DKSRWQQGNV FSCSVMHEAL HNHYTQKSLS LSPGK       235

SEQ ID NO: 8           moltype = AA   length = 329
FEATURE                Location/Qualifiers
source                 1..329
                       mol_type = protein
                       organism = synthetic construct
SEQUENCE: 8
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPPVAGP  120
SVFLFPPKPK DTLMISRTPE VTCVVVDVSQ EDPEVQFNWY VDGVEVHNAK TKPREEQFNS  180
TYRVVSVLTV LHQDWLNGKE YKCKVSNKGL PSSIEKTISK AKGQPREPQV YTLPPSRDEL  240
TKNQVSLTCL VKGFYPSDIA VEWESNGQPE NNYKTTPPVL DSDGSFFLYS KLTVDKSRWQ  300
QGNVFSCSVM HEALHNHYTQ KSLSLSPGK                                    329

SEQ ID NO: 9           moltype = AA   length = 326
FEATURE                Location/Qualifiers
source                 1..326
                       mol_type = protein
                       organism = synthetic construct
SEQUENCE: 9
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APPVAGPSVF  120
LFPPKPKDTL MISRTPEVTC VVVDVSQEDP EVQFNWYVDG VEVHNAKTKP REEQFNSTYR  180
VVSVLTVLHQ DWLNGKEYKC KVSNKGLPSS IEKTISKAKG QPREPQVYTL PPSQEEMTKN  240
QVSLTCLVKG FYPSDIAVEW ESNGQPENNY KTTPPVLDSD GSFFLYSRLT VDKSRWQEGN  300
VFSCSVMHEA LHNHYTQKSL SLSLGK                                       326

SEQ ID NO: 10          moltype = AA   length = 329
FEATURE                Location/Qualifiers
source                 1..329
                       mol_type = protein
                       organism = synthetic construct
SEQUENCE: 10
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPPVAGP  120
SVFLFPPKPK DTLMISRTPE VTCVVVDVSQ EDPEVQFNWY VDGVEVHNAK TKPREEQFNS  180
TYRVVSVLTV LHQDWLNGKE YKCKVSNKGL PSSIEKTISK AKGQPREPQV YTLPPSRDEL  240
TKNQVSLTCL VKGFYPSDIA VEWESNGQPE NNYKTTPPVL DSDGSFFLYS KLTVDKSRWQ  300
QGNVFSCSVM HEALHNRFTQ KSLSLSPGK                                    329

SEQ ID NO: 11          moltype = AA   length = 326
FEATURE                Location/Qualifiers
source                 1..326
                       mol_type = protein
                       organism = synthetic construct
SEQUENCE: 11
ASTKGPSVFP LAPCSRSTSE STAALGCLVK DYFPEPVTVS WNSGALTSGV HTFPAVLQSS   60
```

```
GLYSLSSVVT VPSSSLGTKT YTCNVDHKPS NTKVDKRVES KYGPPCPPCP APPVAGPSVF   120
LFPPKPKDTL MISRTPEVTC VVVDVSQEDP EVQFNWYVDG VEVHNAKTKP REEQFNSTYR   180
VVSVLTVLHQ DWLNGKEYKC KVSNKGLPSS IEKTISKAKG QPREPQVYTL PPSQEEMTKN   240
QVSLTCLVKG FYPSDIAVEW ESNGQPENNY KTTPPVLDSD GSFFLYSRLT VDKSRWQEGN   300
VFSCSVMHEA LHNRFTQKSL SLSLGK                                        326

SEQ ID NO: 12              moltype = AA   length = 11
FEATURE                    Location/Qualifiers
source                     1..11
                           mol_type = protein
                           organism = synthetic construct
VARIANT                    1..10
                           note = This region may encompass 1-10 repeating residues
SEQUENCE: 12
GGGGGGGGGG S                                                         11

SEQ ID NO: 13              moltype = AA   length = 11
FEATURE                    Location/Qualifiers
source                     1..11
                           mol_type = protein
                           organism = synthetic construct
VARIANT                    2..11
                           note = This region may encompass 1-10 repeating residues
SEQUENCE: 13
SGGGGGGGGG G                                                         11

SEQ ID NO: 14              moltype = AA   length = 5
FEATURE                    Location/Qualifiers
source                     1..5
                           mol_type = protein
                           organism = synthetic construct
SEQUENCE: 14
GGGGS                                                                5

SEQ ID NO: 15              moltype = AA   length = 4
FEATURE                    Location/Qualifiers
source                     1..4
                           mol_type = protein
                           organism = synthetic construct
SEQUENCE: 15
GGGG                                                                 4

SEQ ID NO: 16              moltype = AA   length = 5
FEATURE                    Location/Qualifiers
source                     1..5
                           mol_type = protein
                           organism = synthetic construct
SEQUENCE: 16
GGGGG                                                                5

SEQ ID NO: 17              moltype = AA   length = 6
FEATURE                    Location/Qualifiers
source                     1..6
                           mol_type = protein
                           organism = synthetic construct
SEQUENCE: 17
GGGGGG                                                               6

SEQ ID NO: 18              moltype = AA   length = 7
FEATURE                    Location/Qualifiers
source                     1..7
                           mol_type = protein
                           organism = synthetic construct
SEQUENCE: 18
GGGGGGG                                                              7

SEQ ID NO: 19              moltype = AA   length = 8
FEATURE                    Location/Qualifiers
source                     1..8
                           mol_type = protein
                           organism = synthetic construct
SEQUENCE: 19
GGGGGGGG                                                             8

SEQ ID NO: 20              moltype = AA   length = 9
FEATURE                    Location/Qualifiers
source                     1..9
                           mol_type = protein
                           organism = synthetic construct
```

-continued

```
SEQUENCE: 20
GGGGGGGGG                                                             9

SEQ ID NO: 21          moltype = AA  length = 4
FEATURE                Location/Qualifiers
source                 1..4
                       mol_type = protein
                       organism = synthetic construct
SEQUENCE: 21
CPPC                                                                  4

SEQ ID NO: 22          moltype = AA  length = 4
FEATURE                Location/Qualifiers
source                 1..4
                       mol_type = protein
                       organism = Homo sapiens
SEQUENCE: 22
CPSC                                                                  4

SEQ ID NO: 23          moltype = AA  length = 20
FEATURE                Location/Qualifiers
source                 1..20
                       mol_type = protein
                       organism = synthetic construct
SEQUENCE: 23
EPKSCDKTHT CPPCPAPPVA                                                 20

SEQ ID NO: 24          moltype = AA  length = 17
FEATURE                Location/Qualifiers
source                 1..17
                       mol_type = protein
                       organism = synthetic construct
SEQUENCE: 24
ESKYGPPCPP CPAPPVA                                                    17

SEQ ID NO: 25          moltype = AA  length = 15
FEATURE                Location/Qualifiers
source                 1..15
                       mol_type = protein
                       organism = synthetic construct
SEQUENCE: 25
CPPCPAPGGG GPSVF                                                      15

SEQ ID NO: 26          moltype = AA  length = 14
FEATURE                Location/Qualifiers
source                 1..14
                       mol_type = protein
                       organism = synthetic construct
SEQUENCE: 26
CPPCPAPGGG PSVF                                                       14

SEQ ID NO: 27          moltype = AA  length = 13
FEATURE                Location/Qualifiers
source                 1..13
                       mol_type = protein
                       organism = synthetic construct
SEQUENCE: 27
CPPCPAPGGP SVF                                                        13

SEQ ID NO: 28          moltype = AA  length = 12
FEATURE                Location/Qualifiers
source                 1..12
                       mol_type = protein
                       organism = synthetic construct
SEQUENCE: 28
CPPCPAPGPS VF                                                         12

SEQ ID NO: 29          moltype = AA  length = 4
FEATURE                Location/Qualifiers
source                 1..4
                       mol_type = protein
                       organism = Homo sapiens
SEQUENCE: 29
CPPC                                                                  4

SEQ ID NO: 30          moltype = AA  length = 121
FEATURE                Location/Qualifiers
source                 1..121
                       mol_type = protein
```

-continued

```
                         organism = synthetic construct
SEQUENCE: 30
QVQLQQPGAE LVRPGTSVKL SCKASGYTFT SYWMHWIKQR PGQGLEWIGV IDPSDNYTKY  60
NQKFKGKATL TVDTSSSTAY MQLSSLTSED SAVYFCAREG YYGSSPWFAY WGQGTLVTVS  120
S                                                                  121

SEQ ID NO: 31           moltype = AA   length = 106
FEATURE                 Location/Qualifiers
source                  1..106
                        mol_type = protein
                        organism = synthetic construct
SEQUENCE: 31
QIVMSQSPAI LSASPGEKVT MTCRARSSVS YIHWYQQKPG SSPKPWIYAT SNLASGVPGR  60
FSGSGSGTSY SLTITRVEAE DAATYYCQQW SSKPPTFGGG TKLEIK                 106

SEQ ID NO: 32           moltype = AA   length = 228
FEATURE                 Location/Qualifiers
source                  1..228
                        mol_type = protein
                        organism = synthetic construct
SEQUENCE: 32
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGK               228

SEQ ID NO: 33           moltype = AA   length = 228
FEATURE                 Location/Qualifiers
source                  1..228
                        mol_type = protein
                        organism = synthetic construct
SEQUENCE: 33
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLWCLV KGFYPSDIAV EWESNGQPEN NYKTTPPVLD  180
SDGSFFLYSR LTVDKSRWQE GNVFSCSVMH EALHNHYTQK SLSLSLGK               228

SEQ ID NO: 34           moltype = AA   length = 228
FEATURE                 Location/Qualifiers
source                  1..228
                        mol_type = protein
                        organism = synthetic construct
SEQUENCE: 34
ESKYGPPCPP CPAPPVAGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
KGQPREPQVY TLPPSQEEMT KNQVSLSCAV KGFYPSDIAV EWESNGQPEN NYKTTPPVLD  180
SDGSFFLVSR LTVDKSRWQE GNVFSCSVMH EALHNRFTQK SLSLSPGK               228

SEQ ID NO: 35           moltype = AA   length = 227
FEATURE                 Location/Qualifiers
source                  1..227
                        mol_type = protein
                        organism = synthetic construct
SEQUENCE: 35
DKTHTCPPCP APEAEGAPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPS SIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 36           moltype = AA   length = 227
FEATURE                 Location/Qualifiers
source                  1..227
                        mol_type = protein
                        organism = synthetic construct
SEQUENCE: 36
DKTHTCPPCP APEAEGAPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPS SIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 37           moltype = AA   length = 227
FEATURE                 Location/Qualifiers
source                  1..227
                        mol_type = protein
                        organism = synthetic construct
SEQUENCE: 37
DKTHTCPPCP APEAEGAPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPS SIEKTISKAK  120
GQPREPQVCT LPPSRDELTK NQVSLSCAVK GFYPSDIAVE WESNGQPENN YKTTPPVLDS  180
```

```
DGSFFLVSKL TVDKSRWQQG NVFSCSVMHE ALHNRFTQKS LSLSPGK                227

SEQ ID NO: 38          moltype = AA   length = 451
FEATURE                Location/Qualifiers
source                 1..451
                       mol_type = protein
                       organism = synthetic construct
SEQUENCE: 38
QVQLQQPGAE LVRPGTSVKL SCKASGYTFT SYWMHWIKQR PGQGLEWIGV IDPSDNYTKY   60
NQKFKGKATL TVDTSSSTAY MQLSSLTSED SAVYFCAREG YYGSSPWFAY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAEG   240
APSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPSSIEKTI SKAKGQPREP QVCTLPPSRD   360
ELTKNQVSLS CAVKGFYPSD IAVEWESNGQ PENNYKTTPP VLDSDGSFFL VSKLTVDKSR   420
WQQGNVFSCS VMHEALHNRF TQKSLSLSPG K                                  451

SEQ ID NO: 39          moltype = AA   length = 213
FEATURE                Location/Qualifiers
source                 1..213
                       mol_type = protein
                       organism = synthetic construct
SEQUENCE: 39
QIVMSQSPAI LSASPGEKVT MTCRARSSVS YIHWYQQKPG SSPKPWIYAT SNLASGVPGR   60
FSGSGSGTSY SLTITRVEAE DAATYYCQQW SSKPPTFGGG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 40          moltype = AA   length = 691
FEATURE                Location/Qualifiers
source                 1..691
                       mol_type = protein
                       organism = synthetic construct
SEQUENCE: 40
QVQLQQPGAE LVRPGTSVKL SCKASGYTFT SYWMHWIKQR PGQGLEWIGV IDPSDNYTKY   60
NQKFKGKATL TVDTSSSTAY MQLSSLTSED SAVYFCAREG YYGSSPWFAY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAEG   240
APSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPSSIEKTI SKAKGQPREP QVCTLPPSRD   360
ELTKNQVSLS CAVKGFYPSD IAVEWESNGQ PENNYKTTPP VLDSDGSFFL VSKLTVDKSR   420
WQQGNVFSCS VMHEALHNRF TQKSLSLSPG KGGGGSGGGG SGGGGSQVQL QQPGAELVRP   480
GTSVKLSCKA SGYTFTSYWM HWIKQRPGQG LEWIGVIDPS DNYTKYNQKF KGKATLTVDT   540
SSSTAYMQLS SLTSEDSAVY FCAREGYYGS SPWFAYWGQG TLVTVSSAST KGPSVFPLAP   600
SSKSTSGGTA ALGCLVKDYF PEPVTVSWNS GALTSGVHTF PAVLQSSGLY SLSSVVTVPS   660
SSLGTQTYIC NVNHKPSNTK VDKKVEPKSC D                                  691

SEQ ID NO: 41          moltype = AA   length = 452
FEATURE                Location/Qualifiers
source                 1..452
                       mol_type = protein
                       organism = synthetic construct
SEQUENCE: 41
FTITAPKDLY VVEYGSNVTM ECRFPVEREL DLLALVVYWE KEDEQVIQFV AGEEDLKPQH   60
SNFRGRASLP KDQLLKGNAA LQITDVKLQD AGVYSCIISY GGADYKRITL KVNAPYRKIN   120
QRISVDPATS EHELICQAEG YPEAEVIWTN SDHQPVSGKR SVTTSRTEGM LLNVTSSLRV   180
NATANDVFYC TFWRSQPGQN HTAELIIPEL PATHPPQNRT GGGGSDKTHT CPPCPAPEAE   240
GAPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPSSIEKT ISKAKGQPRE PQVYTLPPCR   360
DELTKNQVSL WCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 42          moltype = AA   length = 452
FEATURE                Location/Qualifiers
source                 1..452
                       mol_type = protein
                       organism = synthetic construct
SEQUENCE: 42
FTITAPKDLY VVEYGSNVTM ECRFPVEREL DLLALVVYWE KEDEQVIQFV AGEEDLKPQH   60
SNFRGRASLP KDQLLKGNAA LQITDVKLQD AGVYSCIISY GGADYKRITL KVNAPYRKIN   120
QRISVDPATS EHELICQAEG YPEAEVIWTN SDHQPVSGKR SVTTSRTEGM LLNVTSSLRV   180
NATANDVFYC TFWRSQPGQN HTAELIIPEL PATHPPQNRT GGGGSDKTHT CPPCPAPEAE   240
GAPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPSSIEKT ISKAKGQPRE PQVCTLPPSR   360
DELTKNQVSL SCAVKGFYPS DIAVEWESNG QPENNYKTTP PVLDSDGSFF LVSKLTVDKS   420
RWQQGNVFSC SVMHEALHNR FTQKSLSLSP GK                                 452

SEQ ID NO: 43          moltype = AA   length = 462
FEATURE                Location/Qualifiers
```

```
source                  1..462
                        mol_type = protein
                        organism = synthetic construct
SEQUENCE: 43
DKTHTCPPCP APEAEGAPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPS SIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGKGGG GSGGGGSGGG  240
GSFTITAPKD LYVVEYGSNV TMECRFPVER ELDLLALVVY WEKEDEQVIQ FVAGEEDLKP  300
QHSNFRGRAS LPKDQLLKGN AALQITDVKL QDAGVYSCII SYGGADYKRI TLKVNAPYRK  360
INQRISVDPA TSEHELICQA EGYPEAEVIW TNSDHQPVSG KRSVTTSRTE GMLLNVTSSL  420
RVNATANDVF YCTFWRSQPG QNHTAELIIP ELPATHPPQN RT                     462

SEQ ID NO: 44           moltype = AA  length = 462
FEATURE                 Location/Qualifiers
source                  1..462
                        mol_type = protein
                        organism = synthetic construct
SEQUENCE: 44
DKTHTCPPCP APEAEGAPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPS SIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNRFTQKS LSLSPGKGGG GSGGGGSGGG  240
GSFTITAPKD LYVVEYGSNV TMECRFPVER ELDLLALVVY WEKEDEQVIQ FVAGEEDLKP  300
QHSNFRGRAS LPKDQLLKGN AALQITDVKL QDAGVYSCII SYGGADYKRI TLKVNAPYRK  360
INQRISVDPA TSEHELICQA EGYPEAEVIW TNSDHQPVSG KRSVTTSRTE GMLLNVTSSL  420
RVNATANDVF YCTFWRSQPG QNHTAELIIP ELPATHPPQN RT                     462

SEQ ID NO: 45           moltype = AA  length = 687
FEATURE                 Location/Qualifiers
source                  1..687
                        mol_type = protein
                        organism = synthetic construct
SEQUENCE: 45
FTITAPKDLY VVEYGSNVTM ECRFPVEREL DLLALVVYWE KEDEQVIQFV AGEEDLKPQH  60
SNFRGRASLP KDQLLKGNAA LQITDVKLQD AGVYSCIISY GGADYKRITL KVNAPYRKIN  120
QRISVDPATS EHELICQAEG YPEAEVIWTN SDHQPVSGKR SVTTSRTEGM LLNVTSSLRV  180
NATANDVFYC TFWRSQPGQN HTAELIIPEL PATHPPQNRT GGGGSDKTHT CPPCPAPEAE  240
GAPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPSSIEKT ISKAKGQPRE PQVYTLPPCR  360
DELTKNQVSL WCLVKGFYPS DIAVEWESNG QPENNYKTTP PVLDSDGSFF LYSKLTVDKS  420
RWQQGNVFSC SVMHEALHNH YTQKSLSLSP GKGGGGSGGG GSGGGGSFTI TAPKDLYVVE  480
YGSNVTMECR FPVERELDLL ALVVYWEKED EQVIQFVAGE EDLKPQHSNF RGRASLPKDQ  540
LLKGNAALQI TDVKLQDAGV YSCIISYGGA DYKRITLKVN APYRKINQRI SVDPATSEHE  600
LICQAEGYPE AEVIWTNSDH QPVSGKRSVT TSRTEGMLLN VTSSLRVNAT ANDVFYCTFW  660
RSQPGQNHTA ELIIPELPAT HPPQNRT                                     687

SEQ ID NO: 46           moltype = AA  length = 702
FEATURE                 Location/Qualifiers
source                  1..702
                        mol_type = protein
                        organism = synthetic construct
SEQUENCE: 46
FTITAPKDLY VVEYGSNVTM ECRFPVEREL DLLALVVYWE KEDEQVIQFV AGEEDLKPQH  60
SNFRGRASLP KDQLLKGNAA LQITDVKLQD AGVYSCIISY GGADYKRITL KVNAPYRKIN  120
QRISVDPATS EHELICQAEG YPEAEVIWTN SDHQPVSGKR SVTTSRTEGM LLNVTSSLRV  180
NATANDVFYC TFWRSQPGQN HTAELIIPEL PATHPPQNRT GGGGSGGGGS GGGGSGGGGS  240
GGGGSGGGGS FTITAPKDLY VVEYGSNVTM ECRFPVEREL DLLALVVYWE KEDEQVIQFV  300
AGEEDLKPQH SNFRGRASLP KDQLLKGNAA LQITDVKLQD AGVYSCIISY GGADYKRITL  360
KVNAPYRKIN QRISVDPATS EHELICQAEG YPEAEVIWTN SDHQPVSGKR SVTTSRTEGM  420
LLNVTSSLRV NATANDVFYC TFWRSQPGQN HTAELIIPEL PATHPPQNRT GGGGSDKTHT  480
CPPCPAPEAE GAPSVFLFPP KPKDTLMISR TPEVTCVVVD VSHEDPEVKF NWYVDGVEVH  540
NAKTKPREEQ YNSTYRVVSV LTVLHQDWLN GKEYKCKVSN KALPSSIEKT ISKAKGQPRE  600
PQVYTLPPCR DELTKNQVSL WCLVKGFYPS DIAVEWESNG QPENNYKTTP PVLDSDGSFF  660
LYSKLTVDKS RWQQGNVFSC SVMHEALHNH YTQKSLSLSP GK                     702

SEQ ID NO: 47           moltype = AA  length = 686
FEATURE                 Location/Qualifiers
source                  1..686
                        mol_type = protein
                        organism = synthetic construct
SEQUENCE: 47
FTITAPKDLY VVEYGSNVTM ECRFPVEREL DLLALVVYWE KEDEQVIQFV AGEEDLKPQH  60
SNFRGRASLP KDQLLKGNAA LQITDVKLQD AGVYSCIISY GGADYKRITL KVNAPYRKIN  120
QRISVDPATS EHELICQAEG YPEAEVIWTN SDHQPVSGKR SVTTSRTEGM LLNVTSSLRV  180
NATANDVFYC TFWRSQPGQN HTAELIIPEL PATHPPQNRT GGGGSGGGGS GGGGSQVQLQ  240
QPGAELVRPG TSVKLSCKAS GYTFTSYWMH WIKQRPGQGL EWIGVIDPSD NYTKYNQKFK  300
GKATLTVDTS SSTAYMQLSS LTSEDSAVYF CAREGYYGSS PWFAYWGQGT LVTVSSASTK  360
GPSVFPLAPS SKSTSGGTAA LGCLVKDYFP EPVTVSWNSG ALTSGVHTFP AVLQSSGLYS  420
```

-continued

```
LSSVVTVPSS SLGTQTYICN VNHKPSNTKV DKKVEPKSCD KTHTCPPCPA PEAEGAPSVF  480
LFPPKPKDTL MISRTPEVTC VVVDVSHEDP EVKFNWYVDG VEVHNAKTKP REEQYNSTYR  540
VVSVLTVLHQ DWLNGKEYKC KVSNKALPSS IEKTISKAKG QPREPQVYTL PPCRDELTKN  600
QVSLWCLVKG FYPSDIAVEW ESNGQPENNY KTTPPVLDSD GSFFLYSKLT VDKSRWQQGN  660
VFSCSVMHEA LHNHYTQKSL SLSPGK                                       686

SEQ ID NO: 48            moltype = AA  length = 686
FEATURE                  Location/Qualifiers
source                   1..686
                         mol_type = protein
                         organism = synthetic construct
SEQUENCE: 48
FTITAPKDLY VVEYGSNVTM ECRFPVEREL DLLALVVYWE KEDEQVIQFV AGEEDLKPQH  60
SNFRGRASLP KDQLLKGNAA LQITDVKLQD AGVYSCIISY GGADYKRITL KVNAPYRKIN  120
QRISVDPATS EHELICQAEG YPEAEVIWTN SDHQPVSGKR SVTTSRTEGM LLNVTSSLRV  180
NATANDVFYC TFWRSQPGQN HTAELIIPEL PATHPPQNRT GGGGSGGGGS GGGGSQVQLQ  240
QPGAELVRPG TSVKLSCKAS GYTFTSYWMH WIKQRPGQGL EWIGVIDPSD NYTKYNQKFK  300
GKATLTVDTS SSTAYMQLSS LTSEDSAVYF CAREGYYGSS PWFAYWGQGT LVTVSSASTK  360
GPSVFPLAPS SKSTSGGTAA LGCLVKDYFP EPVTVSWNSG ALTSGVHTFP AVLQSSGLYS  420
LSSVVTVPSS SLGTQTYICN VNHKPSNTKV DKKVEPKSCD KTHTCPPCPA PEAEGAPSVF  480
LFPPKPKDTL MISRTPEVTC VVVDVSHEDP EVKFNWYVDG VEVHNAKTKP REEQYNSTYR  540
VVSVLTVLHQ DWLNGKEYKC KVSNKALPSS IEKTISKAKG QPREPQVCTL PPSRDELTKN  600
QVSLSCAVKG FYPSDIAVEW ESNGQPENNY KTTPPVLDSD GSFFLVSKLT VDKSRWQQGN  660
VFSCSVMHEA LHNRFTQKSL SLSPGK                                       686

SEQ ID NO: 49            moltype = AA  length = 686
FEATURE                  Location/Qualifiers
source                   1..686
                         mol_type = protein
                         organism = synthetic construct
SEQUENCE: 49
QVQLQQPGAE LVRPGTSVKL SCKASGYTFT SYWMHWIKQR PGQGLEWIGV IDPSDNYTKY  60
NQKFKGKATL TVDTSSSTAY MQLSSLTSED SAVYFCAREG YYGSSPWFAY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAEG  240
APSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPSSIEKTI SKAKGQPREP QVYTLPPCRD  360
ELTKNQVSLW CLVKGFYPSD IAVEWESNGQ PENNYKTTPP VLDSDGSFFL YSKLTVDKSR  420
WQQGNVFSCS VMHEALHNHY TQKSLSLSPG KGGGGSGGGG SGGGGSFTIT APKDLYVVEY  480
GSNVTMECRF PVERELDLLA LVVYWEKEDE QVIQFVAGEE DLKPQHSNFR GRASLPKDQL  540
LKGNAALQIT DVKLQDAGVY SCIISYGGAD YKRITLKVNA PYRKINQRIS VDPATSEHEL  600
ICQAEGYPEA EVIWTNSDHQ PVSGKRSVTT SRTEGMLLNV TSSLRVNATA NDVFYCTFWR  660
SQPGQNHTAE LIIPELPATH PPQNRT                                       686

SEQ ID NO: 50            moltype = AA  length = 686
FEATURE                  Location/Qualifiers
source                   1..686
                         mol_type = protein
                         organism = synthetic construct
SEQUENCE: 50
QVQLQQPGAE LVRPGTSVKL SCKASGYTFT SYWMHWIKQR PGQGLEWIGV IDPSDNYTKY  60
NQKFKGKATL TVDTSSSTAY MQLSSLTSED SAVYFCAREG YYGSSPWFAY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAEG  240
APSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPSSIEKTI SKAKGQPREP QVCTLPPSRD  360
ELTKNQVSLS CAVKGFYPSD IAVEWESNGQ PENNYKTTPP VLDSDGSFFL VSKLTVDKSR  420
WQQGNVFSCS VMHEALHNRF TQKSLSLSPG KGGGGSGGGG SGGGGSFTIT APKDLYVVEY  480
GSNVTMECRF PVERELDLLA LVVYWEKEDE QVIQFVAGEE DLKPQHSNFR GRASLPKDQL  540
LKGNAALQIT DVKLQDAGVY SCIISYGGAD YKRITLKVNA PYRKINQRIS VDPATSEHEL  600
ICQAEGYPEA EVIWTNSDHQ PVSGKRSVTT SRTEGMLLNV TSSLRVNATA NDVFYCTFWR  660
SQPGQNHTAE LIIPELPATH PPQNRT                                       686

SEQ ID NO: 51            moltype = AA  length = 687
FEATURE                  Location/Qualifiers
source                   1..687
                         mol_type = protein
                         organism = synthetic construct
SEQUENCE: 51
QVQLQQPGAE LVRPGTSVKL SCKASGYTFT SYWMHWIKQR PGQGLEWIGV IDPSDNYTKY  60
NQKFKGKATL TVDTSSSTAY MQLSSLTSED SAVYFCAREG YYGSSPWFAY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDGGGGS GGGGSFTITA  240
PKDLYVVEYG SNVTMECRFP VERELDLLAL VVYWEKEDEQ VIQFVAGEED LKPQHSNFRG  300
RASLPKDQLL KGNAALQITD VKLQDAGVYS CIISYGGADY KRITLKVNAP YRKINQRISV  360
DPATSEHELI CQAEGYPEAE VIWTNSDHQP VSGKRSVTTS RTEGMLLNVT SSLRVNATAN  420
DVFYCTFWRS QPGQNHTAEL IIPELPATHP PQNRTGGGGS DKTHTCPPCP APEAEGAPSV  480
FLFPPKPKDT LMISRTPEVT CVVVDVSHED PEVKFNWYVD GVEVHNAKTK PREEQYNSTY  540
RVVSVLTVLH QDWLNGKEYK CKVSNKALPS SIEKTISKAK GQPREPQVYT LPPCRDELTK  600
```

```
NQVSLWCLVK GFYPSDIAVE WESNGQPENN YKTTPPVLDS DGSFFLYSKL TVDKSRWQQG  660
NVFSCSVMHE ALHNHYTQKS LSLSPGK                                       687

SEQ ID NO: 52            moltype = AA  length = 687
FEATURE                  Location/Qualifiers
source                   1..687
                         mol_type = protein
                         organism = synthetic construct
SEQUENCE: 52
QVQLQQPGAE LVRPGTSVKL SCKASGYTFT SYWMHWIKQR PGQGLEWIGV IDPSDNYTKY  60
NQKFKGKATL TVDTSSSTAY MQLSSLTSED SAVYFCAREG YYGSSPWFAY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDGGGGS GGGGSFTITA  240
PKDLYVVEYG SNVTMECRFP VERELDLLAL VVYWEKEDEQ VIQFVAGEED LKPQHSNFRG  300
RASLPKDQLL KGNAALQITD VKLQDAGVYS CIISYGGADY KRITLKVNAP YRKINQRISV  360
DPATSEHELI CQAEGYPEAE VIWTNSDHQP VSGKRSVTTS RTEGMLLNVT SSLRVNATAN  420
DVFYCTFWRS QPGQNHTAEL IIPELPATHP PQNRTGGGGS DKTHTCPPCP APEAEGAPSV  480
FLFPPKPKDT LMISRTPEVT CVVVDVSHED PEVKFNWYVD GVEVHNAKTK PREEQYNSTY  540
RVVSVLTVLH QDWLNGKEYK CKVSNKALPS SIEKTISKAK GQPREPQVYT LPPSRDELTK  600
NQVSLTCLVK GFYPSDIAVE WESNGQPENN YKTTPPVLDS DGSFFLYSKL TVDKSRWQQG  660
NVFSCSVMHE ALHNHYTQKS LSLSPGK                                       687

SEQ ID NO: 53            moltype = AA  length = 451
FEATURE                  Location/Qualifiers
source                   1..451
                         mol_type = protein
                         organism = synthetic construct
SEQUENCE: 53
QVQLQQPGAE LVRPGTSVKL SCKASGYTFT SYWMHWIKQR PGQGLEWIGV IDPSDNYTKY  60
NQKFKGKATL TVDTSSSTAY MQLSSLTSED SAVYFCAREG YYGSSPWFAY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAEG  240
APSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPSSIEKTI SKAKGQPREP QVYTLPPCRD  360
ELTKNQVSLW CLVKGFYPSD IAVEWESNGQ PENNYKTTPP VLDSDGSFFL YSKLTVDKSR  420
WQQGNVFSCS VMHEALHNHY TQKSLSLSPG K                                  451

SEQ ID NO: 54            moltype = AA  length = 60
FEATURE                  Location/Qualifiers
source                   1..60
                         mol_type = protein
                         organism = Mus musculus
SEQUENCE: 54
SNFRGRASLP KDQLLKGNAA LQITDVKLQD AGVYCCIISY GGADYKRITL KVNAPYRKIN  60

SEQ ID NO: 55            moltype = AA  length = 60
FEATURE                  Location/Qualifiers
source                   1..60
                         mol_type = protein
                         organism = Homo sapiens
SEQUENCE: 55
SSYRQRARLL KDQLSLGNAA LQITDVKLQD AGVYRCMISY GGADYKRITV KVNAPYNKIN  60

SEQ ID NO: 56            moltype = AA  length = 25
FEATURE                  Location/Qualifiers
source                   1..25
                         mol_type = protein
                         organism = synthetic construct
VARIANT                  1..25
                         note = This sequence may encompass 2-5 GGGGS repeats
SEQUENCE: 56
GGGGSGGGGS GGGGSGGGGS GGGGS                                         25
```

CD20-PD1 BINDING MOLECULES AND METHODS OF USE THEREOF

1. CROSS-REFERENCE TO RELATED APPLICATIONS

This application claims the priority benefit of U.S. provisional application No. 63/278,454, filed Nov. 11, 2021 and U.S. provisional application No. 63/278,374, filed Nov. 11, 2021, the contents of each of which are incorporated herein in their entireties by reference thereto.

2. SEQUENCE LISTING

The instant application contains a Sequence Listing which has been submitted electronically and is hereby incorporated by reference in its entirety. Said copy, created on Nov. 8, 2022, is named RGN-012US_SL.xml and is 63,928 bytes in size.

3. BACKGROUND

Autoimmune disease occurs when there is an aberrant immune response by an organism to its own cells and tissues. Efforts to understand autoimmunity have been made for many decades. During this time, it has become apparent that the immune system evolved multiple mechanisms for controlling self-reactivity. Defects in one or more of these mechanisms can lead to breakdown of tolerance and can result in autoimmune disease.

The initial trigger for both systemic and organ-specific autoimmune disorders likely involves recognition of self or foreign molecules by innate sensors. This recognition triggers inflammatory responses and engagement of previously quiescent autoreactive T and B cells. Theofilopolous, Kono, and Baccala, 2017, Nat Immunol, 18(17):716-724. Autoreactivity ranges from a low "physiologic" level of self-reactivity essential for lymphocyte selection and immune system homeostasis, to an intermediate level of autoimmunity that manifests as circulating autoantibodies and minor tissue infiltrates without clinical consequences, to pathogenic autoimmunity associated with immune-mediated organ injury. Theofilopolous, Kono, and Baccala, 2017, Nat Immunol, 18(17):716-724. Autoimmune diseases are divided into organ-specific (e.g. type I diabetes (T1D), multiple sclerosis (MS), inflammatory bowel diseases (IBDs), myasthenia gravis) and systemic (e.g. systemic lupus erythematosus (SLE), rheumatoid arthritis (RA), Sjögren's syndrome) and can be mediated by autoantibodies or cytotoxic T cells, but in all instances helper T cells are required. Theofilopolous, Kono, and Baccala, 2017, Nat Immunol, 18(17):716-724.

Most autoimmune diseases exhibit clinical heterogeneity, a polygenic nature, and multifactorial contributions often requiring both genetic and environmental factors. Four mechanisms contribute to the control of escaping autoreactive T and B cells: inhibitory molecules, anergy, ignorance, and active suppression. Kono and Theofilopolous, Kono, and Baccala, 2017, Nat Immunol, 18(17):716-724. Several inhibitory molecules (e.g. CTLA-4, PD-1, LAG-3, TIM3, VISTA, TIGIT, FcγRIIb, certain Siglecs) are expressed on the surface of T and B cells to curtail excessive immune responses, both normal and anti-self. Deficiency of some of these molecules leads to autoimmunity, providing strong evidence that autoreactive lymphocytes are present in the peripheral repertoire but are normally under control. See Paterson and Sharpe, 2010, Nat Ummunol, 11:109-111;

Okazaki et al., 2013, Nat Immunol, 14:1212-1218; Pincetic et al., 2014, Nat Immunol, 15:707-716; Macauley, Crocker, and Paulson, 2914, Nat Rev Immunol, 14:653-666; Ceeraz et al., 2016, Arthritis Rheumatol 69(4):814-825; and Schmitt et al., 2016, J Exp Med, 213:1627-1644. A wide range of immune-related adverse events due to unchecked autoreactivity frequently occurs. Michot et al., 2016, Eur J Cancer, 54:139-148.

Existing treatments for autoimmune diseases have had only limited success. For example, it is often possible to correct organ-specific autoimmune disease through metabolic control. Where function is lost and cannot be restored, mechanical substitutes or tissue grafts may be appropriate. While it may be possible to alleviate some of the symptoms using this approach, no effective long-term curative treatment exists for several of the most disabling autoimmune disorders. While a number of compounds, including insulin, corticosteroids and modified beta interferon can ameliorate some of the symptoms of autoimmune diseases, they can have serious side effects and/or require long-term use. General immunosuppressive drug therapies, such as chronic treatment with cyclosporin A, FK506 and rapamycin have also been unable to provide a cure for these diseases, and their use is accompanied by a host of deleterious side effects. Said effects include nephrotoxicity, increased predisposition to infectious diseases, and enhanced incidence of neoplasia.

Accordingly, novel therapeutic compositions and protocols are sought that can be used to treat autoimmune diseases.

4. SUMMARY

The present disclosure provides novel CD20-PD1 binding molecules. The CD20-PD1 binding molecules of the disclosure typically comprise or consist of CD20-PD1 monomers that include one or more CD20 targeting moieties and/or one or more PD1 agonist moieties. The CD20-PD1 binding molecules of the disclosure comprise a protein, the protein comprising at least one CD20 targeting moiety, at least one PD1 agonist moiety, at least one dimerization moiety, and optionally, one or more linker moieties separating one or more moieties in the protein. In some embodiments where the CD20 targeting moiety is an anti-CD20 Fab, the PD1 agonist moiety is the ectodomain of PDL1, and the dimerization moiety is an Fc domain, the optionally i) the light chain of the Fab is not fused to the ectodomain of PDL1 or a PD1-binding portion thereof; ii) the PD1 agonist moiety is not N-terminal to a VH of the anti-CD20 Fab; iii) the PD1 agonist moiety is not C-terminal to the Fc domain; iv) the protein is monovalent for the CD20 targeting moiety and/or the PD1 agonist moiety; iv) the protein is asymmetrical; v) the protein comprises an Fc heterodimer; or any combination of two or more of the foregoing (i) through (vi).

Exemplary CD20-PD1 binding molecules are disclosed in Section 6.2 and numbered embodiments 1 to 142. Exemplary CD20 targeting moieties are disclosed in Section 6.2.1 and numbered embodiments 2 to 6. Exemplary PD1 agonist moieties are disclosed in Section 6.4 and numbered embodiments 7 to 22.

The disclosure further provides nucleic acids encoding the CD20-PD1 binding molecules, the CD20-PD1 monomers, and CD20 targeting moieties and PD1 agonist moieties. The nucleic acids encoding the CD20-PD1 binding molecules and CD20-PD1 monomers that are composed of two or more polypeptide chains can be a single nucleic acid (e.g., a vector encoding all polypeptide chains) or a plurality of nucleic acids (e.g., two or more vectors encoding the different polypeptide chains). The disclosure further provides host cells and cell lines engineered to express the nucleic acids and the CD20-PD1 binding molecules, the CD20-PD1 monomers, the CD20 targeting moieties, and the PD1 agonist moieties of the disclosure. The disclosure further provides methods of producing a CD20-PD1 binding molecule, a CD20-PD1 monomer, a CD20 targeting moiety and a PD1 agonist moiety of the disclosure. Exemplary nucleic acids, host cells, cell lines, and methods of producing the CD20-PD1 binding molecules, the CD20-PD1 monomers, the CD20 targeting moieties and the PD1 agonist moieties are described in Section 6.8 and numbered embodiments 150 to 152, infra.

The disclosure further provides pharmaceutical compositions comprising the CD20-PD1 binding molecules, the CD20-PD1 monomers, the CD20 targeting moieties and the PD1 agonist moieties of the disclosure. Exemplary pharmaceutical compositions are described in Section 6.9 and numbered embodiment 153, infra.

Further provided herein are methods of using the CD20-PD1 binding molecules, the CD20-PD1 monomers, the CD20 targeting moieties, the PD1 agonist moieties and the pharmaceutical compositions of the disclosure, e.g., for treating autoimmune diseases, repressing a cellular autoimmune response, or repressing the immune system of a subject. Exemplary methods are described in Section 6.10 and numbered embodiments 154 to 165, infra.

5. BRIEF DESCRIPTION OF THE FIGURES

FIGS. 1A-1L are a series of cartoons representing various formats of CD20-PD1 binding molecules according to certain embodiments. Heavy chain variable domains of the CD20 targeting moieties are shown in a striped pattern, light chain variable domains are shown in a dotted pattern, and PD1 agonist moieties (e.g., the ectodomain of PDL1 or PDL2 or a PD1 binding portion thereof) are shown as circles with dashed lines.

FIGS. 2A and 2B present a series of cartoons representing tested murine CD20-PD1 binding molecules PD1 (anti-mCD20×mPDL1) (molecules A-L; FIG. 2A) and controls (molecules M-S; FIG. 2B).

FIG. 5A is a schematic description of the luciferase reporter assay and FIG. 5B is a cartoon representation depicting the interactions between the key players described in FIG. 5A.

FIGS. 6A-6E depict test molecules (FIG. 6A) and a series of traces using the same (FIGS. 6B-6E). The traces depict mPD1 agonism measured utilizing the bioassay depicted in FIG. 5. Cells and molecules used as indicated for each individual trace.

FIG. 7 depicts the experimental design for a dose titration efficacy test in pre-diabetic Non-Obese Diabetic (NOD) mice.

FIGS. 8A-8I present a series of traces depicting individual animal data demonstrating spontaneous diabetes onset in the presence of the indicated control or CD20-PD1 binding molecule (anti-mCD20×mPDL1 ectodomain).

Figure 9A:
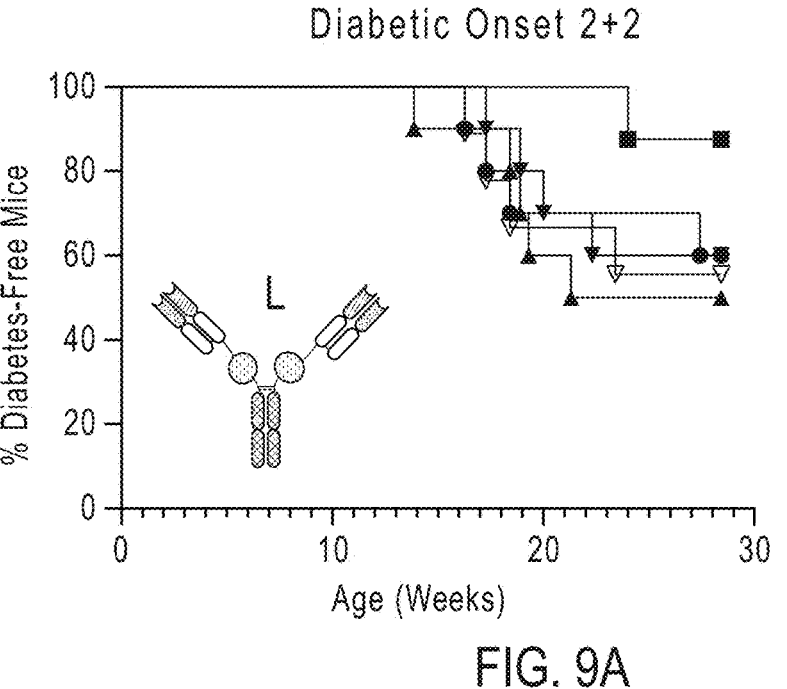
Figure 9B:
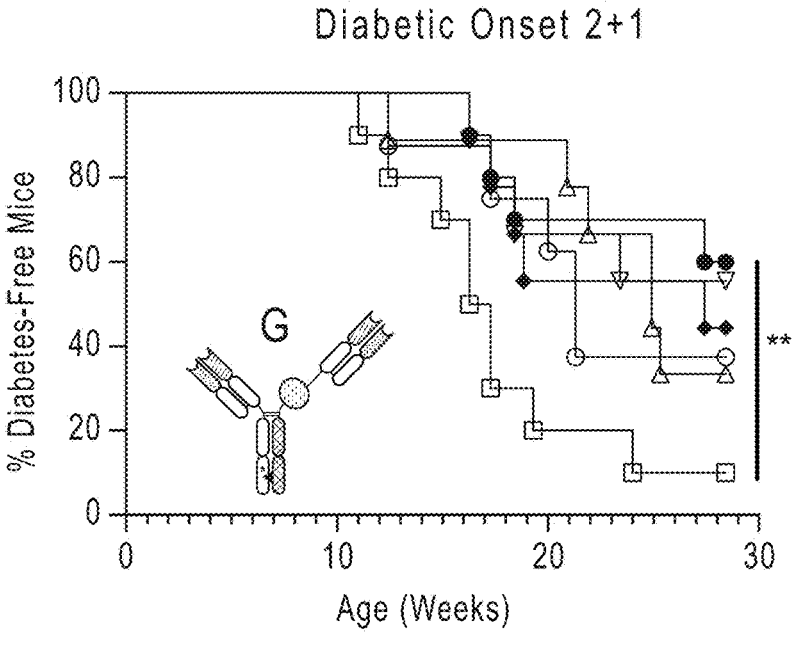

FIGS. 9A and 9B depict graphs demonstrating the ability of CD20-PD1 binding molecule (anti-mCD20×mPDL1 ectodomain) (top: molecule L of FIG. 2A; bottom: molecule G of FIG. 2B) to modulate diabetic onset in NOD mice.

Figure 10A:
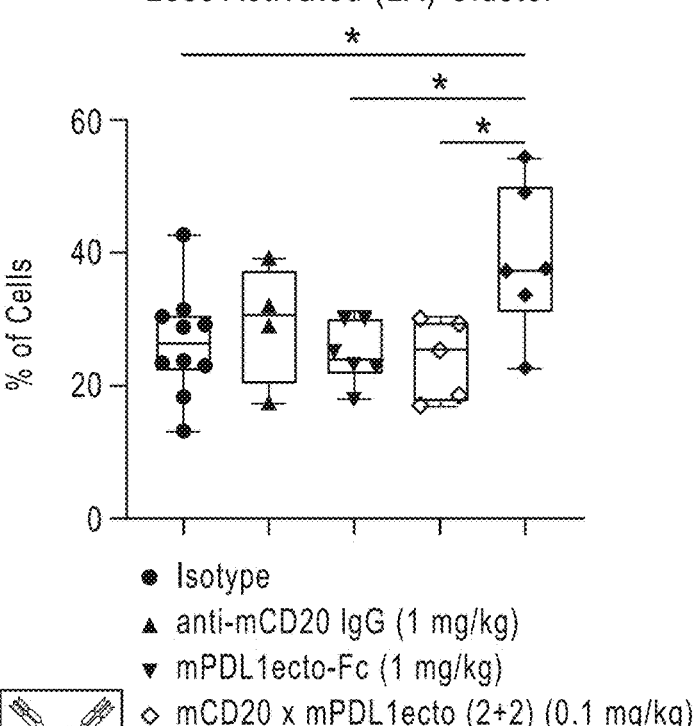
Figure 10B:
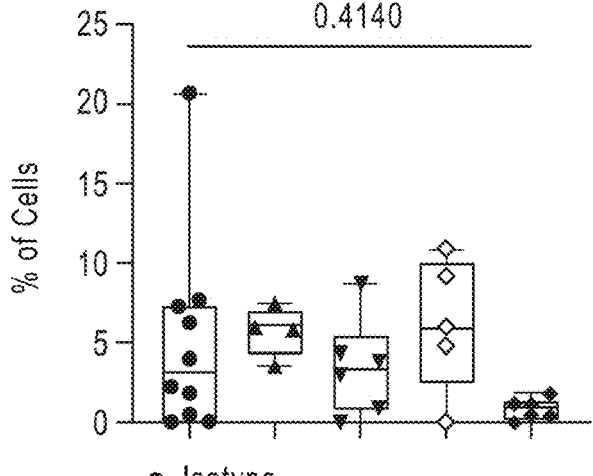
Figure 10B:
Figure 10C:
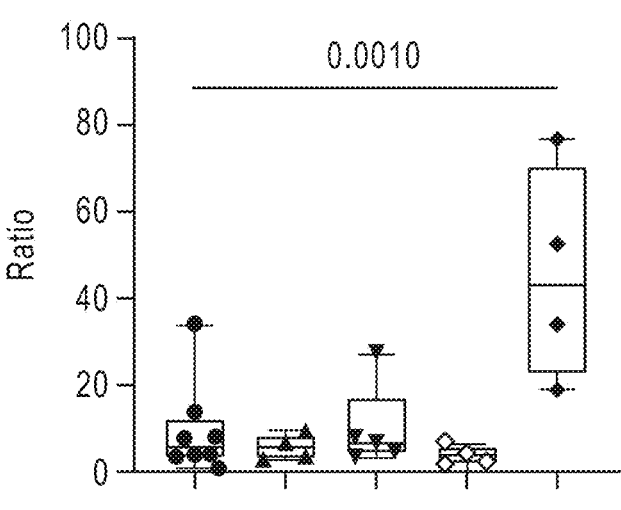
Figure 10C:
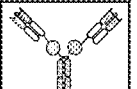

FIGS. 10A-10C are box plots depicting the reduction of activated autoreactive islet-specific CD8+ T-cell infiltration into NOD mice pancreases following treatment with CD20-PD1 binding molecule (anti-mCD20×mPDL1 ectodomain). * $p < 0.05$.

Figures 11A, 11B:
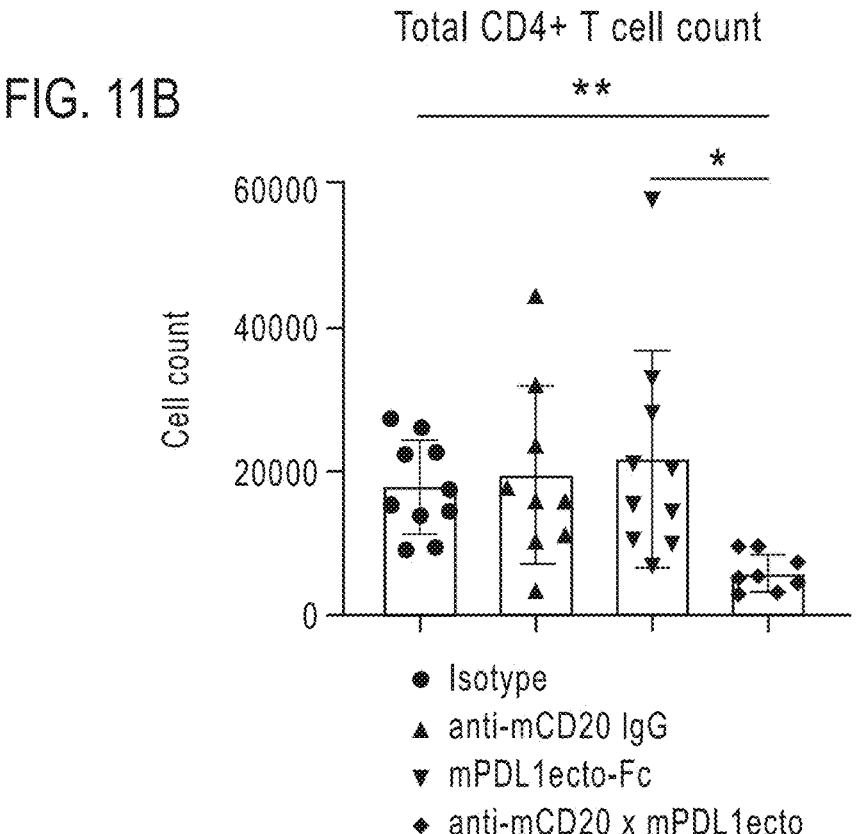
Figure 11C:
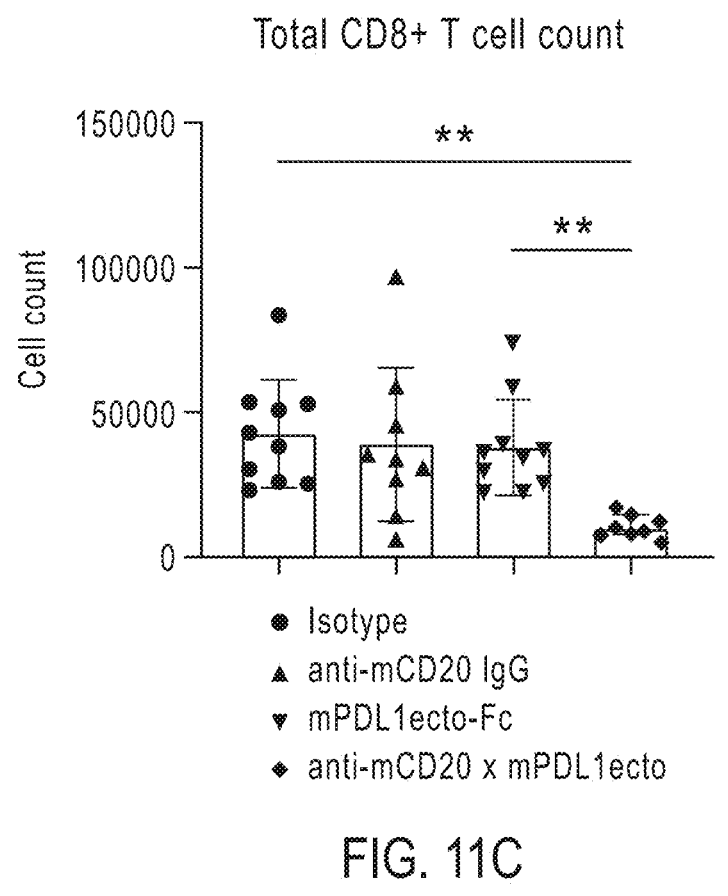

FIGS. 11A-11C are box plots depicting the reduction of activated autoreactive CD3+, CD4+, and CD8+ T-cell infiltration into spinal cords of EAE-MS mice following treatment with CD20-PD1 binding molecule (anti-mCD20×mPDL1 ectodomain) treatment. * $p < 0.05$,  $p < 0.01$, * $p < 0.001$.

6. DETAILED DESCRIPTION

6.1. Definitions

About, Approximately: The terms "about", "approximately" and the like are used throughout the specification in front of a number to show that the number is not necessarily exact (e.g., to account for fractions, variations in measurement accuracy and/or precision, timing, etc.). It should be understood that a disclosure of "about X" or "approximately X" where X is a number is also a disclosure of "X." Thus, for example, a disclosure of an embodiment in which one sequence has "about X % sequence identity" to another sequence is also a disclosure of an embodiment in which the sequence has "X % sequence identity" to the other sequence.

And and Or: Unless indicated otherwise, an "or" conjunction is intended to be used in its correct sense as a Boolean logical operator, encompassing both the selection of features in the alternative (A or B, where the selection of A is mutually exclusive from B) and the selection of features in conjunction (A or B, where both A and B are selected). In some places in the text, the term "and/or" is used for the same purpose, which shall not be construed to imply that "or" is used with reference to mutually exclusive alternatives.

Antigen Binding Domain or ABD, and Antigen Binding Fragment: The term "antigen binding domain" or "ABD", and "Antigen Binding Fragment" as used herein refers to the portion of a targeting moiety that is capable of specific, non-covalent, and reversible binding to a target molecule.

Associated: The term "associated" in the context of a CD20-PD1 binding molecule or a component thereof (e.g., a CD20 targeting moiety; a PD1 agonist moiety; a dimerization moiety) refers to a functional relationship between two or more polypeptide chains or portions of a polypeptide chain. In particular, the term "associated" means that two or more polypeptides are associated with one another, e.g., non-covalently through molecular interactions or covalently through one or more disulfide bridges or chemical cross-linkages, so as to produce a functional CD20-PD1 binding molecule. Examples of associations that might be present in a CD20-PD1 binding molecule of the disclosure include (but are not limited to) associations between homodimeric or heterodimeric Fc domains in an Fc region, associations between VH and VL regions in a Fab or scFv, associations between CH1 and CL in a Fab, and associations between CH3 and CH3 in a domain substituted Fab.

Bivalent: The term "bivalent" as used herein in reference to a CD20-PD1 binding molecule with respect to a CD20 targeting moiety and/or PD1 agonist moiety means that the CD20-PD1 binding molecule has two CD20 targeting moieties (e.g., two antigen binding fragments of anti-CD20 antibodies) and/or two PD1 agonist moieties (e.g. two PDL1 agonist moieties, two PDL2 agonist moieties or a combination thereof), respectively. The CD20-PD1 binding molecule may be bivalent for one type of moiety (e.g., a CD20 targeting moiety) and monovalent for another type of moiety (e.g., a PD1 agonist moiety).

CD20-PD1 Binding Molecule: The term "CD20-PD1 binding molecule" refers to a molecule comprising at least one CD20 targeting moiety and at least one PD1 agonist moiety. Generally, a CD20-PD1 binding molecule is a molecule composed of one or more polypeptide chains (e.g., one, two, three or four polypeptide chains) together comprising at least one CD20 targeting moiety and at least one PD1 agonist moiety.

In the context of the CD20-PD1 binding molecules of the disclosure, the term "CD20-PD1 binding molecule" sometimes refers to the core components of the molecule, namely the CD20 targeting moiety and the PD1 agonist moiety and sometimes also the dimerization moieties, such as Fc domains and any/or associated linker moieties. It is to be understood that the term "CD20-PD1 binding molecule" extends also to molecules comprising additional features, e.g., one or more stabilization moieties, one or more dimerization moieties, one or more linker moieties, and any combination of the foregoing, unless the context dictates otherwise.

CD20 Targeting Moiety: The term "CD20 targeting moiety" refers to any molecule or binding portion thereof (e.g., an immunoglobulin or an antigen binding fragment thereof) that can bind to CD20. In some embodiments, the CD20 targeting moiety comprises an antigen binding fragment of an anti-CD20 antibody. The CD20-binding fragment of the anti-CD20 antibody can be in the form of a Fab, a Fv or an scFv. The term "CD20 targeting moiety" includes a molecule that can bind to any domain or region of CD20, including a topological domain or a transmembrane domain. In some embodiments, a CD20 targeting moiety is a molecule that can bind to a region of CD20 displayed extracellularly on a surface of a cell (e.g., a B cell). CD20 targeting moieties are further described in Section 6.2.

Complementarity Determining Region or CDR: The terms "complementarity determining region" or "CDR," as used herein, refer to the sequences of amino acids within antibody variable regions which confer antigen specificity and binding affinity. In general, there are three CDRs in each heavy chain variable region (CDR-H1, CDR-H2, CDR-H3) and three CDRs in each light chain variable region (CDR1-L1, CDR-L2, CDR-L3). Exemplary conventions that can be used to identify the boundaries of CDRs include, e.g., the Kabat definition, the Chothia definition, the ABM definition and the IMGT definition. See, e.g., Kabat, 1991, "Sequences of Proteins of Immunological Interest," National Institutes of Health, Bethesda, Md. (Kabat numbering scheme); Al-Lazikani et al., 1997, J. Mol. Biol. 273:927-948 (Chothia numbering scheme); Martin et al., 1989, Proc. Natl. Acad. Sci. USA 86:9268-9272 (ABM numbering scheme); and Lefranc et al., 2003, Dev. Comp. Immunol. 27:55-77 (IMGT numbering scheme). Public databases are also available for identifying CDR sequences within an antibody.

Dimerization Moiety: The term "dimerization moiety" refers to a polypeptide chain or an amino acid sequence capable of facilitating an association between two polypeptide chains to form a dimer. A first dimerization moiety can associate with an identical second dimerization moiety, or can associate with a second dimerization moiety that is different from the first. In some embodiments, a dimerization moiety is an Fc domain, with the association of two Fc domains forming an Fc region. Thus, the Fc region can be homodimeric or heterodimeric.

EC50: The term "EC50" refers to the half maximal effective concentration of a molecule, such as a CD20-PD1 binding molecule, which induces a response halfway between the baseline and maximum after a specified exposure time. The EC50 essentially represents the concentration of an antibody or CD20-PD1 binding molecule where 50% of its maximal effect is observed. In certain embodiments, the EC50 value equals the concentration of a CD20-PD1 binding molecule that gives half-maximal activation in an assay as described in Section 7.1.3.3.

Epitope: An epitope, or antigenic determinant, is a portion of an antigen (e.g., CD20) recognized by an antibody or other antigen-binding moiety as described herein. An epitope can be linear or conformational.

Fab: The term "Fab" in the context of a CD20 targeting moiety of the disclosure refers to a pair of polypeptide chains, the first comprising a variable heavy (VH) domain of an antibody N-terminal to a first constant domain (referred to herein as C1), and the second comprising variable light (VL) domain of an antibody N-terminal to a second constant domain (referred to herein as C2) capable of pairing with the first constant domain. In a native antibody, the VH is N-terminal to the first constant domain (CH1) of the heavy chain and the VL is N-terminal to the constant domain of the light chain (CL). The Fabs of the disclosure can be arranged according to the native orientation or include domain substitutions or swaps that facilitate correct VH and VL pairings. For example, it is possible to replace the CH1 and CL domain pair in a Fab with a CH3-domain pair to facilitate correct modified Fab-chain pairing in heterodimeric molecules. It is also possible to reverse CH1 and CL, so that the CH1 is attached to VL and CL is attached to the VH, a configuration generally known as Crossmab, a type of "domain exchange".

Fc Domain and Fc Region: The term "Fc domain" refers to a portion of the heavy chain that pairs with the corresponding portion of another heavy chain. The term "Fc region" refers to the region of antibody-based binding molecules formed by association of two heavy chain Fc domains. The two Fc domains within the Fc region may be the same or different from one another. In a native antibody the Fc domains are typically identical, but one or both Fc domains might advantageously be modified to allow for heterodimerization, e.g., via a knob-in-hole interaction and/or for purification, e.g., via star mutations.

Host Cell or Recombinant Host Cell: The terms "host cell" and "recombinant host cell" as used herein refer to a cell that has been genetically engineered, e.g., through introduction of a heterologous nucleic acid. It should be understood that such terms are intended to refer not only to the particular subject cell but to the progeny of such a cell. Because certain modifications can occur in succeeding generations due to either mutation or environmental influences, such progeny may not, in fact, be identical to the parent cell, but are still included within the scope of the term "host cell" as used herein. A host cell can carry the heterologous nucleic acid transiently, e.g., on an extrachromosomal heterologous expression vector, or stably, e.g., through integration of the heterologous nucleic acid into the host cell genome. For purposes of expressing a CD20-PD1 binding molecule, a host cell can be a cell line of mammalian origin or mammalian-like characteristics, such as monkey kidney cells (COS, e.g., COS-1, COS-7), HEK293, baby hamster kidney (BHK, e.g., BHK21), Chinese hamster ovary (CHO), NSO, PerC6, BSC-1, human hepatocellular carcinoma cells (e.g., Hep G2), SP2/0, HeLa, Madin-Darby bovine kidney (MDBK), myeloma and lymphoma cells, or derivatives and/or engineered variants thereof. The engineered variants include, e.g., glycan profile modified and/or site-specific integration site derivatives.

Monomer and CD20-PD1 Monomer: The terms "monomer" and "CD20-PD1 monomer" as used herein refer to a molecule comprising a first polypeptide chain which (a) comprises at least one CD20 targeting moiety and is capable of associating with a second polypeptide chain; (b) comprises at least one PD1 agonist moiety and is capable of associating with a second polypeptide chain; (c) comprises a dimerization moiety (e.g., an Fc domain) and is capable of associating with a corresponding dimerization moiety (e.g., another Fc domain) on a second polypeptide chain; or (d) any combination of (a), (b), and (c), above. Monomers are capable of associating with other monomers through a dimerization moiety (e.g., Fc domain) pairing. In some embodiments, one or more of associations between monomers are stabilized through hinge sequences or other portions of Fc domains. Thus, a monomer of the disclosure is capable of associating with another monomer to form a dimer. The dimers can be homodimeric, in which each constituent monomer is identical, or heterodimeric, in which case each constituent monomer is different. As used herein, the reference to a "monomer" is for convenience and does not preclude the presence of a one or more additional polypeptide chains, for example one or more light chains of one or more Fab domains. Thus, a "dimer" of two monomers may include more than two polypeptide chains, e.g., may include three, four or more polypeptide chains and the reference to a monomer or dimer is not intended to imply any temporal order of association between polypeptide chains.

Monovalent: The term "monovalent" as used herein in reference to a CD20-PD1 binding molecule with respect to a CD20 targeting moiety and/or PD1 agonist moiety means that the CD20-PD1 binding molecule has one CD20 targeting moiety (e.g., one antigen binding domain of an anti-CD20 antibody) and/or one PD1 agonist moiety (e.g. one PDL1 agonist moiety or one PDL2 agonist moiety), respectively. The CD20-PD1 binding molecule may be monovalent for one type of moiety (e.g., a PD1 agonist moiety) and bivalent for another type of moiety (e.g., a CD20 targeting moiety).

Multivalent: The term "multivalent" as used herein in reference to a CD20-PD1 binding molecule with respect to a CD20 targeting moiety and/or PD1 agonist moiety means that the CD20-PD1 binding molecule has two or more CD20 targeting moieties (e.g., two antigen binding fragments of anti-CD20 antibodies) and/or two or more PD1 agonist moieties (e.g. two PDL1 agonist moieties, two PDL2 agonist moieties or a combination thereof), respectively. The CD20-PD1 binding molecule may be multivalent for one type of moiety (e.g., a CD20 targeting moiety) and monovalent for another type of moiety (e.g., a PD1 agonist moiety).

Operably linked: The term "operably linked" as used herein refers to a functional relationship between two or more regions of a polypeptide chain in which the two or more regions are linked so as to produce a functional polypeptide, or two or more nucleic acid sequences, e.g., to produce an in-frame fusion of two polypeptide components or to link a regulatory sequence to a coding sequence.

PD1 Agonist Moiety: The term "PD1 agonist moiety" refers to any molecule or portion thereof that can bind to and agonize PD1. In some embodiments, the PD1 agonist moiety comprises an amino acid sequence having at least 70% sequence identity to the extracellular domain of programmed death-ligand 1 (PDL1) or a PD1-binding portion thereof, preferably a mammalian PDL1 (e.g., human or murine PDL1). In other embodiments, the PD1 agonist moiety comprises an amino acid sequence having at least 70% sequence identity to the extracellular domain of programmed death-ligand (PDL2) or a PD1-binding portion thereof, preferably a mammalian PDL2 (e.g., human or murine PDL2). The extracellular domains of PDL1 and PDL2 are sometimes known as the "PDL1 ectodomain" and "PDL2 ectodomain," respectively. The terms "PDL1 ectodomain" and "PDL2 ectodomain" are conveniently used in this specification to refer not only to the PDL1 and PDL2 ectodomains but additionally to fragments and variant sequences having PD1 binding activity. Accordingly, references to the terms "PDL1 ectodomain" and "PDL2 ectodomain" in the specification are intended to encompass PD1 binding portions of the PDL1 and PDL2 ectodomains as well as variants thereof having PD1 binding function, e.g., amino acid sequences having at least 70% or greater sequence identity to PD1 or PD2 and retention of PDL1 binding.

A CD20-PD1 binding molecule can comprise a PD1 agonist moiety with one or more amino acid substitutions, deletions and/or insertions compared to a corresponding wild type sequence. For example, in some embodiments, the PD1 agonist moiety is murine PDL1 ectodomain comprising a C113S substitution.

PD1 agonist moieties are further described in Section 6.2.1.

Single Chain Fv or scFv: The term "single chain Fv" or "scFv" as used herein refers to a polypeptide chain comprising the VH and VL domains of antibody, where these domains are present in a single polypeptide chain.

Subject: The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

Treat, Treatment, Treating: As used herein, the terms "treat", "treatment" and "treating" refer to the reduction or amelioration of the progression, severity and/or duration of a disorder as described herein, the amelioration of one or more symptoms (preferably, one or more discernible symptoms) of a condition or disorder as described herein, or prevention of a condition or disorder as described herein, e.g., an autoimmune or inflammatory condition or disorder, resulting from the administration of a molecule or composition (e.g., one or more CD20-PD1 binding molecules of the disclosure). In specific embodiments, the terms "treat", "treatment" and "treating" refer to the amelioration of at least one measurable physical parameter of a disorder, e.g., an autoimmune disorder, not necessarily discernible by the patient. In other embodiments the terms "treat", "treatment" and "treating" refer to the inhibition of the progression or onset of a disorder, either physically by, e.g., stabilization of a discernible symptom, physiologically by, e.g., stabilization of a physical parameter, or both.

Universal Light Chain: The term "universal light chain" as used herein in the context of a targeting moiety refers to a light chain polypeptide capable of pairing with the heavy chain region of the targeting moiety and also capable of pairing with other heavy chain regions. Universal light chains are also known as "common light chains."

VH: The term "VH" refers to the variable region of an immunoglobulin heavy chain of an antibody, including the heavy chain of an scFv or a Fab.

VL: The term "VL" refers to the variable region of an immunoglobulin light chain, including the light chain of an scFv or a Fab.

6.2. CD20-PD1 Binding Molecules

The present disclosure provides CD20-PD1 binding molecules comprising at least one CD20 targeting moiety and at least one PD1 agonist moiety. In some embodiments, a CD20-PD1 binding molecule further comprises a dimerization moiety.

The CD20-PD1 binding molecules of the disclosure typically comprise or consist of CD20-PD1 monomers that include one or more CD20 targeting moieties and/or one or more PD1 agonist moieties. The CD20-PD1 binding molecules of the disclosure comprise a protein, the protein comprising at least one CD20 targeting moiety, at least one PD1 agonist moiety, at least one dimerization moiety, and optionally, one or more linker moieties separating one or more moieties in the protein.

In some embodiments, the PD1 agonist moiety is positioned between the CD20 targeting moiety and the dimerization moiety of a CD20-PD1 monomer. In such embodiments, when the CD20 targeting moiety and the PD1 agonist moiety are both N-terminal to the dimerization moiety, the CD20-PD1 monomer thus has an N-to-C terminal orientation of CD20 targeting moiety—PD1 agonist moiety—dimerization moiety. In such embodiments, when the CD20 targeting moiety and the PD1 agonist moiety are both C-terminal to the dimerization moiety, the CD20-PD1 monomer thus has an N-to-C terminal orientation of dimerization moiety—PD1 agonist moiety—CD20 targeting moiety.

In some embodiments, e.g., embodiments where the CD20 targeting moiety is an anti-CD20 Fab, the PD1 agonist moiety is the ectodomain of PDL1, and the dimerization moiety is an Fc domain, the CD20-PD1 binding molecules optionally have one or more of the following features i) the light chain of the Fab is not fused to the ectodomain of PDL1 or a PD1-binding portion thereof; ii) the PD1 agonist moiety is not N-terminal to a VH of the anti-CD20 Fab; iii) the PD1 agonist moiety is not C-terminal to the Fc domain; iv) the protein is monovalent for the CD20 targeting moiety and/or the PD1 agonist moiety; v) the protein is asymmetrical; vi) the protein comprises an Fc heterodimer; or any combination of two or more of the foregoing (i) through (vi). In some embodiments, the CD20-PD1 binding molecules have feature i) (i.e., the light chain of the Fab is not fused to the ectodomain of PDL1 or a PD1-binding portion thereof). In some embodiments, the CD20-PD1 binding molecules have feature ii) (i.e., the PD1 agonist moiety is not N-terminal to a VH of the anti-CD20 Fab). In some embodiments, the CD20-PD1 binding molecules have feature iii) (i.e., the PD1 agonist moiety is not C-terminal to the Fc domain). In some embodiments, the CD20-PD1 binding molecules have feature iv) (i.e., the protein is monovalent for the CD20 targeting moiety and/or the PD1 agonist moiety). In some embodiments, the CD20-PD1 binding molecules have feature v) (i.e., the protein is asymmetrical). In some embodiments, the CD20-PD1 binding molecules have feature vi)

(i.e., the protein comprises an Fc heterodimer). A CD20-PD1 binding molecule of the present disclosure may have any combination of two, three, four, five, or all of the preceding features. For example, in some embodiments, a CD20-PD1 binding molecule disclosed herein has feature ii) (i.e., the PD1 agonist moiety is not N-terminal to a VH of the anti-CD20 Fab) and feature iii) (i.e., the PD1 agonist moiety is not C-terminal to the Fc domain).

Exemplary dimerization moieties are described in Section 6.5 and include Fc domains that confer homodimerization or heterodimerization capability to the CD20-PD1 binding molecule.

A CD20-PD1 binding molecule can be composed of one or more polypeptides. In some embodiments, the CD20-PD1 binding molecule is composed of a plurality of (e.g. two) monomers comprising at least one CD20 targeting moiety and/or at least one PD1 agonist moieties and in some embodiments also comprising dimerization moieties. In some embodiments, the CD20-PD1 binding molecule of the disclosure is composed of two monomers, optionally in association with one or more additional polypeptide chains (e.g., a polypeptide chain comprising the light chain of an anti-CD20 Fab moiety). The monomers can be identical, thereby forming a homodimer, or different, thereby forming a heterodimer. The dimerization moieties of each monomer of a CD20-PD1 binding molecule can be configured to dimerize together. Exemplary dimerization moieties are described in Section 6.5.

The one or more CD20 targeting moieties and the one or more PD1 agonist moieties can be included on the same arm of a CD20-PD1 binding molecule (e.g., wherein the CD20 targeting moiety comprises an anti-CD20 Fab and the PD1 agonist moiety comprises a PDL1-based PD1 agonist moiety, the variable heavy or variable light chain of the anti-CD20 Fab and the PDL1-based PD1 agonist moiety are on the same polypeptide chain), or can be included on different arms of a bispecific CD20-PD1 agonist (e.g., wherein the CD20 targeting moiety comprises an anti-CD20 Fab and the PD1 agonist moiety comprises a PDL1-based PD1 agonist moiety, the variable heavy or variable light chain of the anti-CD20 Fab and the PDL1-based PD1 agonist moiety are on different polypeptide chains). Exemplary configurations of the CD20-PD1 binding molecules of the disclosure are disclosed, inter alia, in FIGS. 1A-1L, and in numbered embodiments 31 to 106.

A CD20-PD1 binding molecule can be monovalent for a CD20 targeting moiety (i.e., has a single CD20 targeting moiety) or multivalent for a CD20 targeting moiety (i.e., has multiple CD20 targeting moieties). Similarly, a CD20-PD1 binding molecule can be monovalent for a PD1 agonist moiety (i.e., has a single PD1 agonist moiety) or multivalent for a PD1 agonist moiety (i.e., has multiple PD1 agonist moieties). In some embodiments, the CD20-PD1 binding molecule is bivalent for the CD20 targeting moiety (i.e., has two CD20 targeting moieties). When a CD20-PD1 binding molecule is multivalent for a CD20 targeting moiety and/or a PD1 agonist moiety, the multiple CD20 targeting moieties can be the same or different from one another and/or the multiple PD1 agonist moieties can be the same or different from one another.

In some embodiments, a CD20-PD1 binding molecule can include one or more linker sequences connecting the various components of its one or more polypeptide chains, for example (1) the CD20 targeting moiety or a portion thereof (e.g., the heavy or light chain of an anti-CD20 Fab) and the PD1 agonist moiety or a portion thereof (e.g., PDL1 or PDL2) when present on the same polypeptide chain, (2)

a CD20 targeting moiety and a dimerization domain (e.g., an Fc domain), (3) a PD1 agonist moiety and a dimerization domain (e.g., an Fc domain), or (4) any combination of the foregoing. Exemplary linkers are described in Section 6.7.

Most CD20-PD1 binding molecules are multimeric by virtue of association of dimerization moieties configured to associate with one another (e.g., Fc domains). The CD20-PD1 binding molecules may include two, three, four or more polypeptide chains, some associated through dimerization moieties and others through VH-VL interactions. For convenience and descriptive purposes only, the present disclosure generally refers to polypeptides containing a CD20 targeting moiety, a PD1 agonist moiety and/or a dimerization moiety (e.g., a first Fc domain) that is capable of associating with another polypeptide chain containing a CD20 targeting moiety, a PD1 agonist moiety and/or a corresponding dimerization moiety (e.g., a second Fc domain), respectively, as "monomers." Monomers may include one, two, three or more polypeptide chains. For example, in one embodiment, a monomer may be composed of (a) a first polypeptide chain containing an anti-CD20 VH, a PD1 agonist moiety, and an Fc domain and (b) a second polypeptide chain containing a VL capable of pairing with the anti-CD20 VH. In another embodiment, a monomer may be composed of (a) a first polypeptide chain containing a first anti-CD20 VH, a second anti-CD20 VH and an Fc domain, (b) a second polypeptide chain containing a first VL capable of pairing with the first anti-CD20 VH and (c) a third polypeptide chain containing a second VL capable of pairing with the second anti-CD20 VH.

Below are some illustrative examples of monomers of the disclosure, described in an N-to-C terminal orientation. Individual elements of each monomer are described in detail herein, for example in the subsections that follow and the numbered embodiments.

(1) Exemplary Monomer 1: CD20 targeting moiety—optional linker—dimerization moiety (see, e.g., FIGS. 1A, 1E, 1F, 1G, and 1H, left monomers).

(2) Exemplary Monomer 2: PD1 agonist moiety—optional linker—dimerization moiety (see, e.g., FIG. 1A, right monomer).

Figure 1A:
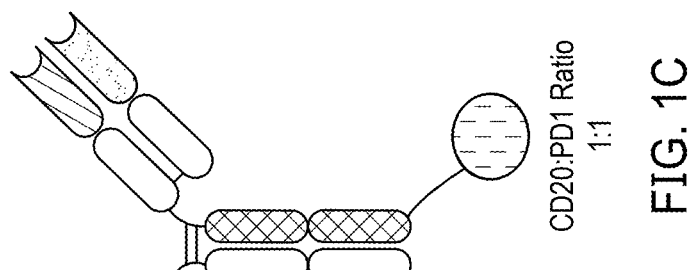
Figure 1B:
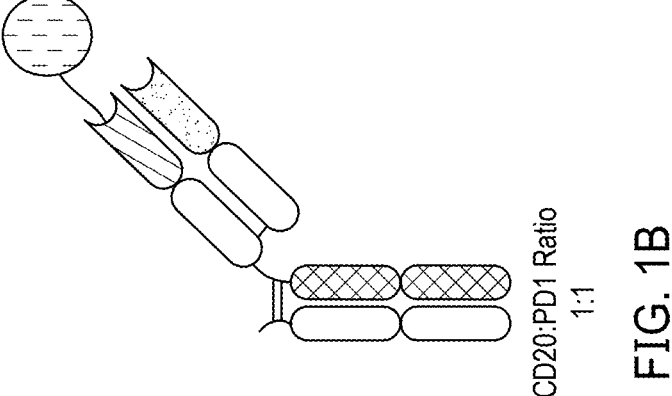
Figure 1C:
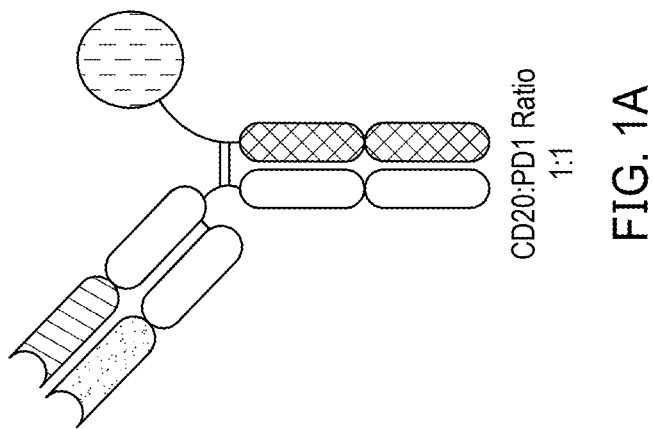
Figure 1D:
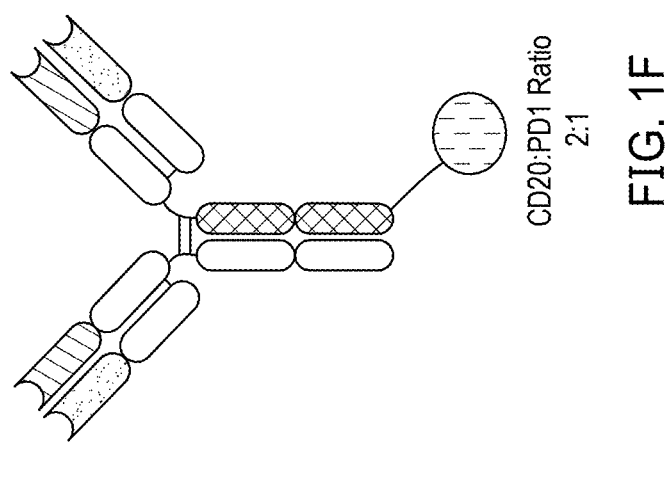

(3) Exemplary Monomer 3: optional linker—dimerization moiety (see, e.g., FIGS. 1B, 1C, and 1D, left monomers).

(4) Exemplary Monomer 4: PD1 agonist moiety—optional linker—CD20 targeting moiety—optional linker—dimerization moiety (see, e.g., FIGS. 1B and 1E, right monomers; FIG. 1I, both monomers).

Figure 1E:
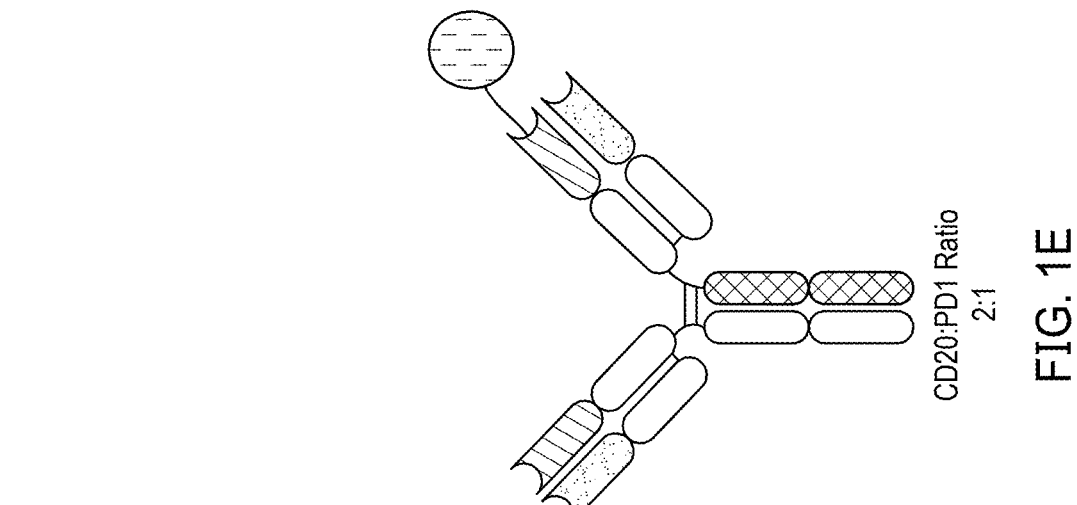
Figure 1F:
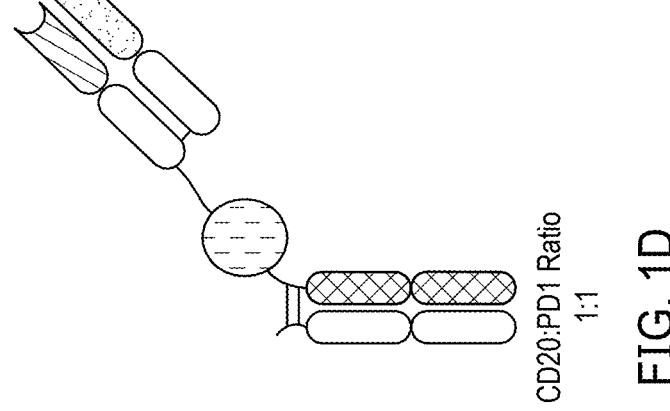
Figure 1I:
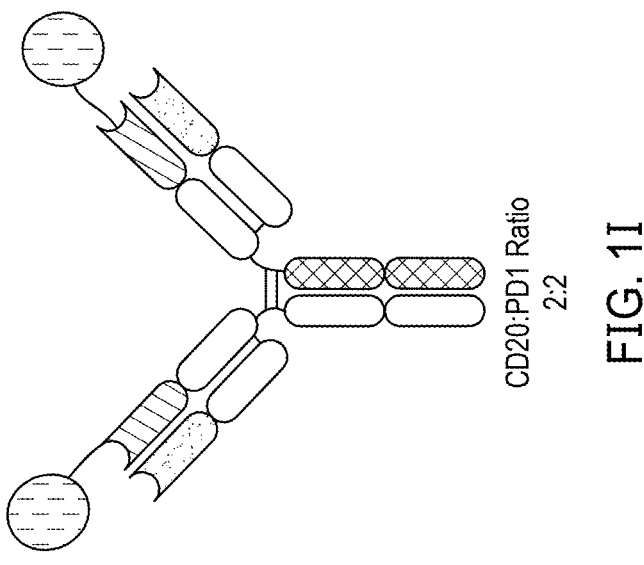
Figure 1H:
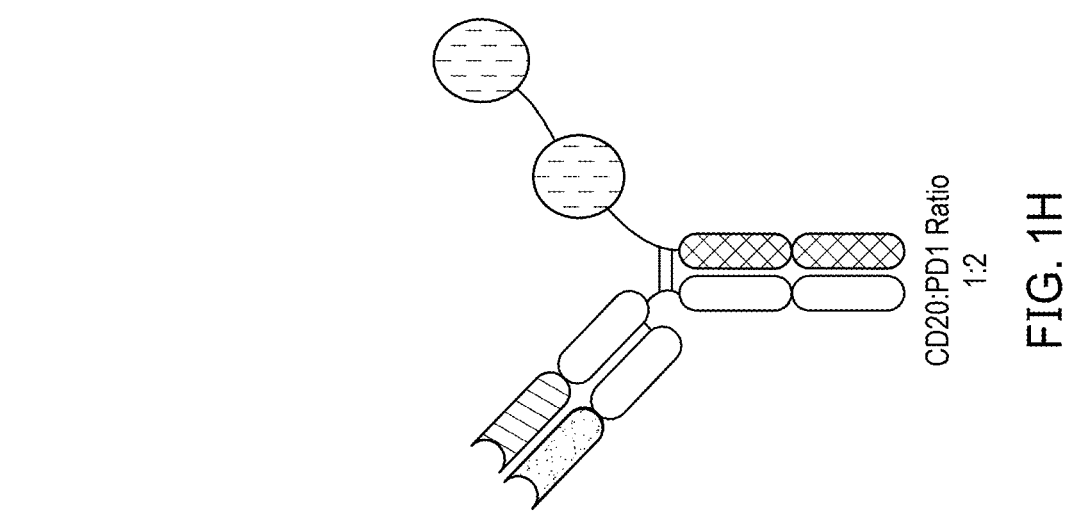
Figure 1G:
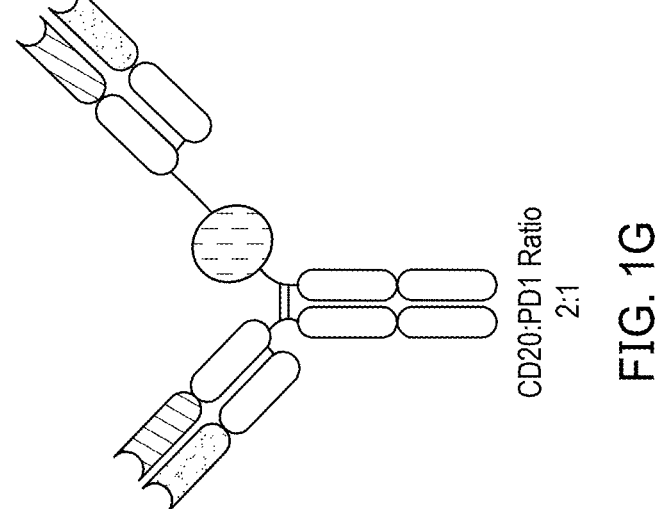
Figure 1L:
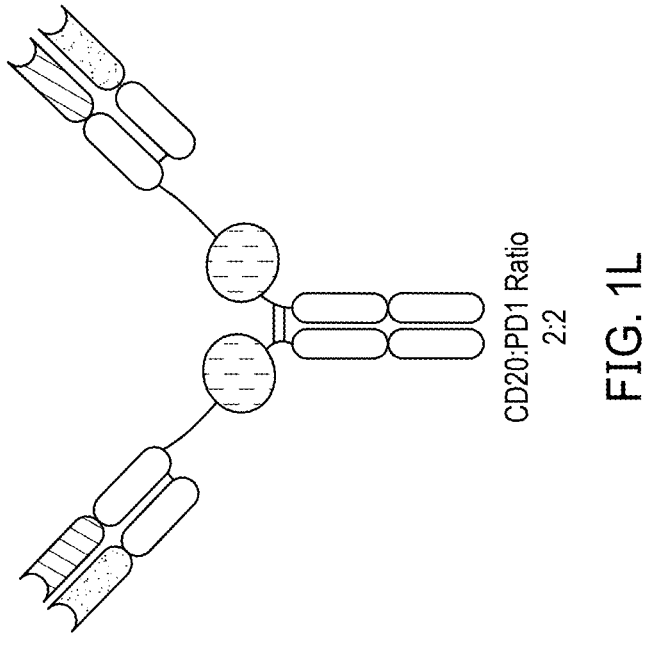

(5) Exemplary Monomer 5: CD20 targeting moiety—optional linker—dimerization moiety—PD1 agonist moiety (see, e.g., FIGS. 1C and 1F, right monomers; FIG. 1J, both monomers).

(6) Exemplary Monomer 6: CD20 targeting moiety—optional linker—PD1 agonist moiety—optional linker—dimerization moiety (see, e.g., FIGS. 1D and 1G, right monomer; FIG. 1L, both monomers).

(7) Exemplary Monomer 7: PD1 agonist moiety—optional linker—PD1 agonist moiety—optional linker—dimerization moiety (see, e.g., FIG. 1H, right monomer).

(8) Exemplary Monomer 8: CD20 targeting moiety—optional linker—dimerization moiety—optional linker—CD20 targeting moiety (see, e.g., FIG. 1K, left monomer).

Figure 1K:
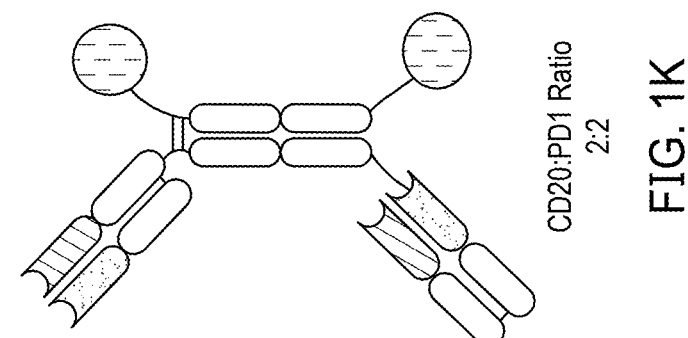
Figure 1J:
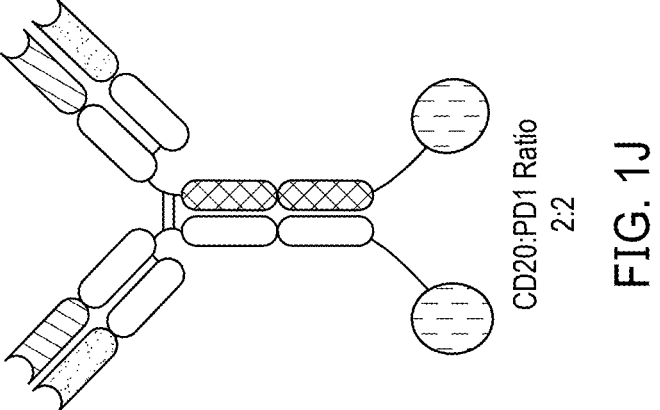

(9) Exemplary Monomer 9:PD1 agonist moiety—optional linker—dimerization moiety—optional linker—PD1 agonist moiety (see, e.g., FIG. 1K, right monomer).

In some embodiments, the present disclosure provides a CD20-PD1 binding molecule comprising Exemplary Monomer 1 and Exemplary Monomer 2 (see, e.g., FIG. 1A).

In some embodiments, the present disclosure provides a CD20-PD1 binding molecule comprising Exemplary Monomer 3 and Exemplary Monomer 4 (see, e.g., FIG. 1B).

In some embodiments, the present disclosure provides a CD20-PD1 binding molecule comprising Exemplary Monomer 3 and Exemplary Monomer 5 (see, e.g., FIG. 1C).

In some embodiments, the present disclosure provides a CD20-PD1 binding molecule comprising Exemplary Monomer 3 and Exemplary Monomer 6 (see, e.g., FIG. 1D).

In some embodiments, the present disclosure provides a CD20-PD1 binding molecule comprising Exemplary Monomer 1 and Exemplary Monomer 4 (see, e.g., FIG. 1E).

In some embodiments, the present disclosure provides a CD20-PD1 binding molecule comprising Exemplary Monomer 1 and Exemplary Monomer 5 (see, e.g., FIG. 1F).

In some embodiments, the present disclosure provides a CD20-PD1 binding molecule comprising Exemplary Monomer 1 and Exemplary Monomer 6 (see, e.g., FIG. 1G).

In some embodiments, the present disclosure provides a CD20-PD1 binding molecule comprising Exemplary Monomer 1 and Exemplary Monomer 7 (see, e.g., FIG. 1H).

In some embodiments, the present disclosure provides a CD20-PD1 binding molecule comprising two monomers according to Exemplary Monomer 4 (see, e.g., FIG. 1I).

In some embodiments, the present disclosure provides a CD20-PD1 binding molecule comprising two monomers according to Exemplary Monomer 5 (see, e.g., FIG. 1J).

In some embodiments, the present disclosure provides a CD20-PD1 binding molecule comprising Exemplary Monomer 8 and Exemplary Monomer 9 (see, e.g., FIG. 1K).

In some embodiments, the present disclosure provides a CD20-PD1 binding molecule comprising two monomers according to Exemplary Monomer 6 (see, e.g., FIG. 1L).

In the CD20-PD1 binding molecules of the disclosure, when the CD20 targeting moiety is an antigen binding domain ("ABD") of an antibody, each monomer can be composed of two or more polypeptide chains, one polypeptide chain bearing the heavy chain variable region and the other polypeptide chain(s) bearing the light chain variable region. The CD20 targeting moiety can comprise heavy and light chain variable domains on separate polypeptide chains. For example, a monomer can be composed of a Polypeptide A and Polypeptide B. Polypeptide A can include, for example, from N-terminus to C-terminus: the heavy chain variable domain of a CD20 targeting moiety—optional linker—PD1 agonist moiety—optional linker—dimerization moiety; and Polypeptide B can comprise the light chain variable domain of the CD20 targeting moiety. Where a monomer is bivalent for the CD20 targeting moiety, the monomer can include a third polypeptide chain (Polypeptide C) comprising another light chain variable domain of the CD20 targeting moiety.

Alternatively, a CD20 targeting moiety can be in the form of an scFv, in which the heavy and light chain variable regions of the CD20 targeting moiety are fused to one another in a single polypeptide.

Further details of the components of the CD20-PD1 binding molecules of the disclosure are presented below.

6.2.1. Biochemical Properties of CD20-PD1 Binding Molecules

In vivo, large complexes of antibodies can be rapidly eliminated by phagocytosis, leading to reduced efficacy of the antibody. Large complexes can also increase immunogenicity of a therapeutic antibody. See, e.g., WO2020047067A1. During manufacturing, aggregation is a common issue that compromises the quality, safety, and efficacy of antibodies. The CD20-PD1 binding molecules of the disclosure can be less prone to aggregation, for example in vivo or ex vivo as compared to parental antibodies from which the CD20 targeting moieties were derived, and/or as compared to other antibody formats comprising a CD20 targeting moiety and a PD1 agonist moiety. Thus, in some embodiments, the CD20-PD1 binding molecules of the disclosure have at least 50%, at least 60%, at least 70%, at least 80%, at least 95%, or at least 99% less aggregation during recombinant production in a mammalian cell line than a parental antibody. As described in Section 7.1.4, the oligomerization state of the CD20-PD1 binding molecules can be determined by, for example, size-exclusion ultra-performance liquid chromatography. Most of the CD20-PD1 binding molecules displayed greater than 85% monomeric species without additional size exclusion chromatography (SEC) (see Section 7.2.2). Column purification can then be employed to further purify monomeric species. For example, the monomer percentage of 2+2 m20_mPL_4 (molecule L of FIG. 2A) was increased to 99% following two column purification, including an SEC step (see Section 7.2.2).

CD20-PD1 binding molecules of the disclosure also demonstrate good thermal stability. High thermostability and low aggregation propensity facilitate antibody manufacturing and storage, and promote long serum half-life. Carter and Merchant, 1997, Curr Opin Biotechnol, 8(4):449-454. Thermal stability can be measured by methods known in the art, including differential scanning fluorimetry (DSF) (see, e.g., Section 7.1.5). All tested CD20-PD1 molecules tested possessed a similar thermal stability as measured by DSF, with a melting temperature 1 (Tm1)—which represents the first unfolding midpoint of the protein—of about 60° C. (see Section 7.2.2).

6.3. The CD20 Targeting Moiety

The incorporation of CD20 targeting moieties in the CD20-PD1 binding molecules of the disclosure provides, in some embodiments, the delivery of high concentrations of localized PD1 agonist moieties for the treatment of autoimmune disorders, including but not limited to type 1 diabetes, systemic lupus erythematosus, and Crohn's disease, as well as for the treatment of graft-versus-host disease (GVHD). In some embodiments, in addition to facilitating the localized delivery of PD1 agonist moieties, an anti-CD20 moiety provides an additional therapeutic pathway against such autoimmune diseases.

In certain embodiments of the disclosure, each CD20 targeting moiety of the CD20-PD1 binding molecules comprises an antigen binding domain of an anti-CD20 antibody. In some embodiments, a CD20-PD1 binding molecule of the disclosure comprises a single CD20 targeting moiety (e.g., a CD20 targeting moiety on a first monomer or on a second monomer in embodiments where CD20-PD1 binding molecule is monovalent for the CD20 targeting moiety). In some embodiments, a CD20-PD1 binding molecule of the disclosure comprises two CD20 targeting moieties (e.g., a first CD20 targeting moiety on a first monomer and a second CD20 targeting moiety on a second monomer in embodiments where the CD20-PD1 binding molecule is bivalent for the CD20 targeting moiety; or both a first and a second CD20 targeting moiety can be on either a first monomer or a second monomer). In such embodiments, the two CD20 targeting moieties can be identical, or they can be different.

When different, the two CD20 targeting moieties can be orthogonal, bind to distinct epitopes of CD20, and/or be non-competing.

In some embodiments, the CD20 targeting moiety comprises an antigen binding domain of a known anti-CD20 antibody. Examples of known anti-CD20 antibodies include, but are not limited to rituximab, ocrelizumab, obinutuzumab, ofatumumab, ibritumomab ituxetan, tositumomab, ublituximab, ocaratuzumab, TRU-015, and veltuzumab (each a "reference CD20 antibody"). In further embodiments, the CD20 targeting moiety comprises CDRs having CDR sequences of a reference CD20 antibody. In some embodiments, the CD20 targeting moiety comprises all 6 CDR sequences of a reference CD20 antibody. In other embodiments, the targeting moiety comprises at least the heavy chain CDR sequences (CDR-H1, CDR-H2, CDR-H3) of a reference CD20 antibody and the light chain CDR sequences of a universal light chain. In further aspects, a CD20 targeting moiety comprises a VH comprising the amino acid sequence of the VH of a reference CD20 antibody. In some embodiments, the CD20 targeting moiety further comprises a VL comprising the amino acid sequence of the VL of the reference CD20 antibody. In other embodiments, the targeting moiety further comprises a universal light chain VL sequence.

In other embodiments, the CD20 targeting moiety comprises an antigen binding domain that binds to the same CD20 epitope as and/or competes for binding to CD20 with rituximab, ocrelizumab, obinutuzumab, ofatumumab, ibritumomab ituxetan, tositumomab, ublituximab, ocaratuzumab, TRU-015, or veltuzumab. Assays for measuring antibody competition are known in the art. For example, a sample of CD20 can be bound to a solid support. Then, a first antibody and a second antibody are added. One of the two antibodies is labelled. If the labelled antibody and the unlabeled antibody bind to separate and discrete sites on CD20, the labelled antibody will bind at the same level whether or not the unlabeled antibody is present. However, if the sites of interaction are identical or overlapping, the unlabeled antibody will compete, and the amount of labelled antibody bound to the antigen will be lowered. If the unlabeled antibody is present in excess, very little, if any, labelled antibody will bind. In some embodiments, a competing antibody is an antibody that decrease the binding of another antibody to CD20 by about 50%, about 60%, about 70%, about 80%, about 85%, about 90%, about 95%, or about 99%. Details of procedures for carrying out such competition assays are well known in the art and can be found, for example, in Greenfield, Ed., Antibodies, A Laboratory Manual, Cold Spring Harbor Laboratory Press, Cold Spring Harbor, New York, 2014. Such assays can be made quantitative by using purified antibodies. A standard curve can be established by titrating one antibody against itself, i.e., the same antibody is used for both the label and the competitor. The capacity of an unlabeled competing antibody to inhibit the binding of the labeled antibody to the plate is titrated. The results can be plotted, and the concentrations necessary to achieve the desired degree of binding inhibition are compared. In some embodiments, competition for binding to a target molecule can be determined, for example, using a real time, label-free bio-layer interferometry assay on the Octet® HTX biosensor platform (Pall ForteBio Corp.).

Suitable CD20 targeting moiety formats are described in Section 6.3.1. The CD20 targeting moiety is preferably a CD20 binding fragment of an anti-CD20 antibody, e.g., a Fab, as described in Section 6.3.1.1, an Fv fragment, or an scFv, as described in Section 6.3.1.2.

The CD20 targeting moiety can be incorporated into a CD20-PD1 binding molecule having any of the configurations described herein. The CD20-PD1 binding molecules are typically composed of a plurality of polypeptide chains, for example as represented by the Exemplary Monomers described in Section 6.2. As set forth in Section 6.2, the CD20 targeting moiety can be incorporated into any one of Exemplary Monomers 1, 4, 5, 6 and 8. Exemplary CD20-PD1 binding molecules that incorporate one or more of Exemplary Monomers 1, 4, 5, 6 and 8 are detailed in Section 6.2.

6.3.1. CD20 Targeting Moiety Formats

In certain aspects, the CD20 targeting moiety can be any type of antibody or fragment thereof that retains specific binding to CD20. In some embodiments, the antigen binding moiety is an immunoglobulin molecule, particularly an IgG class immunoglobulin molecule, more particularly an $IgG_1$ or $IgG_4$ immunoglobulin molecule. Antibody fragments include, but are not limited to, VH (or $V_H$) fragments, VL (or $V_L$) fragments, Fab fragments, $F(ab')_2$ fragments, scFv fragments, Fv fragments, minibodies, diabodies, triabodies, and tetrabodies.

6.3.1.1. Fab

Fab domains were traditionally produced by proteolytic cleavage of immunoglobulin molecules using enzymes such as papain. In the CD20-PD1 binding molecules of the disclosure, the Fab domains are typically recombinantly expressed as part of the CD20-PD1 binding molecule.

The Fab domains can comprise constant domain and variable region sequences from any suitable species, and thus can be murine, chimeric, human or humanized. In some embodiments, variable regions sequences and/or constant domain region sequences are derived from a known anti-CD20 antibody. Examples of known anti-CD20 antibodies include, but are not limited to rituximab, ocrelizumab, obinutuzumab, ofatumumab, ibritumomab ituxetan, tositumomab, ublituximab, ocaratuzumab, TRU-015, and veltuzumab.

In some embodiments, the CD20 targeting moiety comprises a Fab that binds to the same CD20 epitope as and/or competes for binding to CD20 with a Fab of rituximab, ocrelizumab, obinutuzumab, ofatumumab, ibritumomab ituxetan, tositumomab, ublituximab, ocaratuzumab, TRU-015, or veltuzumab (each a "reference CD20 antibody"). In further embodiments, the CD20 targeting moiety comprises CDRs having CDR sequences of a reference CD20 antibody. In some embodiments, the CD20 targeting moiety comprises all 6 CDR sequences of a reference CD20 antibody. In other embodiments, the targeting moiety comprises at least the heavy chain CDR sequences (CDR-H1, CDR-H2, CDR-H3) of a reference CD20 antibody and the light chain CDR sequences of a universal light chain. In further aspects, a CD20 targeting moiety comprises a VH comprising the amino acid sequence of the VH of a reference CD20 antibody. In some embodiments, the CD20 targeting moiety further comprises a VL comprising the amino acid sequence of the VL of the reference CD20 antibody. In other embodiments, the targeting moiety further comprises a universal light chain VL sequence.

Fab domains typically comprise a CH1 domain attached to a VH domain which pairs with a CL domain attached to a VL domain. In a wild-type immunoglobulin, the VH domain is paired with the VL domain to constitute the Fv region, and the CH1 domain is paired with the CL domain to further stabilize the binding module. A disulfide bond between the two constant domains can further stabilize the Fab domain.

For the CD20-PD1 binding molecules of the disclosure, particularly when the light chain is not a common or universal light chain, it is advantageous to use Fab heterodimerization strategies to permit the correct association of Fab domains belonging to the same ABD and minimize aberrant pairing of Fab domains belonging to different ABDs. For example, the Fab heterodimerization strategies shown in Table 1 below can be used:

TABLE 1

| | | Fab Heterodimerization Strategies | | | |
|---|---|---|---|---|---|
| STRATEGY | VH | CH1 | VL | CL | REFERENCE |
| CrossMabCH1-CL (a type of "domain exchange") | WT | CL domain | WT | CH1 domain | Schaefer et al., 2011, Cancer Cell 2011; 20: 472-86; PMID: 22014573. |
| orthogonal Fab VHVRD1CH1CRD2-VLVRD1CλCRD2 | 39K, 62E | H172A, F174G | 1R, 38D, (36F) | L135Y, S176W | Lewis et al., 2014, Nat Biotechnol 32: 191-8 |
| orthogonal Fab VHVRD2CH1wt-VLVRD2Cλwt | 39Y | WT | 38R | WT | Lewis et al., 2014, Nat Biotechnol 32: 191-8 |
| TCR CαCβ | 39K | TCR Cα | 38D | TCR Cβ | Wu et al., 2015, MAb s7: 364-76 |
| CR3 | WT | T192E | WT | N137K, S114A | Golay et al., 2016, J Immunol 196: 3199-211. |
| MUT4 | WT | L143Q, S188V | WT | V133T, S176V | Golay at al., 2016, J Immunol 196: 3199-211. |
| DuetMab | WT | F126C | WT | S121C | Mazor et al., 2015, MAbs 7: 377-89; Mazor et al., 2015, MAbs 7: 461-669. |

TABLE 1-continued

| | | Fab Heterodimerization Strategies | | | |
|---|---|---|---|---|---|
| STRATEGY | VH | CH1 | VL | CL | REFERENCE |
| Domain exchanged | WT | CH3 + knob or hole mutation | WT | CH3 + hole or knob mutation | Wozniak-Knopp et al., 2018, PLoSONE13(4): e0195442 |

Accordingly, in certain embodiments, correct association between the two polypeptides of a Fab is promoted by exchanging the VL and VH domains of the Fab for each other or exchanging the CH1 and CL domains for each other, e.g., as described in WO 2009/080251.

Correct Fab pairing can also be promoted by introducing one or more amino acid modifications in the CH1 domain and one or more amino acid modifications in the CL domain of the Fab and/or one or more amino acid modifications in the VH domain and one or more amino acid modifications in the VL domain. The amino acids that are modified are typically part of the VH:VL and CH1:CL interface such that the Fab components preferentially pair with each other rather than with components of other Fabs.

In one embodiment, the one or more amino acid modifications are limited to the conserved framework residues of the variable (VH, VL) and constant (CH1, CL) domains as indicated by the Kabat numbering of residues. Almagro, 2008, Frontiers In Bioscience 13:1619-1633 provides a definition of the framework residues on the basis of Kabat, Chothia, and IMGT numbering schemes.

In one embodiment, the modifications introduced in the VH and CH1 and/or VL and CL domains are complementary to each other. Complementarity at the heavy and light chain interface can be achieved on the basis of steric and hydrophobic contacts, electrostatic/charge interactions or a combination of the variety of interactions. The complementarity between protein surfaces is broadly described in the literature in terms of lock and key fit, knob into hole, protrusion and cavity, donor and acceptor etc., all implying the nature of structural and chemical match between the two interacting surfaces.

In one embodiment, the one or more introduced modifications introduce a new hydrogen bond across the interface of the Fab components. In one embodiment, the one or more introduced modifications introduce a new salt bridge across the interface of the Fab components. Exemplary substitutions are described in WO 2014/150973 and WO 2014/082179, the contents of which are hereby incorporated by reference.

In some embodiments, the Fab domain comprises a 192E substitution in the CH1 domain and 114A and 137K substitutions in the CL domain, which introduces a salt-bridge between the CH1 and CL domains (see, e.g., Golay et al., 2016, J Immunol 196:3199-211).

In some embodiments, the Fab domain comprises a 143Q and 188V substitutions in the CH1 domain and 113T and 176V substitutions in the CL domain, which serves to swap hydrophobic and polar regions of contact between the CH1 and CL domain (see, e.g., Golay et al., 2016, J Immunol 196:3199-211).

In some embodiments, the Fab domain can comprise modifications in some or all of the VH, CH1, VL, CL domains to introduce orthogonal Fab interfaces which promote correct assembly of Fab domains (Lewis et al., 2014 Nature Biotechnology 32:191-198). In an embodiment, 39K, 62E modifications are introduced in the VH domain, H172A, F174G modifications are introduced in the CH1 domain, 1 R, 38D, (36F) modifications are introduced in the VL domain, and L135Y, S176W modifications are introduced in the CL domain. In another embodiment, a 39Y modification is introduced in the VH domain and a 38R modification is introduced in the VL domain.

Fab domains can also be modified to replace the native CH1:CL disulfide bond with an engineered disulfide bond, thereby increasing the efficiency of Fab component pairing. For example, an engineered disulfide bond can be introduced by introducing a 126C in the CH1 domain and a 121 C in the CL domain (see, e.g., Mazor et al., 2015, MAbs 7:377-89).

Fab domains can also be modified by replacing the CH1 domain and CL domain with alternative domains that promote correct assembly. For example, Wu et al., 2015, MAbs 7:364-76, describes substituting the CH1 domain with the constant domain of the T cell receptor and substituting the CL domain with the b domain of the T cell receptor, and pairing these domain replacements with an additional charge-charge interaction between the VL and VH domains by introducing a 38D modification in the VL domain and a 39K modification in the VH domain.

In lieu of, or in addition to, the use of Fab heterodimerization strategies to promote correct VH-VL pairings, the VL of common light chain (also referred to as a universal light chain) can be used for each Fab VL region of a CD20-PD1 binding molecule of the disclosure. In various embodiments, employing a common light chain as described herein reduces the number of inappropriate species of CD20-PD1 binding molecules as compared to employing original cognate VLs. In various embodiments, the VL domains of the CD20-PD1 binding molecules are identified from monospecific antibodies comprising a common light chain. In various embodiments, the VH regions of the CD20-PD1 binding molecules comprise human heavy chain variable gene segments that are rearranged in vivo within mouse B cells that have been previously engineered to express a limited human light chain repertoire, or a single human light chain, cognate with human heavy chains and, in response to exposure with an antigen of interest, generate an antibody repertoire containing a plurality of human VHs that are cognate with one or one of two possible human VLs, wherein the antibody repertoire specific for the antigen of interest. Common light chains are those derived from a rearranged human Vκ1-39Jκ5 sequence or a rearranged human Vκ3-20Jκ1 sequence, and include somatically mutated (e.g., affinity matured) versions. See, for example, U.S. Pat. No. 10,412, 940.

6.3.1.2. scFv

Single chain Fv or "scFv" antibody fragments comprise the VH and VL domains of an antibody in a single polypeptide chain, are capable of being expressed as a single chain polypeptide, and retain the specificity of the intact antibodies from which they are derived. Generally, the scFv polypeptide further comprises a polypeptide linker between the VH and VL domain that enables the scFv to form the desired structure for target binding. Examples of linkers suitable for connecting the VH and VL chains of an scFv are the linkers identified in Section 6.7.

Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The scFv can comprise VH and VL sequences from any suitable species, such as murine, human or humanized VH and VL sequences. In some embodiments, the scFv can comprise VH and VL sequences from a known anti-CD20 antibody. Examples of known anti-CD20 antibodies include, but are not limited to rituximab, ocrelizumab, obinutuzumab, ofatumumab, ibritumomab ituxetan, tositumomab, ublituximab, ocaratuzumab, TRU-015, and veltuzumab.

In some embodiments, the CD20 targeting moiety comprises an scFv that binds to the same CD20 epitope as and/or competes for binding to CD20 with an scFv derived from rituximab, ocrelizumab, obinutuzumab, ofatumumab, ibritumomab ituxetan, tositumomab, ublituximab, ocaratuzumab, TRU-015, or veltuzumab.

To create an scFv-encoding nucleic acid, the VH and VL-encoding DNA fragments are operably linked to another fragment encoding a linker, e.g., encoding any of the linkers described in Section 6.7 (typically a repeat of a sequence containing the amino acids glycine and serine, such as the amino acid sequence (Gly4~Ser)$_3$ (SEQ ID NO: 1), such that the VH and VL sequences can be expressed as a contiguous single-chain protein, with the VL and VH regions joined by the flexible linker (see, e.g., Bird et al., 1988, Science 242:423-426; Huston et al., 1988, Proc. Natl. Acad. Sci. USA 85:5879-5883; McCafferty et al., 1990, Nature 348: 552-554).

6.4. PD1 Agonist Moiety

In certain embodiments of the disclosure, the PD1 agonist moiety of the CD20-PD1 binding molecules comprises a wild type or variant PD1-binding domain of programmed death-ligand 1 (PDL1) or programmed death-ligand 2 (PDL2). In some embodiments, a CD20-PD1 binding molecule of the disclosure comprises a single PD1 agonist moiety (e.g., a PD1 agonist moiety on a first monomer or on a second monomer in embodiments where the CD20-PD1 binding molecule is monovalent for the PD1 agonist moiety). In some embodiments, a CD20-PD1 binding molecule of the disclosure comprises two PD1 agonist moieties (e.g. a first PD1 agonist moiety on a first monomer and a second PD1 agonist moiety on a second monomer, or both first and second PD1 agonist moieties on either a first monomer or a second monomer). In such embodiments, the two PD1 agonist moieties can be identical, or they can be different. When different, the two PD1 agonist moieties can interact with PD1 differentially (e.g., with different affinities).

The PD1 agonist moiety can be incorporated into a CD20-PD1 binding molecule having any of the configurations described herein. The CD20-PD1 binding molecules are typically composed of a plurality of polypeptide chains, for example as represented by the Exemplary Monomers described in Section 6.2. As set forth in Section 6.2, the PD1 agonist moiety can be incorporated into any one of Exemplary Monomers 2, 4, 5, 6, 7 and 9. Exemplary CD20-PD1 binding molecules that incorporate one or more of Exemplary Monomers 2, 4, 5, 6, 7 and 9 are detailed in Section 6.2. In some embodiments, the PD1 agonist moiety is a PDL1-based agonist moiety. In other embodiments, the PD1 agonist moisty is a PDL2-based agonist moiety.

6.4.1. PDL1-Based PD1 Agonist Moieties

PDL1 plays a critical role in induction and maintenance of immune tolerance to self. As a ligand for the inhibitor receptor PD1, PDL1 modulates the activation threshold of T-cells and limits T-cell effector response. The present disclosure provides CD20-PD1 binding molecules in which at least one PD1 agonist moiety comprises an amino acid sequence comprising or homologous to a PDL1 amino acid sequence as described herein. Such PD1 agonist moieties are referred to herein as "PDL1-based PD1 agonist moieties" or like terms.

The human PDL1 protein is synthesized as a precursor polypeptide of 290 amino acids, from which 18 amino acids are removed to generate mature hPDL1, with amino acids 19-238 (numbering based on the precursor protein) forming the hPDL1 extracellular domain, or ectodomain. The sequence of human PDL1 has the Uniprot identifier Q9NZQ7 (uniprot.org/uniprot/Q9NZQ7). The sequence of murine PDL1 has the Uniprot identifier Q9EP73 (uniprot.org/uniprot/Q9EP73).

The precursor human PDL1 polypeptide has the following amino acid sequence (signal sequence=underlined; extracellular domain=bold):

```
                                      (SEQ ID NO: 2)
MRIFAVFIFMTYWHLLNAFTVTVPKDLYVVEYGSNMTIECKFPVEKQLD

LAALIVYWEMEDKNIIQFVHGEEDLKVQHSSYRQRARLLKDQLSLGNAA

LQITDVKLQDAGVYRCMISYGGADYKRITVKVNAPYNKINQRILWDPVT

SEHELTCQAEGYPKAEVIWTSSDHQVLSGKTTTTNSKREEKLFNVTSTL

RINTTTNEIFYCTFRRLDPEENHTAELVIPELPLAHPPNERTHLVILGA

ILLCLGVALTFIFRLRKGRMMDVKKCGIQDTNSKKQSDTHLEET.
```

The murine PDL1 polypeptide is synthesized as a precursor polypeptide of 290 amino acids, from which 18 amino acids are removed to generate mature mPDL1. Amino acids 19-239 (numbering based on the precursor protein) form the mPDL1 extracellular domain, or ectodomain. The precursor murine PDL1 polypeptide has the following amino acid sequence (signal sequence=underlined; extracellular domain=bold):

```
                                      (SEQ ID NO: 3)
MRIFAGIIFTACCHLLRAFTITAPKDLYVVEYGSNVTMECRFPVERELD

LLALVVYWEKEDEQVIQFVAGEEDLKPQHSNFRGRASLPKDQLLKGNAA

LQITDVKLQDAGVYCCIISYGGADYKRITLKVNAPYRKINQRISVDPAT

SEHELICQAEGYPEAEVIWTNSDHQPVSGKRSVTTSRTEGMLLNVTSSL

RVNATANDVFYCTFWRSQPGQNHTAELIIPELPATHPPQNRTHWVLLGS

ILLFLIVVSTVLLFLRKQVRMLDVEKCGVEDTSSKNRNDTQFEET
```

In some embodiments, a PD1 agonist moiety is a PDL1-based agonist moiety comprising an amino acid sequence comprising at least 70% sequence identity, e.g., at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity, or 100% sequence identity, to a PD1-binding portion of a mammalian, e.g., human or murine, PDL1, or the entire ectodomain of a mammalian, e.g., human or murine, PDL1. In certain aspects, the PD1-binding portion of PDL1 comprises the IgV domain of human or mouse PDL1. In certain embodiments, the PD1-binding portion of PDL1 comprises amino acids 19-134 of human PDL1 or amino acids 19-134 of murine PDL1.

In certain embodiments, a PDL1-based PD1 agonist moiety comprises an amino acid sequence having at least 70% (e.g., at least 80%, at least 90%, at least 95%, at least 97%, at least 98% or at least 99%) sequence identity to the ectodomain of PDL1 or a PD1-binding portion thereof and one or more amino acid substitutions as compared to wild type PDL1. In some embodiments, the one or more amino acid substitutions increase the stability of the PDL1-based PD1 agonist moiety. For example, in some embodiments, mPDL1 comprises the amino acid substitution C113S (numbering based on the precursor protein).

In some embodiments, the PDL1-based PD1 agonist moiety is fused, either directly or indirectly, to a CD20 targeting moiety, optionally via a linker (e.g., as described in Section 6.7). When present on the same monomer, the PDL1-based PD1 agonist moiety can be N-terminal or C-terminal to the CD20 targeting moiety. When the PDL1-based PD1 agonist moiety is "directly" fused to the CD20 targeting moiety, the PDL1-based PD1 agonist moiety and the CD20 targeting moiety are positioned adjacently on the same monomer, separated only by a linker, if present. When the PDL1-based PD1 agonist moiety is "indirectly" fused to the CD20 targeting moiety, the PDL1-based PD1 agonist moiety and the CD20 targeting moiety are separated by one or more other domains (e.g., a dimerization moiety) on the same monomer, or are located on separate monomers.

6.4.2. PDL2-Based PD1 Agonist Moieties

Interaction of PDL2 with PD1 inhibits T-cell proliferation by blocking cell cycle progression and cytokine production. The present disclosure provides CD20-PD1 binding molecules in which at least one PD1 agonist moiety comprises an amino acid sequence comprising or homologous to a PDL2 amino acid sequence described herein. Such PD1 agonist moieties are referred to herein as "PDL2-based PD1 agonist moieties" or like terms.

The human PDL2 protein is synthesized as a precursor polypeptide of 273 amino acids, from which 19 amino acids are removed to generate mature hPDL2, with amino acids 20-220 (numbering based on the precursor protein) forming the hPDL2 extracellular domain, or ectodomain. The sequence of human PDL2 has the Uniprot identifier Q9BQ51 (uniprot.org/uniprot/Q9BQ51). The sequence of murine PDL2 has the Uniprot identifier Q9WUL5 (uniprot.org/uniprot/Q9WUL5).

The precursor human PDL2 polypeptide has the following amino acid sequence (signal sequence=underlined; extracellular domain=bold):

```
                                    (SEQ ID NO: 4)
MIFLLLMLSLELQLHQIAALFTVTVPKELYIIEHGSNVTLECNFDTGSH

VNLGAITASLQKVENDTSPHRERATLLEEQLPLGKASFHIPQVQVRDEG

QYQCIIIYGVAWDYKYLTLKVKASYRKINTHILKVPETDEVELTCQATG
```

```
-continued
YPLAEVSWPNVSVPANTSHSRTPEGLYQVTSVLRLKPPPGRNFSCVFWN

THVRELTLASIDLQSQMEPRTHPTWLLHIFIPFCIIAFIFIATVIALRK

QLCQKLYSSKDTTKRPVTTTKREVNSAI.
```

The murine PDL2 polypeptide is synthesized as a precursor polypeptide of 247 amino acids, from which 19 amino acids are removed to generate mature mPDL2. Amino acids 20-221 (numbering based on the precursor protein) form the mPDL2 extracellular domain, or ectodomain. The precursor murine PDL2 polypeptide has the following amino acid sequence (signal sequence=underlined; extracellular domain=bold):

```
                                    (SEQ ID NO: 5)
MLLLLPILNLSLQLHPVAALFTVTAPKEVYTVDVGSSVSLECDFDRREC

TELEGIRASLQKVENDTSLQSERATLLEEQLPLGKALFHIPSVQVRDSG

QYRCLVICGAAWDYKYLTVKVKASYMRIDTRILEVPGTGEVQLTCQARG

YPLAEVSWQNVSVPANTSHIRTPEGLYQVTSVLRLKPQPSRNFSCMFWN

AHMKELTSAIIDPLSRMEPKVPRTWPLHVFIPACTIALIFLAIVIIQRK

RI.
```

In some embodiments, a PD1 agonist moiety is a PDL2-based agonist moiety comprising an amino acid sequence comprising least 70% sequence identity, e.g., at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity, or 100% sequence identity, to a PD1-binding portion of a mammalian, e.g., human or murine, PDL2, or the entire ectodomain of a mammalian, e.g., human or murine, PDL1. In certain aspects, the PD1-binding portion of PDL2 comprises the IgV domain of human or mouse PDL2. In certain embodiments, the PD1-binding portion of PDL2 comprises amino acids 20-121 of human PDL2 or amino acids 20-121 of murine PDL2.

In certain embodiments, a PDL2-based PD1 agonist moiety comprises an amino acid sequence having at least 70% (e.g., at least 80%, at least 90%, at least 95%, at least 97%, at least 98% or at least 99%) sequence identity to the ectodomain of PDL2 or a PD1-binding portion thereof and one or more amino acid substitutions as compared to wild type PDL2.

In some embodiments, the PDL2-based PD1 agonist moiety is fused, either directly or indirectly, to a CD20 targeting moiety, optionally via a linker (e.g., as described in Section 6.7). When present on the same monomer, the PDL2-based PD1 agonist moiety can be N-terminal or C-terminal to the CD20 targeting moiety. When the PDL2-based PD1 agonist moiety is "directly" fused to the CD20 targeting moiety, the PDL2-based PD1 agonist moiety and the CD20 targeting moiety are positioned adjacently on the same monomer, separated only by a linker, if present. When the PDL2-based PD1 agonist moiety is "indirectly" fused to the CD20 targeting moiety, the PDL2-based PD1 agonist moiety and the CD20 targeting moiety are separated by one or more other domains (e.g., a dimerization moiety) on the same monomer, or are located on separate monomers.

6.5. The Dimerization Moiety

6.5.1. Fc Domains

In some embodiments, the CD20-PD1 binding molecules and CD20-PD1 monomers of the disclosure include one or more dimerization moieties, for example one or more dimerization moieties that are or comprise an Fc domain. In certain embodiments, a CD20-PD1 monomer of the disclosure comprises a single dimerization moiety (e.g., a single Fc domain) and/or a CD20-PD1 binding molecule of the disclosure comprises two dimerization moieties (e.g., two Fc domains that can associate to form an Fc region).

The CD20-PD1 binding molecules and CD20-PD1 monomers of the disclosure can include an Fc domain, or a pair of Fc domains that associate to form an Fc region, derived from any suitable species and operably linked to a CD20 targeting moiety and/or a PD1 agonist moiety. In one embodiment the Fc domain is derived from a human Fc domain. In preferred embodiments, Fc domain is derived from a human IgG Fc domain.

The CD20 targeting moiety and/or the PD1 agonist moiety may be fused to the N-terminus or the C-terminus of the IgG Fc domain.

One embodiment of the present disclosure is directed to a dimer comprising two Fc-fusion polypeptides created by fusing one or more CD20 targeting moieties and/or PD1 agonist moieties to an Fc domain, e.g., by fusing both a CD20 targeting moiety and a PD1 agonist moiety to an Fc domain that can, upon expression, form a CD20-PD1 monomer capable of homodimerization, or by fusing one or more CD20 targeting moieties and/or one or more PD1 agonist moieties to a first Fc domain and one or more CD20 targeting moieties and/or one or more PD1 agonist moieties to a second Fc domain which upon expression form two different CD20-PD1 monomers that are capable of heterodimerizing. The dimer can be made by, for example, by inserting a gene fusion encoding the fusion protein(s) into an appropriate expression vector, expressing the gene fusion(s) in host cells transformed with the recombinant expression vector, and allowing the expressed fusion protein(s) to assemble much like antibody molecules, whereupon interchain bonds form between the Fc moieties to yield the dimer.

The Fc domains that can be incorporated into CD20-PD1 monomers can be derived from any suitable class of antibody, including IgA (including subclasses IgA1 and IgA2), IgD, IgE, IgG (including subclasses IgG1, IgG2, IgG3 and IgG4), and IgM. In one embodiment, the Fc domain is derived from IgG1, IgG2, IgG3 or IgG4. In some embodiments the Fc domain is derived from IgG1. In some embodiments the Fc domain is derived from IgG4.

The two Fc domains within the Fc region can be the same or different from one another. In a native antibody the Fc domains are typically identical, but for the purpose of producing multispecific binding molecules, e.g., the CD20-PD1 binding molecules of the disclosure, the Fc domains might advantageously be different to allow for heterodimerization, as described in Section 6.5.1 below.

In native antibodies, the heavy chain Fc domain of IgA, IgD and IgG is composed of two heavy chain constant domains (CH2 and CH3) and that of IgE and IgM is composed of three heavy chain constant domains (CH2, CH3 and CH4). These dimerize to create an Fc region.

In CD20-PD1 binding molecules of the present disclosure, the Fc region, and/or the Fc domains within it, can comprise heavy chain constant domains from one or more different classes of antibody, for example one, two or three different classes.

In one embodiment the Fc region comprises CH2 and CH3 domains derived from IgG1.

In one embodiment the Fc region comprises CH2 and CH3 domains derived from IgG2.

In one embodiment the Fc region comprises CH2 and CH3 domains derived from IgG3.

In one embodiment the Fc region comprises CH2 and CH3 domains derived from IgG4.

In one embodiment the Fc region comprises a CH4 domain from IgM. The IgM CH4 domain is typically located at the C-terminus of the CH3 domain.

In one embodiment the Fc region comprises CH2 and CH3 domains derived from IgG and a CH4 domain derived from IgM.

It will be appreciated that the heavy chain constant domains for use in producing an Fc region for the CD20-PD1 binding molecules of the present disclosure may include variants of the naturally occurring constant domains described above. Such variants may comprise one or more amino acid variations compared to wild type constant domains. In one example the Fc region of the present disclosure comprises at least one constant domain that varies in sequence from the wild type constant domain. It will be appreciated that the variant constant domains may be longer or shorter than the wild type constant domain. Preferably the variant constant domains are at least 60% identical or similar to a wild type constant domain. In another example the variant constant domains are at least 70% identical or similar. In another example the variant constant domains are at least 80% identical or similar. In another example the variant constant domains are at least 90% identical or similar. In another example the variant constant domains are at least 95% identical or similar.

IgM and IgA occur naturally in humans as covalent multimers of the common H2L2 antibody unit. IgM occurs as a pentamer when it has incorporated a J-chain, or as a hexamer when it lacks a J-chain. IgA occurs as monomer and dimer forms. The heavy chains of IgM and IgA possess an 18 amino acid extension to the C-terminal constant domain, known as a tailpiece. The tailpiece includes a cysteine residue that forms a disulfide bond between heavy chains in the polymer, and is believed to have an important role in polymerization. The tailpiece also contains a glycosylation site. In certain embodiments, the CD20-PD1 binding molecules of the present disclosure do not comprise a tailpiece.

The Fc domains that are incorporated into the CD20-PD1 binding molecules of the present disclosure may comprise one or more modifications that alter the functional properties of the proteins, for example, binding to Fc-receptors such as FcRn or leukocyte receptors, binding to complement, modified disulfide bond architecture, or altered glycosylation patterns. Exemplary Fc modifications that alter effector function are described in Section 6.5.1.1.

The Fc domains can also be altered to include modifications that improve manufacturability of asymmetric CD20-PD1 binding molecules, for example by allowing heterodimerization, which is the preferential pairing of non-identical Fc domains over identical Fc domains. Heterodimerization permits the production of CD20-PD1 binding molecules in which different polypeptide components are connected to one another by an Fc region containing Fc domains that differ in sequence. Examples of heterodimerization strategies are exemplified in Section 6.5.1.2.

It will be appreciated that any of the modifications mentioned above can be combined in any suitable manner to achieve the desired functional properties and/or combined with other modifications to alter the properties of the CD20-PD1 binding molecules.

6.5.1.1. Fc Domains with Altered Effector Function

In some embodiments, the Fc domain comprises one or more amino acid substitutions that reduces binding to an Fc receptor and/or effector function.

In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of complement dependent cytotoxicity (CDC), antibody-dependent cell-mediated cytotoxicity (ADCC), antibody-dependent cellular phagocytosis (ADCP), and cytokine secretion. In a particular embodiment, the effector function is ADCC.

In one embodiment, the Fc domain (e.g., an Fc domain of a CD20-PD1 monomer) or the Fc region (e.g., one or both Fc domains of a CD20-PD1 binding molecule that can associate to form an Fc region) comprises an amino acid substitution at a position selected from the group of E233, L234, L235, G237, N297, A330, P331, and P329 (numberings according to Kabat EU index). In a more specific embodiment, the Fc domain or the Fc region comprises an amino acid substitution at a position selected from the group of L234, L235 and P329 (numberings according to Kabat EU index). In some embodiments, the Fc domain or the Fc region comprises the amino acid substitutions L234A and L235A (numberings according to Kabat EU index). In one such embodiment, the Fc domain or region is an Igd Fc domain or region, particularly a human Igd Fc domain or region. In one embodiment, the Fc domain or the Fc region comprises an amino acid substitution at position P329. In a more specific embodiment, the amino acid substitution is P329A or P329G, particularly P329G (numberings according to Kabat EU index). In one embodiment, the Fc domain or the Fc region comprises an amino acid substitution at position P329 and a further amino acid substitution at a position selected from E233, L234, L235, N297 and P331 (numberings according to Kabat EU index). In a more specific embodiment, the further amino acid substitution is E233P, L234A, L235A, L235E, N297A, N297D or P331S. In particular embodiments, the Fc domain or the Fc region comprises amino acid substitutions at positions P329, L234 and L235 (numberings according to Kabat EU index). In more particular embodiments, the Fc domain comprises the amino acid mutations L234A, L235A and P329G ("P329G LALA", "PGLALA" or "LALAPG").

In some embodiments, the Fc domain or the Fc region comprises the amino acid substitutions at positions L234, L235, G237, A330, and P331 (numberings according to Kabat EU index). In a more specific embodiment, the amino acid substitutions are L234A, L235E, G237A, A330S, and P331S (numberings according to Kabat EU index).

Typically, the same one or more amino acid substitution is present in each of the two Fc domains of an Fc region. Thus, in a particular embodiment, each Fc domain of the Fc region comprises the amino acid substitutions L234A, L235A and P329G (Kabat EU index numbering), i.e. in each of the first and the second Fc domains in the Fc region the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index). In another particular embodiment, each Fc domain of the Fc region comprises the amino acid substitutions L234A, L235E, G237A, A330S, and P331S (numberings according to Kabat EU index), i.e. in each of the first and the second Fc domains in the Fc region the leucine residue at position 234 is replaced with an alanine residue (L234A), the leucine residue at position 235 is replaced with an alanine residue (L235A), the glycine residue at position 237 is replace with an alanine residue (G237A), the alanine residue at position 330 is replaced with a serine residue (A330S), and the proline residue at position 331 is replaced with a serine residue (P331S) (numbering according to Kabat EU index).

In one embodiment, the Fc domain is an IgG1 Fc domain, for example a human IgG1 Fc domain. In some embodiments, the IgG1 Fc domain is a variant IgG1 comprising D265A and N297A mutations (EU numbering) to reduce effector function. In other embodiments the IgG1 Fc domain is a variant IgG1 comprising L234A, L235E, G237A, A330S, and P331S mutations (numberings according to Kabat EU index), providing for an effector null IgG1 (IgG1EN). Amino acid substitutions L234A, L235E, and G237A reduce binding to FcγRI, FcγRIIa, and FcγRIII, while substitutions A330S and P331S reduce C1q-mediated complement fixation.

In another embodiment, the Fc domain is an IgG4 Fc domain with reduced binding to Fc receptors. Exemplary IgG4 Fc domains with reduced binding to Fc receptors may comprise an amino acid sequence selected from Table 2 below: In some embodiments, the Fc domain includes only the bolded portion of the sequences shown below:

TABLE 2

| Exemplary IgG4 Fc domains with reduced binding to Fc |
| --- |

| Fc Domain | Sequence |
| --- | --- |
| SEQ ID NO: 1 of WO2014/121087 | Asp Lys Arg Val Glu Ser Lys Tyr Gly Pro Cys Pro Pro Cys<br>Pro Ala Pro Pro Val Ala Gly Pro Ser Val Phe Leu Phe Pro<br>Pro Lys Pro Lys Asp Thr Leu Met Ile Ser Arg Thr Pro Glu<br>Val Thr Cys Val Val Val Asp Val Ser Gln Glu Asp Pro Glu<br>Val Gln Phe Asn Trp Tyr Val Asp Gly Val Glu Val His Asn<br>Ala Lys Thr Lys Pro Arg Glu Glu Gln Phe Asn Ser Thr Tyr<br>Arg Val Val Ser Val Leu Thr Val Leu His Gln Asp Trp Leu<br>Asn Gly Lys Glu Tyr Lys Cys Lys Val Ser Asn Lys Gly Leu<br>Pro Ser Ser Ile Glu Lys Thr Ile Ser Lys Ala Lys Gly Gln Pro<br>Arg Glu Pro Gln Val Tyr Thr Leu Pro Pro Ser Gln Glu Glu<br>Met Thr Lys Asn Gln Val Ser Leu Thr Cys Leu Val Lys Gly<br>Phe Tyr Pro Ser Asp Ile Ala Val Glu Trp Glu Ser Asn Gly<br>Gln Pro Glu Asn Asn Tyr Lys Thr Thr Pro Pro Val Leu Asp<br>Ser Asp Gly Ser Phe Phe Leu Tyr Ser Arg Leu Thr Val Asp<br>Lys Ser Arg Trp Gln Glu Gly Asn Val Phe Ser Cys Ser Val |

TABLE 2-continued

<u>Exemplary IgG4 Fc domains with reduced binding to Fc</u>

| Fc Domain | Sequence |
| --- | --- |

Met His Glu Ala Leu His Asn His Tyr Thr Gln Lys Ser Leu
Ser Leu Ser Leu Gly Lys (SEQ ID NO: 6)

SEQ ID NO: 2 of
WO2014/121087

Asp Lys Lys Val Glu Pro Lys Ser Cys Asp Lys Thr His Thr
Cys Pro Pro Cys Pro Ala Pro Val Ala Gly Pro Ser Val
Phe Leu Phe Pro Pro Lys Pro Lys Asp Thr Leu Met Ile Ser
Arg Thr Pro Glu Val Thr Cys Val Val Val Asp Val Ser Gln
Glu Asp Pro Glu Val Gln Phe Asn Trp Tyr Val Asp Gly Val
Glu Val His Asn Ala Lys Thr Lys Pro Arg Glu Glu Gln Phe
Asn Ser Thr Tyr Arg Val Val Ser Val Leu Thr Val Leu His
Gln Asp Trp Leu Asn Gly Lys Glu Tyr Lys Cys Lys Val Ser
Asn Lys Gly Leu Pro Ser Ser Ile Glu Lys Thr Ile Ser Lys Ala
Lys Gly Gln Pro Arg Glu Pro Gln Val Tyr Thr Leu Pro Pro
Ser Arg Asp Glu Leu Thr Lys Asn Gln Val Ser Leu Thr Cys
Leu Val Lys Gly Phe Tyr Pro Ser Asp Ile Ala Val Glu Trp Glu
Ser Asn Gly Gln Pro Glu Asn Asn Tyr Lys Thr Thr Pro Pro
Val Leu Asp Ser Asp Gly Ser Phe Phe Leu Tyr Ser Lys Leu
Thr Val Asp Lys Ser Arg Trp Gln Gln Gly Asn Val Phe Ser
Cys Ser Val Met His Glu Ala Leu His Asn His Tyr Thr Gln
Lys Ser Leu Ser Leu Ser Pro Gly Lys (SEQ ID NO: 7)

SEQ ID NO: 30 of
WO2014/121087

Ala Ser Thr Lys Gly Pro Ser Val Phe Pro Leu Ala Pro Ser
Ser Lys Ser Thr Ser Gly Gly Thr Ala Ala Leu Gly Cys Leu
Val Lys Asp Tyr Phe Pro Glu Pro Val Thr Val Ser Trp Asn
Ser Gly Ala Leu Thr Ser Gly Val His Thr Phe Pro Ala Val
Leu Gln Ser Ser Gly Leu Tyr Ser Leu Ser Ser Val Val Thr
Val Pro Ser Ser Ser Leu Gly Thr Gln Thr Tyr Ile Cys Asn Val
Asn His Lys Pro Ser Asn Thr Lys Val Asp Lys Lys Val Glu
Pro Lys Ser Cys Asp Lys Thr His Thr Cys Pro Pro Cys
Pro Ala Pro Val Ala Gly Pro Ser Val Phe Leu Phe Pro
Pro Lys Pro Lys Asp Thr Leu Met Ile Ser Arg Thr Pro Glu
Val Thr Cys Val Val Val Asp Val Ser Gln Glu Asp Pro Glu
Val Gln Phe Asn Trp Tyr Val Asp Gly Val Glu Val His Asn
Ala Lys Thr Lys Pro Arg Glu Glu Gln Phe Asn Ser Thr
Tyr Arg Val Val Ser Val Leu Thr Val Leu His Gln Asp Trp
Leu Asn Gly Lys Glu Tyr Lys Cys Lys Val Ser Asn Lys
Gly Leu Pro Ser Ser Ile Glu Lys Thr Ile Ser Lys Ala Lys
Gly Gln Pro Arg Glu Pro Gln Val Tyr Thr Leu Pro Pro Ser
Arg Asp Glu Leu Thr Lys Asn Gln Val Ser Leu Thr Cys
Leu Val Lys Gly Phe Tyr Pro Ser Asp Ile Ala Val Glu Trp
Glu Ser Asn Gly Gln Pro Glu Asn Asn Tyr Lys Thr Thr
Pro Pro Val Leu Asp Ser Asp Gly Ser Phe Phe Leu Tyr
Ser Lys Leu Thr Val Asp Lys Ser Arg Trp Gln Gln Gly
Asn Val Phe Ser Cys Ser Val Met His Glu Ala Leu His
Asn His Tyr Thr Gln Lys Ser Leu Ser Leu Ser Pro Gly
Lys (SEQ ID NO: 8)

SEQ ID NO: 31 of
WO2014/121087

Ala Ser Thr Lys Gly Pro Ser Val Phe Pro Leu Ala Pro Cys
Ser Arg Ser Thr Ser Glu Ser Thr Ala Ala Leu Gly Cys Leu
Val Lys Asp Tyr Phe Pro Glu Pro Val Thr Val Ser Trp Asn
Ser Gly Ala Leu Thr Ser Gly Val His Thr Phe Pro Ala Val
Leu Gln Ser Ser Gly Leu Tyr Ser Leu Ser Ser Val Val Thr
Val Pro Ser Ser Ser Leu Gly Thr Lys Thr Tyr Thr Cys Asn
Val Asp His Lys Pro Ser Asn Thr Lys Val Asp Lys Arg Val
Glu Ser Lys Tyr Gly Pro Pro Cys Pro Pro Cys Pro Ala
Pro Pro Val Ala Gly Pro Ser Val Phe Leu Phe Pro Pro
Lys Pro Lys Asp Thr Leu Met Ile Ser Arg Thr Pro Glu Val
Thr Cys Val Val Val Asp Val Ser Gln Glu Asp Pro Glu Val
Gln Phe Asn Trp Tyr Val Asp Gly Val Glu Val His Asn
Ala Lys Thr Lys Pro Arg Glu Glu Gln Phe Asn Ser Thr
Tyr Arg Val Val Ser Val Leu Thr Val Leu His Gln Asp Trp
Leu Asn Gly Lys Glu Tyr Lys Cys Lys Val Ser Asn Lys
Gly Leu Pro Ser Ser Ile Glu Lys Thr Ile Ser Lys Ala Lys
Gly Gln Pro Arg Glu Pro Gln Val Tyr Thr Leu Pro Pro Ser
Gln Glu Glu Met Thr Lys Asn Gln Val Ser Leu Thr Cys
Leu Val Lys Gly Phe Tyr Pro Ser Asp Ile Ala Val Glu Trp
Glu Ser Asn Gly Gln Pro Glu Asn Asn Tyr Lys Thr Thr
Pro Pro Val Leu Asp Ser Asp Gly Ser Phe Phe Leu Tyr
Ser Arg Leu Thr Val Asp Lys Ser Arg Trp Gln Glu Gly
Asn Val Phe Ser Cys Ser Val Met His Glu Ala Leu His
Asn His Tyr Thr Gln Lys Ser Leu Ser Leu Ser Leu Gly
Lys (SEQ ID NO: 9)

SEQ ID NO: 37 of
WO2014/121087

Ala Ser Thr Lys Gly Pro Ser Val Phe Pro Leu Ala Pro Ser
Ser Lys Ser Thr Ser Gly Gly Thr Ala Ala Leu Gly Cys Leu
Val Lys Asp Tyr Phe Pro Glu Pro Val Thr Val Ser Trp Asn

TABLE 2-continued

Exemplary IgG4 Fc domains with reduced binding to Fc

| Fc Domain | Sequence |
|---|---|
| | Ser Gly Ala Leu Thr Ser Gly Val His Thr Phe Pro Ala Val |
| | Leu Gln Ser Ser Gly Leu Tyr Ser Leu Ser Ser Val Val Thr |
| | Val Pro Ser Ser Ser Leu Gly Thr Gln Thr Tyr Ile Cys Asn Val |
| | Asn His Lys Pro Ser Asn Thr Lys Val Asp Lys Lys Val Glu |
| | Pro Lys Ser Cys Asp Lys Thr His Thr Cys Pro Pro Cys |
| | Pro Ala Pro Pro Val Ala Gly Pro Ser Val Phe Leu Phe Pro |
| | Pro Lys Pro Lys Asp Thr Leu Met Ile Ser Arg Thr Pro Glu |
| | Val Thr Cys Val Val Val Asp Val Ser Gln Glu Asp Pro Glu |
| | Val Gln Phe Asn Trp Tyr Val Asp Gly Val Glu Val His Asn |
| | Ala Lys Thr Lys Pro Arg Glu Glu Gln Phe Asn Ser Thr |
| | Tyr Arg Val Val Ser Val Leu Thr Val Leu His Gln Asp Trp |
| | Leu Asn Gly Lys Glu Tyr Lys Cys Lys Val Ser Asn Lys |
| | Gly Leu Pro Ser Ser Ile Glu Lys Thr Ile Ser Lys Ala Lys |
| | Gly Gln Pro Arg Glu Pro Gln Val Tyr Thr Leu Pro Pro Ser |
| | Arg Asp Glu Leu Thr Lys Asn Gln Val Ser Leu Thr Cys |
| | Leu Val Lys Gly Phe Tyr Pro Ser Asp Ile Ala Val Glu Trp |
| | Glu Ser Asn Gly Gln Pro Glu Asn Asn Tyr Lys Thr Thr |
| | Pro Pro Val Leu Asp Ser Asp Gly Ser Phe Phe Leu Tyr |
| | Ser Lys Leu Thr Val Asp Lys Ser Arg Trp Gln Gln Gly |
| | Asn Val Phe Ser Cys Ser Val Met His Glu Ala Leu His |
| | Asn Arg Phe Thr Gln Lys Ser Leu Ser Leu Ser Pro Gly |
| | Lys (SEQ ID NO: 10) |
| SEQ ID NO: 38 of WO2014/121087 | Ala Ser Thr Lys Gly Pro Ser Val Phe Pro Leu Ala Pro Cys |
| | Ser Arg Ser Thr Ser Glu Ser Thr Ala Ala Leu Gly Cys Leu |
| | Val Lys Asp Tyr Phe Pro Glu Pro Val Thr Val Ser Trp Asn |
| | Ser Gly Ala Leu Thr Ser Gly Val His Thr Phe Pro Ala Val |
| | Leu Gln Ser Ser Gly Leu Tyr Ser Leu Ser Ser Val Val Thr |
| | Val Pro Ser Ser Ser Leu Gly Thr Lys Thr Tyr Thr Cys Asn |
| | Val Asp His Lys Pro Ser Asn Thr Lys Val Asp Lys Arg Val |
| | Glu Ser Lys Tyr Gly Pro Pro Cys Pro Pro Cys Pro Ala |
| | Pro Pro Val Ala Gly Pro Ser Val Phe Leu Phe Pro Pro |
| | Lys Pro Lys Asp Thr Leu Met Ile Ser Arg Thr Pro Glu Val |
| | Thr Cys Val Val Val Asp Val Ser Gln Glu Asp Pro Glu Val |
| | Gln Phe Asn Trp Tyr Val Asp Gly Val Glu Val His Asn |
| | Ala Lys Thr Lys Pro Arg Glu Glu Gln Phe Asn Ser Thr |
| | Tyr Arg Val Val Ser Val Leu Thr Val Leu His Gln Asp Trp |
| | Leu Asn Gly Lys Glu Tyr Lys Cys Lys Val Ser Asn Lys |
| | Gly Leu Pro Ser Ser Ile Glu Lys Thr Ile Ser Lys Ala Lys |
| | Gly Gln Pro Arg Glu Pro Gln Val Tyr Thr Leu Pro Pro Ser |
| | Gln Glu Glu Met Thr Lys Asn Gln Val Ser Leu Thr Cys |
| | Leu Val Lys Gly Phe Tyr Pro Ser Asp Ile Ala Val Glu Trp |
| | Glu Ser Asn Gly Gln Pro Glu Asn Asn Tyr Lys Thr Thr |
| | Pro Pro Val Leu Asp Ser Asp Gly Ser Phe Phe Leu Tyr |
| | Ser Arg Leu Thr Val Asp Lys Ser Arg Trp Gln Glu Gly |
| | Asn Val Phe Ser Cys Ser Val Met His Glu Ala Leu His |
| | Asn Arg Phe Thr Gln Lys Ser Leu Ser Leu Ser Leu Gly |
| | Lys (SEQ ID NO: 11) |

In a particular embodiment, the IgG4 with reduced effector function comprises the bolded portion of the amino acid sequence of SEQ ID NO:31 of WO2014/121087, sometimes referred to herein as IgG4s or hIgG4s.

For heterodimeric Fc regions, it is possible to incorporate a combination of the variant IgG4 Fc sequences set forth above, for example an Fc region comprising an Fc domain comprising the amino acid sequence of SEQ ID NO:30 of WO2014/121087 (or the bolded portion thereof) and an Fc domain comprising the amino acid sequence of SEQ ID NO:37 of WO2014/121087 (or the bolded portion thereof) or an Fc region comprising an Fc domain comprising the amino acid sequence of SEQ ID NO:31 of WO2014/121087 (or the bolded portion thereof) and an Fc domain comprising the amino acid sequence of SEQ ID NO:38 of WO2014/121087 (or the bolded portion thereof).

6.5.1.2. Fc Heterodimerization Variants

Certain CD20-PD1 binding molecules entail dimerization between two Fc domains that, unlike a native immunoglobu-lin, are operably linked to non-identical N-terminal regions, e.g., one Fc domain connected to a Fab and the other Fc domain connected to a PD1 agonist moiety. Inadequate heterodimerization of two Fc domains to form an Fc region has can be an obstacle for increasing the yield of desired heterodimeric molecules and represents challenges for purification. A variety of approaches available in the art can be used in for enhancing dimerization of Fc domains that might be present in the CD20-PD1 binding molecules of the disclosure, for example as disclosed in EP 1870459A1; U.S. Pat. Nos. 5,582,996; 5,731,168; 5,910,573; 5,932,448; 6,833,441; 7,183,076; U.S. Patent Application Publication No. 2006204493A1; and PCT Publication No. WO 2009/089004A1.

The present disclosure provides CD20-PD1 binding molecules comprising Fc heterodimers, i.e., Fc regions comprising heterologous, non-identical Fc domains. Typically, each Fc domain in the Fc heterodimer comprises a CH3 domain of an antibody. The CH3 domains are derived from the constant region of an antibody of any isotype, class or subclass, and preferably of IgG (IgG1, IgG2, IgG3 and IgG4) class, as described in the preceding section.

Heterodimerization of the two different heavy chains at CH3 domains give rise to the desired CD20-PD1 binding molecule, while homodimerization of identical heavy chains will reduce yield of the desired CD20-PD1 binding molecule. Thus, in a preferred embodiment, the polypeptides that associate to form a CD20-PD1 binding molecule of the disclosure will contain CH3 domains with modifications that favor heterodimeric association relative to unmodified Fc domains.

In a specific embodiment said modification promoting the formation of Fc heterodimers is a so-called "knob-into-hole" or "knob-in-hole" modification, comprising a "knob" modification in one of the Fc domains and a "hole" modification in the other Fc domain. The knob-into-hole technology is described e.g., in U.S. Pat. Nos. 5,731,168; 7,695,936; Ridgway et al., 1996, Prot Eng 9:617-621, and Carter, 2001, Immunol Meth 248:7-15. Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine).

Accordingly, in some embodiments, an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable. Preferably said amino acid residue having a larger side chain volume is selected from the group consisting of arginine (R), phenylalanine (F), tyrosine (Y), and tryptophan (VV). Preferably said amino acid residue having a smaller side chain volume is selected from the group consisting of alanine (A), serine (S), threonine (T), and valine (V). The protuberance and cavity can be made by altering the nucleic acid encoding the polypeptides, e.g., by site-specific mutagenesis, or by peptide synthesis. An exemplary substitution is Y470T.

In a specific such embodiment, in the first Fc domain the threonine residue at position 366 is replaced with a tryptophan residue (T366W), and in the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numbering according to Kabat EU index). In a further embodiment, in the first Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second Fc domain additionally the tyrosine residue at position 349 is replaced by a cysteine residue (Y349C) (numbering according to Kabat EU index). In a particular embodiment, the first Fc domain comprises the amino acid substitutions S354C and T366W, and the second Fc domain comprises the amino acid substitutions Y349C, T366S, L368A and Y407V (numbering according to Kabat EU index).

In some embodiments, electrostatic steering (e.g., as described in Gunasekaran et al., 2010, J Biol Chem 285(25): 19637-46) can be used to promote the association of the first and the second Fc domains of the Fc region.

As an alternative, or in addition, to the use of Fc domains that are modified to promote heterodimerization, an Fc domain can be modified to allow a purification strategy that enables selections of Fc heterodimers. In one such embodiment, one polypeptide comprises a modified Fc domain that abrogates its binding to Protein A, thus enabling a purification method that yields a heterodimeric protein. See, for example, U.S. Pat. No. 8,586,713. As such, the CD20-PD1 binding molecules comprise a first CH3 domain and a second Ig CH3 domain, wherein the first and second Ig CH3 domains differ from one another by at least one amino acid, and wherein at least one amino acid difference reduces binding of the CD20-PD1 binding molecule to Protein A as compared to a corresponding CD20-PD1 binding molecule lacking the amino acid difference. In one embodiment, the first CH3 domain binds Protein A and the second CH3 domain contains a mutation/modification that reduces or abolishes Protein A binding such as an H95R modification (by IMGT exon numbering; H435R by EU numbering). The second CH3 may further comprise a Y96F modification (by IMGT; Y436F by EU). This class of modifications is referred to herein as "star" mutations.

In some embodiments, the Fc can contain one or more mutations (e.g., knob and hole mutations) to facilitate heterodimerization as well as star mutations to facilitate purification.

6.6. Stabilization Moieties

The CD20-PD1 binding molecules of the disclosure can comprise a stabilization moiety that can extend the molecule's serum half-life in vivo. Serum half-life is often divided into an alpha phase and a beta phase. Either or both phases may be improved significantly by addition of an appropriate stabilization moiety. For example, the stabilization moiety can increase the serum half-life of the CD20-PD1 binding molecule by more than 5, 10, 20, 30, 40, 50, 60, 70, 80, 90, 100, 120, 150, 200, 400, 600, 800, 1000% or more relative to a corresponding CD20-PD1 binding molecule not containing the stabilization moiety. For the purpose of this disclosure, serum half-life can refer to the half-life in humans or other mammals (e.g., mice or non-human primates).

Stabilization moieties, include polyoxyalkylene moieties (e.g., polyethylene glycol), sugars (e.g., sialic acid), and well-tolerated protein moieties (e.g., Fc and fragments and variants thereof, transferrin, or serum albumin).

Other stabilization moieties that can be used in the CD20-PD1 binding molecules of the disclosure include those described in Kontermann et al., 2011, Current Opinion in Biotechnology 22:868-76. Such Stabilization moieties include, but are not limited to, human serum albumin fusions, human serum albumin conjugates, human serum albumin binders (e.g., Adnectin PKE, AlbudAb, ABD), XTEN fusions, PAS fusions (i.e., recombinant PEG mimetics based on the three amino acids proline, alanine, and serine), carbohydrate conjugates (e.g., hydroxyethyl starch (HES)), glycosylation, polysialic acid conjugates, and fatty acid conjugates.

Accordingly, in some embodiments the disclosure provides a CD20-PD1 binding molecule comprising a stabilization moiety that is a polymeric sugar.

Serum albumin can also be engaged in half-life extension through modules with the capacity to non-covalently interact with albumin. Accordingly, the CD20-PD1 binding molecules of the disclosure can include as a stabilization moiety an albumin-binding protein. The albumin-binding protein can be either conjugated or genetically fused to one or more other components of the CD20-PD1 binding molecules of the disclosure. Proteins with albumin-binding activity are known from certain bacteria. For example, streptococcal protein G contains several small albumin-binding domains composed of roughly 50 amino acid residues (6 kDa). Additional examples of serum albumin binding proteins such as those described in U.S. Publication Nos. 2007/0178082 and 2007/0269422. Fusion of an albumin binding domain to a protein results in a strongly extended half-life (see Kontermann et al., 2011, Current Opinion in Biotechnology 22:868-76).

In other embodiments the stabilization moiety is human serum albumin. In other embodiments, the stabilization moiety is transferrin.

In some embodiments, the stabilization moiety is an Fc domain, for example any of the Fc domains described in Section 6.5.1 and subsections thereof, incorporated by reference herein. The Fc domains described in Section 6.5.1 are generally capable of dimerization. However, for the purpose of stabilization the Fc domain can be a soluble monomeric Fc domain that has a reduced ability to self-associate. See, e.g., Helm et al., 1996, J. Biol. Chem. 271: 7494-7500 and Ying et al., 2012, J Biol Chem. 287(23):19399-19408. An example of a soluble monomeric Fc domain comprises amino acid substitutions in the positions corresponding to T366 and/or Y407 in CH3, as described in U.S. Patent Publication No. 2019/0367611. The monomeric Fc domains can be of any Ig subtype and can include additional substitutions that reduce effector function, as described in Section 6.5.1 and subsections thereof.

In yet other embodiments, the stabilization moiety is a polyethylene glycol moiety or another polymer, as described in Section 6.6.1 below.

The stabilization moiety can be connected to one or more other components of the CD20-PD1 binding molecules of the disclosure via a linker, for example as described in Section 6.7 below.

6.6.1. Polyethylene Glycol

In some embodiments, the CD20-PD1 binding molecule comprises polyethylene glycol (PEG) or another hydrophilic polymer as a stabilization moiety, for example a copolymer of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), dextran or poly(n-vinyl pyrrolidone)polyethylene glycol, a propropylene glycol homopolymer, a prolypropylene oxide/ethylene oxide copolymer, a polyoxyethylated polyol (e.g., glycerol), polyvinyl alcohol, and mixtures thereof. The polymer may be of any molecular weight, and may be branched or unbranched.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X—O(CH_2CH_2O)_n\text{-}1CH_2CH_2OH$, where n is 20 to 2300 and X is H or a terminal modification, e.g., a $C_{1-4}$ alkyl. PEG can contain further chemical groups which are necessary for binding reactions, which result from the chemical synthesis of the molecule; or which act as a spacer for optimal distance of parts of the molecule. In addition, such a PEG can consist of one or more PEG side-chains which are linked together. PEGs with more than one PEG chain are called multiarmed or branched PEGs. Branched PEGs are described in, for example, European Application No. 473084A and U.S. Pat. No. 5,932,462.

One or more PEG molecules can be attached at different positions on the CD20-PD1 binding molecule, and such attachment may be achieved by reaction with amines, thiols or other suitable reactive groups. The amine moiety may be, for example, a primary amine found at the N-terminus of the CD20-PD1 binding molecule (or a component thereof) or an amine group present in an amino acid, such as lysine or arginine.

PEGylation can be achieved by site-directed PEGylation, wherein a suitable reactive group is introduced into the protein to create a site where PEGylation preferentially occurs. In some embodiments, the CD20-PD1 binding molecule is modified to introduce a cysteine residue at a desired position, permitting site-directed PEGylation on the cysteine. Mutations can be introduced into the coding sequence of a CD20-PD1 binding molecule of the disclosure to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or three dimensional structure. PEGylation of cysteine residues may be carried out using, for example, PEG-maleimide, PEG-vinylsulfone, PEG-iodoacetamide, or PEG-orthopyridyl disulfide.

The PEG is typically activated with a suitable activating group appropriate for coupling to a desired site on the polypeptide. PEGylation methods are well-known in the art and further described in Zalipsky et al., "Use of Functionalized Poly(Ethylene Glycols) for Modification of Polypeptides" in Polyethylene Glycol Chemistry: Biotechnical and Biomedical Applications, J. M. Harris, Plenus Press, New York (1992), and in Zalipsky, 1995, Advanced Drug Reviews 16: 157-182.

PEG moieties may vary widely in molecular weight and may be branched or linear. Typically, the weight-average molecular weight of PEG is from about 100 Daltons to about 150,000 Daltons. Exemplary weight-average molecular weights for PEG include about 20,000 Daltons, about 40,000 Daltons, about 60,000 Daltons and about 80,000 Daltons. In certain embodiments, the molecular weight of PEG is 40,000 Daltons. Branched versions of PEG having a total molecular weight of any of the foregoing can also be used. In some embodiments, the PEG has two branches. In other embodiments, the PEG has four branches. In another embodiment, the PEG is a bis-PEG (NOF Corporation, DE-200MA).

Conventional separation and purification techniques known in the art can be used to purify PEGylated CD20-PD1 binding molecules, such as size exclusion (e.g., gel filtration) and ion exchange chromatography. Products can also be separated using SDS-PAGE. Products that can be separated include mono-, di-, tri-, poly- and un-PEGylated CD20-PD1 binding molecules, as well as free PEG. The percentage of mono-PEG conjugates can be controlled by pooling broader fractions around the elution peak to increase the percentage of mono-PEG in the composition. About 90% mono-PEG conjugates represent a good balance of yield and activity.

In some embodiments, the PEGylated CD20-PD1 binding molecule will preferably retain at least about 25%, 50%, 60%, 70%, 80%, 85%, 90%, 95% or 100% of the biological activity associated with the unmodified CD20-PD1 binding molecule. In some embodiments, biological activity refers to its ability to bind to CD20, PD1, or both CD20 and PD1, as assessed by $K_D$, $k_{on}$, or $k_{off}$.

6.7. Linkers

In certain aspects, the present disclosure provides CD20-PD1 binding molecules in which two or more components of a CD20-PD1 binding molecules are connected to one another by a peptide linker. By way of example and not limitation, linkers can be used to connect (a) a CD20 targeting moiety and a dimerization moiety; (b) a CD20 targeting moiety and a PD1 agonist moiety; (c) a PD1 agonist moiety and a dimerization moiety; or (d) different domains within a CD20 targeting moiety (e.g., the VH and VL domains in an scFv).

A peptide linker can range from 2 amino acids to 60 or more amino acids, and in certain aspects a peptide linker ranges from 3 amino acids to 50 amino acids, from 4 to 30 amino acids, from 5 to 25 amino acids, from 10 to 25 amino acids, 10 amino acids to 60 amino acids, from 12 amino acids to 20 amino acids, from 20 amino acids to 50 amino acids, or from 25 amino acids to 35 amino acids in length.

In particular aspects, a peptide linker is at least 5 amino acids, at least 6 amino acids or at least 7 amino acids in length and optionally is up to 30 amino acids, up to 40 amino acids, up to 50 amino acids or up to 60 amino acids in length.

In some embodiments of the foregoing, the linker ranges from 5 amino acids to 50 amino acids in length, e.g., ranges from 5 to 50, from 5 to 45, from 5 to 40, from 5 to 35, from 5 to 30, from 5 to 25, or from 5 to 20 amino acids in length. In other embodiments of the foregoing, the linker ranges from 6 amino acids to 50 amino acids in length, e.g., ranges from 6 to 50, from 6 to 45, from 6 to 40, from 6 to 35, from 6 to 30, from 6 to 25, or from 6 to 20 amino acids in length. In yet other embodiments of the foregoing, the linker ranges from 7 amino acids to 50 amino acids in length, e.g., ranges from 7 to 50, from 7 to 45, from 7 to 40, from 7 to 35, from 7 to 30, from 7 to 25, or from 7 to 20 amino acids in length.

Charged (e.g., charged hydrophilic linkers) and/or flexible linkers are particularly preferred.

Examples of flexible linkers that can be used in the CD20-PD1 binding molecules of the disclosure include those disclosed by Chen et al., 2013, Adv Drug Deliv Rev. 65(10): 1357-1369 and Klein et al., 2014, Protein Engineering, Design & Selection 27(10): 325-330. Particularly useful flexible linkers are or comprise repeats of glycines and serines, e.g., a monomer or multimer of $G_nS$ (SEQ ID NO: 12) or SG, (SEQ ID NO: 13), where n is an integer from 1 to 10, e.g., 1 2, 3, 4, 5, 6, 7, 8, 9 or 10. In one embodiment, the linker is or comprises a monomer or multimer of repeat of $G_4S$ e.g., $(GGGGS)_n$ (SEQ ID NO: 14).

Polyglycine linkers can suitably be used in the CD20-PD1 binding molecules of the disclosure. In some embodiments, a peptide linker comprises two consecutive glycines (2Gly), three consecutive glycines (3Gly), four consecutive glycines (4Gly) (SEQ ID NO: 15), five consecutive glycines (5Gly) (SEQ ID NO: 16), six consecutive glycines (6Gly) (SEQ ID NO: 17), seven consecutive glycines (7Gly) (SEQ ID NO: 18), eight consecutive glycines (8Gly) (SEQ ID NO: 19) or nine consecutive glycines (9Gly) (SEQ ID NO: 20).

6.7.1. Hinge Sequences

In some embodiments, the CD20-PD1 binding molecules of the disclosure comprise a linker that is a hinge region. In particular, the hinge can be used to connect the CD20 targeting moiety, e.g., a Fab domain, to a dimerization domain, e.g., an Fc domain. The hinge region can be a native or a modified hinge region. Hinge regions are typically found at the N-termini of Fc regions. The term "hinge region", unless the context dictates otherwise, refers to a naturally or non-naturally occurring hinge sequence that in the context of a single or monomeric polypeptide chain is a monomeric hinge domain and in the context of a dimeric polypeptide (e.g., a homodimeric or heterodimeric CD20-PD1 binding molecule formed by the association of two Fc domains) can comprise two associated hinge sequences on separate polypeptide chains.

A native hinge region is the hinge region that would normally be found between Fab and Fc domains in a naturally occurring antibody. A modified hinge region is any hinge that differs in length and/or composition from the native hinge region. Such hinges can include hinge regions from other species, such as human, mouse, rat, rabbit, shark, pig, hamster, camel, llama or goat hinge regions. Other modified hinge regions may comprise a complete hinge region derived from an antibody of a different class or subclass from that of the heavy chain Fc domain or Fc region. Alternatively, the modified hinge region may comprise part of a natural hinge or a repeating unit in which each unit in the repeat is derived from a natural hinge region. In a further alternative, the natural hinge region may be altered by converting one or more cysteine or other residues into neutral residues, such as serine or alanine, or by converting suitably placed residues into cysteine residues. By such means the number of cysteine residues in the hinge region may be increased or decreased. Other modified hinge regions may be entirely synthetic and may be designed to possess desired properties such as length, cysteine composition and flexibility.

A number of modified hinge regions have already been described, for example, in U.S. Pat. No. 5,677,425, WO 99/15549, WO 2005/003170, WO 2005/003169, WO 2005/003170, WO 98/25971 and WO 2005/003171 and these are incorporated herein by reference.

In one embodiment, a CD20-PD1 binding molecule of the disclosure comprises an Fc region in which one or both Fc domains possesses an intact hinge region at its N-terminus.

In various embodiments, positions 233-236 within a hinge region may be G, G, G and unoccupied; G, G, unoccupied, and unoccupied; G, unoccupied, unoccupied, and unoccupied; or all unoccupied, with positions numbered by EU numbering.

In some embodiments, the CD20-PD1 binding molecules of the disclosure comprise a modified hinge region that reduces binding affinity for an Fcγ receptor relative to a wild-type hinge region of the same isotype (e.g., human IgG1 or human IgG4).

In one embodiment, the CD20-PD1 binding molecules of the disclosure comprise an Fc region in which each Fc domain possesses an intact hinge region at its N-terminus, where each Fc domain and hinge region is derived from IgG4 and each hinge region comprise the modified sequence CPPC (SEQ ID NO: 21). The core hinge region of human IgG4 contains the sequence CPSC (SEQ ID NO: 22) compared to IgG1 that contains the sequence CPPC (SEQ ID NO: 29). The serine residue present in the IgG4 sequence leads to increased flexibility in this region, and therefore a proportion of molecules form disulfide bonds within the same protein chain (an intrachain disulfide) rather than bridging to the other heavy chain in the IgG molecule to form the interchain disulfide. (Angel et al., 1993, Mol Immunol 30(1):105-108). Changing the serine residue to a proline to give the same core sequence as IgG1 allows complete formation of inter-chain disulfides in the IgG4 hinge region, thus reducing heterogeneity in the purified product. This altered isotype is termed IgG4P.

6.7.1.1. Chimeric Hinge Sequences

The hinge region can be a chimeric hinge region.

For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region.

In particular embodiments, a chimeric hinge region comprises the amino acid sequence EPKSCDKTH-TCPPCPAPPVA (SEQ ID NO: 23) (previously disclosed as SEQ ID NO:8 of WO2014/121087, which is incorporated by reference in its entirety herein) or ESKYGPPCPPCPAPPVA (SEQ ID NO: 24) (previously disclosed as SEQ ID NO:9 of WO2014/121087). Such chimeric hinge sequences can be suitably linked to an IgG4 CH2 region (for example by incorporation into an IgG4 Fc domain, for example a human or murine Fc domain, which can be further modified in the CH2 and/or CH3 domain to reduce effector function, for example as described in Section 6.5.1.1).

6.7.1.2. Hinge Sequences with Reduced Effector Function

In further embodiments, the hinge region can be modified to reduce effector function, for example as described in WO2016161010A2, which is incorporated by reference in its entirety herein. In various embodiments, the positions 233-236 of the modified hinge region are G, G, G and unoccupied; G, G, unoccupied, and unoccupied; G, unoccupied, unoccupied, and unoccupied; or all unoccupied, with positions numbered by EU numbering (as shown in FIG. 1 of WO2016161010A2). These segments can be represented as GGG-, GG--, G--- or ---- with "-" representing an unoccupied position.

Position 236 is unoccupied in canonical human IgG2 but is occupied by in other canonical human IgG isotypes. Positions 233-235 are occupied by residues other than G in all four human isotypes (as shown in FIG. 1 of WO2016161010A2).

The hinge modification within positions 233-236 can be combined with position 228 being occupied by P. Position 228 is naturally occupied by P in human IgG1 and IgG2 but is occupied by S in human IgG4 and R in human IgG3. An S228P mutation in an IgG4 antibody is advantageous in stabilizing an IgG4 antibody and reducing exchange of heavy chain light chain pairs between exogenous and endogenous antibodies. Preferably positions 226-229 are occupied by C, P, P and C respectively ("CPPC" disclosed as SEQ ID NO: 21).

Exemplary hinge regions have residues 226-236, sometimes referred to as middle (or core) and lower hinge, occupied by the modified hinge sequences designated GGG-(233-236), GG--(233-236), G---(233-236) and no G(233-236). Optionally, the hinge domain amino acid sequence comprises CPPCPAPGGG-GPSVF (SEQ ID NO: 25) (previously disclosed as SEQ ID NO:1 of WO2016161010A2), CPPCPAPGG--GPSVF (SEQ ID NO: 26) (previously disclosed as SEQ ID NO:2 of WO2016161010A2), CPPCPAPG---GPSVF (SEQ ID NO: 27) (previously disclosed as SEQ ID NO:3 of WO2016161010A2), or CPPCPAP----GPSVF (SEQ ID NO: 28) (previously disclosed as SEQ ID NO:4 of WO2016161010A2).

The modified hinge regions described above can be incorporated into a heavy chain constant region, which typically include CH2 and CH3 domains, and which may have an additional hinge segment (e.g., an upper hinge) flanking the designated region. Such additional constant region segments present are typically of the same isotype, preferably a human isotype, although can be hybrids of different isotypes. The isotype of such additional human constant regions segments is preferably human IgG4 but can also be human IgG1, IgG2, or IgG3 or hybrids thereof in which domains are of different isotypes. Exemplary sequences of human IgG1, IgG2 and IgG4 are shown in FIGS. 2-4 of WO2016161010A2.

In specific embodiments, the modified hinge sequences can be linked to an IgG4 CH2 region (for example by incorporation into an IgG4 Fc domain, for example a human or murine Fc domain, which can be further modified in the CH2 and/or CH3 domain to reduce effector function, for example as described in Section 6.5.1.1).

6.8. Nucleic Acids and Host Cells

In another aspect, the disclosure provides nucleic acids encoding the CD20-PD1 binding molecules of the disclosure. In some embodiments, the CD20-PD1 binding molecules are encoded by a single nucleic acid. In other embodiments, for example in the case of a heterodimeric molecule or a molecule comprising a CD20 targeting moiety composed of more than one polypeptide chain, the CD20-PD1 binding molecules can be encoded by a plurality (e.g., two, three, four or more) nucleic acids.

A single nucleic acid can encode a CD20-PD1 binding molecule that comprises a single polypeptide chain, a CD20-PD1 binding molecule that comprises two or more polypeptide chains, or a portion of a CD20-PD1 binding molecule that comprises more than two polypeptide chains (for example, a single nucleic acid can encode two polypeptide chains of a CD20-PD1 binding molecule comprising three, four or more polypeptide chains, or three polypeptide chains of a CD20-PD1 binding molecule comprising four or more polypeptide chains). For separate control of expression, the open reading frames encoding two or more polypeptide chains can be under the control of separate transcriptional regulatory elements (e.g., promoters and/or enhancers). The open reading frames encoding two or more polypeptides can also be controlled by the same transcriptional regulatory elements, and separated by internal ribosome entry site (IRES) sequences allowing for translation into separate polypeptides.

In some embodiments, a CD20-PD1 binding molecule comprising two or more polypeptide chains is encoded by two or more nucleic acids. The number of nucleic acids encoding a CD20-PD1 binding molecule can be equal to or less than the number of polypeptide chains in the CD20-PD1 binding molecule (for example, when more than one polypeptide chains are encoded by a single nucleic acid).

The nucleic acids of the disclosure can be DNA or RNA (e.g., mRNA).

In another aspect, the disclosure provides host cells and vectors containing the nucleic acids of the disclosure. The nucleic acids may be present in a single vector or separate vectors present in the same host cell or separate host cell, as described in more detail herein below.

6.8.1. Vectors

The disclosure provides vectors comprising nucleotide sequences encoding a CD20-PD1 binding molecule or a CD20-PD1 binding molecule component described herein, for example one or two of the polypeptide chains of a CD20-PD1 monomer. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes can be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by co-transformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors can be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. Methods and conditions for culturing the resulting transfected cells and for recovering the expressed polypeptides are known to those skilled in the art, and may be varied or optimized depending upon the specific expression vector and mammalian host cell employed, based upon the present description.

6.8.2. Cells

The disclosure also provides host cells comprising a nucleic acid of the disclosure.

In one embodiment, the host cells are genetically engineered to comprise one or more nucleic acids described herein.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The disclosure also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

6.9. Pharmaceutical Compositions

6.9.1. Pharmaceutical Compositions Comprising CD20-PD1 Binding Molecules

The CD20-PD1 binding molecules of the disclosure may be in the form of compositions comprising the CD20-PD1 binding molecule and one or more carriers, excipients and/or diluents. The compositions may be formulated for specific uses, such as for veterinary uses or pharmaceutical uses in humans. The form of the composition (e.g., dry powder, liquid formulation, etc.) and the excipients, diluents and/or carriers used will depend upon the intended use of the CD20-PD1 binding molecule and, for therapeutic uses, the mode of administration.

For therapeutic uses, the compositions may be supplied as part of a sterile, pharmaceutical composition that includes a pharmaceutically acceptable carrier. This composition can be in any suitable form (depending upon the desired method of administering it to a patient). The pharmaceutical composition can be administered to a patient by a variety of routes such as orally, transdermally, subcutaneously, intranasally, intravenously, intramuscularly, intratumorally, intrathecally, topically or locally. The most suitable route for administration in any given case will depend on the particular antibody, the subject, and the nature and severity of the disease and the physical condition of the subject. Typically, the pharmaceutical composition will be administered intravenously or subcutaneously.

Pharmaceutical compositions can be conveniently presented in unit dosage forms containing a predetermined amount of a CD20-PD1 binding molecule of the disclosure per dose. The quantity of CD20-PD1 binding molecule included in a unit dose will depend on the disease being treated, as well as other factors as are well known in the art. Such unit dosages may be in the form of a lyophilized dry powder containing an amount of CD20-PD1 binding molecule suitable for a single administration, or in the form of a liquid. Dry powder unit dosage forms may be packaged in a kit with a syringe, a suitable quantity of diluent and/or other components useful for administration. Unit dosages in liquid form may be conveniently supplied in the form of a syringe pre-filled with a quantity of CD20-PD1 binding molecule suitable for a single administration.

The pharmaceutical compositions may also be supplied in bulk from containing quantities of CD20-PD1 binding molecule suitable for multiple administrations.

Pharmaceutical compositions may be prepared for storage as lyophilized formulations or aqueous solutions by mixing a CD20-PD1 binding molecule having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington, The Science and Practice of Pharmacy, 23rd edition (Adejare, ed. 2020). Such additives should be nontoxic to the recipients at the dosages and concentrations employed.

Buffering agents help to maintain the pH in the range which approximates physiological conditions. They may be present at a wide variety of concentrations, but will typically be present in concentrations ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives may be added to retard microbial growth, and can be added in amounts ranging from about 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, a-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trehalose; and trisaccacharides such as raffinose; and polysaccharides such as dextran.

Stabilizers may be present in amounts ranging from 0.5 to 10 wt per wt of CD20-PD1 binding molecule.

Non-ionic surfactants or detergents (also known as "wetting agents") may be added to help solubilize the glycoprotein as well as to protect the glycoprotein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), and pluronic polyols. Non-ionic surfactants may be present in a range of about 0.05 mg/mL to about 1.0 mg/mL, for example about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), and cosolvents.

6.9.2. Pharmaceutical Compositions for Delivery CD20-PD1 Binding Molecule-Encoding Nucleic Acids A CD20-PD1 binding molecule of the disclosure can be delivered by any method useful for gene therapy, for example as mRNA or through viral vectors encoding the CD20-PD1 binding molecule under the control of a suitable promoter.

Exemplary gene therapy vectors include adenovirus- or AAV-based therapeutics. Non-limiting examples of adenovirus-based or AAV-based therapeutics for use in the methods, uses or compositions herein include, but are not limited to: rAd-p53, which is a recombinant adenoviral vector encoding the wild-type human tumor suppressor protein p53, for example, for the use in treating a cancer (also known as Gendicine®, Genkaxin®, Qi et al., 2006, Modern Oncology, 14:1295-1297); Ad5_d11520, which is an adenovirus lacking the E1B gene for inactivating host p53 (also called H101 or ONYX-015; see, e.g., Russell et al., 2012, Nature Biotechnology 30:658-670); AD5-D24-GM-CSF, an adenovirus containing the cytokine GM-CSF, for example, for the use in treating a cancer (Cerullo et al., 2010, Cancer Res. 70:4297); rAd-HSVtk, a replication deficient adenovirus with HSV thymidine kinase gene, for example, for the treatment of cancer (developed as Cerepro®, Ark Therapeutics, see e.g. U.S. Pat. No. 6,579,855; developed as ProstAtak™ by Advantagene; International PCT Appl. No. WO2005/049094); rAd-TNFα, a replication-deficient adenoviral vector expressing human tumor necrosis factor alpha (TNFα) under the control of the chemoradiation-inducible EGR-1 promoter, for example, for the treatment of cancer (TNFerade™, GenVec; Rasmussen et al., 2002, Cancer Gene Ther. 9:951-7; Ad-IFNβ, an adenovirus serotype 5 vector from which the E1 and E3 genes have been deleted expressing the human interferon-beta gene under the direction of the cytomegalovirus (CMV) immediate-early promoter, for example for treating cancers (BG00001 and H5.110CMVhIFN-β, Biogen; Sterman et al., 2010, Mol. Ther. 18:852-860).

The nucleic acid molecule (e.g., mRNA) or virus can be formulated as the sole pharmaceutically active ingredient in a pharmaceutical composition or can be combined with other active agents for the particular disease to be treated. Optionally, other medicinal agents, pharmaceutical agents, carriers, adjuvants, diluents can be included in the compositions provided herein. For example, any one or more of a wetting agents, emulsifiers and lubricants, such as sodium lauryl sulfate and magnesium stearate, as well as coloring agents, release agents, coating agents, sweetening, flavoring and perfuming agents, preservatives, antioxidants, chelating agents and inert gases also can be present in the compositions. Exemplary other agents and excipients that can be included in the compositions include, for example, water soluble antioxidants, such as ascorbic acid, cysteine hydrochloride, sodium bisulfate, sodium metabisulfite, sodium sulfite; oil-soluble antioxidants, such as ascorbyl palmitate, butylated hydroxyanisole (BHA), butylated hydroxytoluene (BHT), lecithin, propyl gallate, α-tocopherol; and metal chelating agents, such as citric acid, ethylenediamine tetraacetic acid (EDTA), sorbitol, tartaric acid and phosphoric acid.

When used as adjunct therapy for adoptive cell transfer therapies, e.g., CAR-expressing cell therapies as described in Section 6.11.1, the cell therapies, e.g., CAR-expressing cells, can be engineered to express the CD20-PD1 binding molecule of the disclosure. The CD20-PD1 binding molecule can be targeted to a specific genomic locus, e.g., a locus that is active in activated or dysfunctional lymphocytes, e.g., the PD-1 locus, or inserted into a non-specific genomic locus. Targeting a specific genomic locus can be achieved through gene editing, e.g., using zinc finger proteins, the CRISPR/Cas9 system, and the like.

6.10. Therapeutic Indications and Methods of Treatment

CD20-PD1 binding molecules of the disclosure are useful in treating disease states where modulation of the immune system of the host is beneficial, in particular conditions where repression of a cellular immune response is desirable. Thus, the CD20-PD1 binding molecules of the disclosure can be used to repress the immune response in a variety of applications.

The conditions for which the repression of a cellular immune response is desirable may include disease states resulting from an autoimmune response. Disease states for which the CD20-PD1 binding molecules of the disclosure can be administered comprise, for example, an autoimmune disease where repression of a cellular autoimmune response would be an important mechanism. Specific disease states for which CD20-PD1 binding molecules of the present disclosure can be employed include type 1 diabetes (T1D), systemic lupus erythematosus, Crohn's disease, and graft-versus-host disease (GVHD). The CD20-PD1 binding molecules of the disclosure may be administered per se or in any suitable pharmaceutical composition.

In one aspect, CD20-PD1 binding molecules of the disclosure for use as a medicament are provided. In further aspects, CD20-PD1 binding molecules of the disclosure for use in treating a disease are provided. In certain embodiments, CD20-PD1 binding molecules of the disclosure for use in a method of treatment are provided. In one embodiment, the disclosure provides a CD20-PD1 binding molecule as described herein for use in the treatment of a disease in a subject in need thereof. In certain embodiments, the disclosure provides a CD20-PD1 binding molecules for use in a method of treating a subject having an autoimmune disease comprising administering to the individual a therapeutically effective amount of the CD20-PD1 binding molecule. In certain embodiments the disease to be treated is an autoimmune disease. In a particular embodiment the disease is T1D. In other embodiments the disease is systemic lupus erythematosus. In other embodiments the disease is Crohn's disease. In yet other embodiments the disease is GVHD. In certain embodiments the method further comprises administering to the individual a therapeutically effective amount of at least one additional therapeutic agent. In further embodiments, the disclosure provides a CD20-PD1 binding molecules agonist for use in repressing the immune system. In certain embodiments, the disclosure provides a CD20-PD1 binding molecule for use in a method of repressing the immune system in a subject comprising administering to the individual an effective amount of the CD20-PD1 binding molecule to repress the immune system. An "individual" according to any of the above embodiments is a mammal, for example a human. "Repression of the immune system" according to any of the above embodiments may include any one or more of a general decrease in immune function, a decrease in T cell function, a decrease in B cell function, a decrease in T cell responsiveness, and the like. "Repression of a cellular autoimmune response" according to any of the above embodiments may include, for example, a decrease in immune signal (e.g., secretion of immune activating cytokines), a decrease in function of an immune cell targeting an autoantigen, and the like.

The present disclosure further provides a method of localized PD1 agonism, comprising administering to a subject a CD20-PD1 binding molecule or pharmaceutical composition as described herein. As used herein, the term "locally delivered" does not require local administration but rather indicates that the CD20-PD1 binding molecule is selectively or preferentially localized at the intended site of immune modulation, e.g., site of autoimmune activity and/or an intended cell type, e.g., B cells.

The present disclosure further provides a method of administering to the subject PD1 agonist therapy with reduced systemic exposure and/or reduced systemic toxicity, comprising administering to a subject the PD1 agonist therapy in the form of a CD20-PD1 binding molecule or pharmaceutical composition as described herein, for example where CD20 is expressed by a tissue for which PD1 agonist therapy is desirable and/or intended.

Accordingly, the foregoing methods permit PD1 agonist therapy with reduced off-target side effects by virtue of preferential delivery a CD20-PD1 binding molecule at a locale intended for PD1 agonist treatment.

The present disclosure further provides method of locally modulating (e.g., inhibiting) an immune response in a target tissue that expresses CD20, comprising administering to a subject CD20-PD1 binding molecule or pharmaceutical composition as described herein.

In some embodiments, the administration is not local to the tissue.

In a further aspect, the disclosure provides for the use of a CD20-PD1 binding molecule of the disclosure in the manufacture or preparation of a medicament for the treatment of a disease in a subject in need thereof. In one embodiment, the medicament is for use in a method of treating a disease comprising administering to a subject having the disease a therapeutically effective amount of the medicament. In certain embodiments the disease to be treated is an autoimmune disease. In a particular embodiment the disease is T1D. In other embodiments the disease is systemic lupus erythematosus. In other embodiments the disease is Crohn's disease. In yet other embodiments the disease is GVHD. In certain embodiments, the method further comprises administering to the individual a therapeutically effective amount of at least one additional therapeutic agent. In a further embodiment, the medicament is for repressing the immune system. In a further embodiment, the medicament is for use in a method of repressing the immune system in a subject comprising administering to the individual an amount effective of the medicament to repress the immune system. An "individual" according to any of the above embodiments may be a mammal, for example a human. "Repression of the immune system" according to any of the above embodiments may include any one or more of a general decrease in immune function, a decrease in T cell function, a decrease in B cell function, a decrease in T cell responsiveness, and the like.

In a further aspect, the disclosure provides a method of clustering PD1 and/or enhancing PD1 activity in a subject, comprising administering to said subject an effective amount of a CD20-PD1 binding molecule of the disclosure. The CD20-PD1 binding molecules of the disclosure can induce PD1 clustering at the interface of a CD20-presenting cell and a T cell. This provides for targeted immunosuppression, where the CD20-presenting cells and surrounding cells and tissues are protected from T cell killing. High levels of CD20 can be found on B cells, which are abundant in draining lymph nodes and in autoimmune tissues (e.g., the pancreas in type 1 diabetes (T1D)). The CD20-PD1 binding molecules of the disclosure can agonize PD1 in a cell and/or tissue specific manner, inhibiting autoreactive T cell activation. In T1D, the abundance of CD20+ B cells provides for the clustering of PD1 on autoreactive T cells, inhibiting autoreactive cytotoxic T cells from killing islet cells. In one embodiment a composition is administered to said subject, comprising the CD20-PD1 binding molecule of the disclosure in a pharmaceutically acceptable form.

In a further aspect, the disclosure provides a method for treating an autoimmune disease in a subject, comprising administering to said individual a therapeutically effective amount of a CD20-PD1 binding molecule of the disclosure. In one embodiment a composition is administered to said individual, comprising the CD20-PD1 binding molecule of the disclosure in a pharmaceutically acceptable form. In certain embodiments the disease to be treated is an autoimmune disease. Autoimmune diseases treatable by the CD20-PD1 binding molecules of the disclosure can include type 1 diabetes, primary biliary cholangitis (PBC), Goodpasture's syndrome, amyloidosis, ankylosing spondylitis, anti—glomerular basement membrane nephritis, anti-tubular basement membrane nephritis, antiphospholipid syndrome, autoimmune hepatitis, autoimmune oophoritis, graft vs. host disease (GVHD), autoimmune pancreatitis, autoimmune retinopathy, Behcet's disease, Crohn's disease, Devic's disease, systemic lupus erythematosus (SLE), Dressler's syndrome, fibrosing alveolitis, glomerulonephritis, Graves' disease, Guillain-Barre syndrome, IgA Nephropathy, IgG4-related sclerosing disease, immune thrombocytopenic purpura (ITP), microscopic polyangiitis (MPA), mixed connective tissue disease (MCTD), multiple sclerosis, polyneuropathy, organomegaly, endocrinopathy, monoclonal syndrome (POEMS), polyarteritis nodosa, rheumatoid arthritis, Schmidt syndrome, scleritis, scleroderma, Sjögren's syndrome, sperm or testicular autoimmunity, stiff person syndrome (SPS), Takayasu's arteritis, temporal arteritis, giant cell arteritis, thrombocytopenic purpura (TTP), Tolosa-Hunt syndrome (THS), ulcerative colitis, and vasculitis.

In a particular embodiment the disease is T1D. In other embodiments the disease is systemic lupus erythematosus. In other embodiments the disease is Crohn's disease. In yet other embodiments the disease is GVHD. In certain embodiments the method further comprises administering to the individual a therapeutically effective amount of at least one additional therapeutic agent. In a further aspect, the disclosure provides a method for repressing the immune system in a subject, comprising administering to the individual an effective amount of a CD20-PD1 binding molecule to repress the immune system. An "individual" according to any of the above embodiments may be a mammal, for example a human. "Repression of the immune system" according to any of the above embodiments may include any one or more of a general decrease in immune function, a decrease in T cell function, a decrease in B cell function, a decrease in T cell responsiveness, and the like.

In certain embodiments the disease to be treated is an autoimmune disease. The CD20-PD1 binding molecules may be used in eliminating cells involved in immune cell-mediated disorders, autoimmunity, transplantation rejection, and graft-versus-host disease. A skilled artisan readily recognizes that in many cases the CD20-PD1 binding molecules may not provide a cure but may only provide partial benefit. In some embodiments, a physiological change having some benefit is also considered therapeutically beneficial. Thus, in some embodiments, an amount of CD20-PD1 binding molecule that provides a physiological change is considered an "effective amount" or a "therapeutically effective amount". The subject, patient, or individual in need of treatment is typically a mammal, more specifically a human.

For the prevention or treatment of disease, the appropriate dosage of a CD20-PD1 binding molecule of the disclosure (when used alone or in combination with one or more other additional therapeutic agents) will depend on the type of disease to be treated, the route of administration, the body weight of the patient, the particular CD20-PD1 binding molecule, the severity and course of the disease, whether the antibody is administered for preventive or therapeutic purposes, previous or concurrent therapeutic interventions, the patient's clinical history and response to the CD20-PD1 binding molecule, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The CD20-PD1 binding molecule is suitably administered to the patient at one time or over a series of treatments. Depending on the type and severity of the disease, about 1 µg/kg to 15 mg/kg (e.g., 0.1 mg/kg-10 mg/kg) of CD20-PD1 binding molecule can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the CD20-PD1 binding molecule would be in the range from about 0.005 mg/kg to about 10 mg/kg. In other non-limiting examples, a dose may also comprise from about 1 µg/kg/body weight, about 5 µg/kg/body weight, about 10 µg/kg/body weight, about 50 µg/kg/body weight, about 100 µg/kg/body weight, about 200 µg/kg/body weight, about 350 µg/kg/body weight, about 500 µg/kg/body weight, about 1 mg/kg/body weight, about 5 mg/kg/body weight, about 10 mg/kg/body weight, about 50 mg/kg/body weight, about 100 mg/kg/body weight, about 200 mg/kg/body weight, about 350 mg/kg/body weight, about 500 mg/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 µg/kg/body weight to about 500 mg/kg/body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g., every week or every three weeks (e.g., such that the patient receives from about two to about twenty, or e.g., about six doses of the CD20-PD1 binding molecule). An initial higher loading dose, followed by one or more lower doses may be administered. However, other dosage regimens may be useful. The progress of this therapy is easily monitored by conventional techniques and assays.

The CD20-PD1 binding molecules of the disclosure will generally be used in an amount effective to achieve the intended purpose. For use to treat or prevent a disease condition, the CD20-PD1 binding molecules of the disclosure, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $EC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the CD20-PD1 binding molecules which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by ELISA HPLC.

In cases of local administration or selective uptake, the effective local concentration of the CD20-PD1 binding molecules may not be related to plasma concentration. One having skill in the art will be able to optimize therapeutically effective local dosages without undue experimentation.

A therapeutically effective dose of the CD20-PD1 binding molecules described herein will generally provide therapeutic benefit without causing substantial toxicity. Toxicity and therapeutic efficacy of a CD20-PD1 binding molecule can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. CD20-PD1 binding molecules that exhibit large therapeutic indices are preferred. In one embodiment, the CD20-PD1 binding molecule according to the present disclosure exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition. (See, e.g., Fingl et al., 1975, In: The Pharmacological Basis of Therapeutics, Ch. 1, p. 1, incorporated herein by reference in its entirety).

The attending physician for patients treated with CD20-PD1 binding molecules of the disclosure would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

6.10.1. Type 1 Diabetes

In some embodiments, CD20-PD1 binding molecules according to the disclosure can prevent or slow the development or progression of Type 1 Diabetes. Thus, in some embodiments, the CD20-PD1 binding molecules, nucleic acids, and/or pharmaceutical compositions of the disclosure can be administered to a subject having T1D or at risk of developing T1D. Risk factors for developing T1D include, but are not limited to, genetic markers (e.g., human leukocyte antigen (HLA) complexes; see, Flemming and Pociot, 2016, Lancet, 387(10035):2331-2339), viral infection (e.g., German measles, coxsackie virus, and mumps), race/ethnicity (e.g., in the United States, Caucasians are more susceptible to type 1 diabetes), family history, early diet, and presence of other autoimmune conditions (e.g., Grave's disease, multiple sclerosis, pernicious anemia). Cancer patients receiving immune checkpoint inhibitor therapies are also at risk of developing T1D as well. See de Filette et al., 2019, Eur J Endocrinol, 181(3):363-374. It is within the purview of those skilled in the art to identify and select those individuals at risk of developing T1D.

In some embodiments, a patient at risk of developing T1D is treated with CD20-PD1 binding molecules, nucleic acids, and/or pharmaceutical compositions of the disclosure in accordance with the methods of the disclosure.

6.11. Combination Therapy

The CD20-PD1 binding molecules according to the disclosure may be administered in combination with one or more other agents in therapy. For instance, a CD20-PD1 binding molecule of the disclosure may be co-administered with at least one additional therapeutic agent. The term "therapeutic agent" encompasses any agent administered to treat a symptom or disease in a subject in need of such treatment. Such additional therapeutic agent may comprise any active ingredients suitable for the particular indication being treated, preferably those with complementary activities that do not adversely affect each other. In certain embodiments, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers.

Such other agents are suitably present in combination in amounts that are effective for the purpose intended. The effective amount of such other agents depends on the amount of CD20-PD1 binding molecule used, the type of disorder or treatment, and other factors discussed above. The CD20-PD1 binding molecules are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the CD20-PD1 binding molecule of the disclosure can occur prior to, simultaneously, and/or following, administration of the additional therapeutic agent and/or adjuvant.

6.11.1. Combination Therapy Using CD20-PD1 Binding Molecule Therapy and Immunotherapy The CD20-PD1 binding molecules of the disclosure can be advantageously used in combination with chimeric antigen receptor ("CAR")-expressing cells, e.g., CAR-expressing Treg ("CAR-Treg") cells, for example CAR-Treg in the treatment of autoimmune diseases. In some embodiments, the CAR-Treg cells are recognized by a CD20 targeting moiety in the CD20-PD1 binding molecule. The CD20 targeting moiety can recognize a Treg cell receptor or another cell surface molecule on the CAR-Treg cells. In some embodiments, a CD20 targeting moiety in the CD20-PD1 binding molecule is capable of binding to an extracellular domain of the CAR, for example the antigen binding domain. CAR-Treg cells are described in Fritsche et al., 2020, Trends Biotechnol, 38(10):1099-1112; Zhang et al., 2018, Front Immunol, 9:2359; and Mohseni et al., Front Immunol, 11:1608, each of which is incorporated by reference herein in its entirety.

6.12. Evaluation of CD20-PD1 Binding Molecules

Aspects of the present disclosure relate to a luciferase-based reporter bioassay to evaluate the ability of CD20-PD1 binding molecules disclosed herein to agonize PD1 on Jurkat cells in the presence of CD20 presented on HEK293 cells. In some embodiments, HEK293 cells are transduced with CD22 as well as with CD20.

In some embodiments, a bioassay disclosed herein includes the use of a bispecific antibody (such as CD3×CD22) in the presence of the HEK293 cells to elicit an immune response from a Jurkat cell line that has been transduced with AP1 (activator-protein 1)-luciferase reporter, CD3 and PD1 using lentivirus. The CD20-PD1 binding molecules are added to the wells in the presence of the Jurkat and HEK293 cells as well as the anti-CD3×CD22 bispecific antibody. The molecules that best agonize PD1 have the ability to reduce the amount of the immune response stimulated by the anti-CD3×CD22 bispecific antibody as measured by the AP1 driven luciferase activity.

7. EXAMPLES

7.1. Materials and Methods

7.1.1. Design and Production of CD20-PD1 Binding Molecules

Constructs encoding the bispecific CD20-PD1 agonists and control as set out in Tables 1 and 2 below were generated. The bispecific CD20-PD1 agonists included different configurations of murine anti-CD20 and a modified murine PDL1 ectodomain, an IgG1 effector null (EN) (L234A, L235E, G237A, A330S and P331S, EU numbering) domain, and linkers of different lengths from different repeats of $G_4S$ (SEQ ID NO: 14). A 29-amino acid signal sequence from murine inactive tyrosine-protein kinase transmembrane receptor ROR1 (mROR1) was added to the N-termini of the constructs. All bispecific CD20-PD1 agonists were expressed as preproteins containing the signal sequence. The signal sequence was cleaved by intracellular processing to produce a mature protein.

Knob-forming mutation: T366W (EU numbering).

Hole-forming mutations: T366S, L368A, and Y407V (EU numbering).

Star mutations: H435R and Y436F (EU numbering).

| | |
|---|---|
| Murine anti-CD20 (18B12) heavy chain VR: | QVQLQQPGAELVRPGTSVKLSCKASGYTFTSYWMHWIKQR PGQGLEWIGVIDPSDNYTKYNQKFKGKATLTVDTSSSTAY MQLSSLTSEDSAVYFCAREGYYGSSPWFAYWGQGTLVTVS S (SEQ ID NO: 30) |
| Murine anti-CD20 (18B12) light chain VR: | QIVMSQSPAILSASPGEKVTMTCRARSSVSYIHWYQQKPG SSPKPWIYATSNLASGVPGRFSGSGSGTSYSLTITRVEAE DAATYYCQQWSSKPPTFGGGTKLEIK SEQ ID NO: 31) |
| hIgG4s-Fc: Variant hIgG4 with IgG2-based hinge region (hIgG4E99-105 hIgG2_HingeC106-A115 hIgG4_CH2_CH3 G117-K237) | ESKYGPPCPPCPAPPVAGPSVFLFPPKPKDTLMISRTPEV TCVVVDVSQEDPEVQFNWYVDGVEVHNAKTKPREEQFNST YRVVSVLTVLHQDWLNGKEYKCKVSNKGLPSSIEKTISKA KGQPREPQVYTLPPSQEEMTKNQVSLTCLVKGFYPSDIAV EWESNGQPENNYKTTPPVLDSDGSFFLYSRLTVDKSRWQE GNVFSCSVMHEALHNHYTQKSLSLSLGK (SEQ ID NO: 32) |
| hIgG4s(Knob)-Fc Variant hIgG4 with IgG2-based hinge region and mutations to facilitate heterodimerization with hIgG4s (Knob)-Fc | ESKYGPPCPPCPAPPVAGPSVFLFPPKPKDTLMISRTPEV TCVVVDVSQEDPEVQFNWYVDGVEVHNAKTKPREEQFNST YRVVSVLTVLHQDWLNGKEYKCKVSNKGLPSSIEKTISKA KGQPREPQVYTLPPSQEEMTKNQVSLWCLVKGFYPSDIAV EWESNGQPENNYKTTPPVLDSDGSFFLYSRLTVDKSRWQE GNVFSCSVMHEALHNHYTQKSLSLSLGK (SEQ ID NO: 33) |

-continued

| hIgG4s(Hole-Star)-Fc Variant hIgG4 with IgG2-based hinge region and mutations to facilitate heterodimerization with hIgG4s (Hole-Star)-Fc | ESKYGPPCPPCPAPPVAGPSVFLFPPKPKDTLMISRTPEV TCVVVDVSQEDPEVQFNWYVDGVEVHNAKTKPREEQFNST YRVVSVLTVLHQDWLNGKEYKCKVSNKGLPSSIEKTISKA KGQPREPQVYTLPPSQEEMTKNQVSLSCAVKGFYPSDIAV EWESNGQPENNYKTTPPVLDSDGSFFLVSRLTVDKSRWQE GNVFSCSVMHEALHNRFTQKSLSLSPGK (SEQ ID NO: 34) |
| --- | --- |
| hIgG1EN-Fc Variant IgG1 with L234A, L235E, G237A, A330S and P331S (EU numbering) | DKTHTCPPCPAPEAEGAPSVFLFPPKPKDTLMISRTPEVT CVVVDVSHEDPEVKFNWYVDGVEVHNAKTKPREEQYNSTY RVVSVLTVLHQDWLNGKEYKCKVSNKALPSSIEKTISKAK GQPREPQVYTLPPSRDELTKNQVSLTCLVKGFYPSDIAVE WESNGQPENNYKTTPPVLDSDGSFFLYSKLTVDKSRWQQG NVFSCSVMHEALHNHYTQKSLSLSPGK (SEQ ID NO: 35) |
| hIgG1EN(Knob)-Fc Variant IgG1 with L234A, L235E, G237A, A330S and P331S (EU numbering), and mutations to facilitate heterodimerization with hIgG1EN (Knob) | DKTHTCPPCPAPEAEGAPSVFLFPPKPKDTLMISRTPEVT CVVVDVSHEDPEVKFNWYVDGVEVHNAKTKPREEQYNSTY RVVSVLTVLHQDWLNGKEYKCKVSNKALPSSIEKTISKAK GQPREPQVYTLPPCRDELTKNQVSLWCLVKGFYPSDIAVE WESNGQPENNYKTTPPVLDSDGSFFLYSKLTVDKSRWQQG NVFSCSVMHEALHNHYTQKSLSLSPGK (SEQ ID NO: 36) |
| hIgG1EN(Hole-Star)-Fc Variant IgG1 with L234A, L235E, G237A, A330S and P331S (EU numbering), and mutations to facilitate heterodimerization with hIgG1EN (Hole-Star) | DKTHTCPPCPAPEAEGAPSVFLFPPKPKDTLMISRTPEVT CVVVDVSHEDPEVKFNWYVDGVEVHNAKTKPREEQYNSTY RVVSVLTVLHQDWLNGKEYKCKVSNKALPSSIEKTISKAK GQPREPQVCTLPPSRDELTKNQVSLSCAVKGFYPSDIAVE WESNGQPENNYKTTPPVLDSDGSFFLVSKLTVDKSRWQQG NVFSCSVMHEALHNRFTQKSLSLSPGK (SEQ ID NO: 37) |
| G4S: | GGGGS (SEQ ID NO: 14) |

The constructs were expressed in Expi293F™ cells by transient transfection (Thermo Fisher Scientific). Proteins in Expi293F™ supernatant were purified using the Protein-Maker™ system (Protein BioSolutions, Gaithersburg, MD) with either HiTrap™ Protein G HP or MabSelect SuRe® pcc columns (Cytiva). After single step elution, the antibodies were neutralized, dialyzed into a final buffer of phosphate buffered saline (PBS) with 5% glycerol, aliquoted and stored at −80° C. For some constructs, an additional step of size-exclusion chromatography with HiPrep® 26/60 Sephacryl® S-200 column was used.

Figures 3A, 3B:
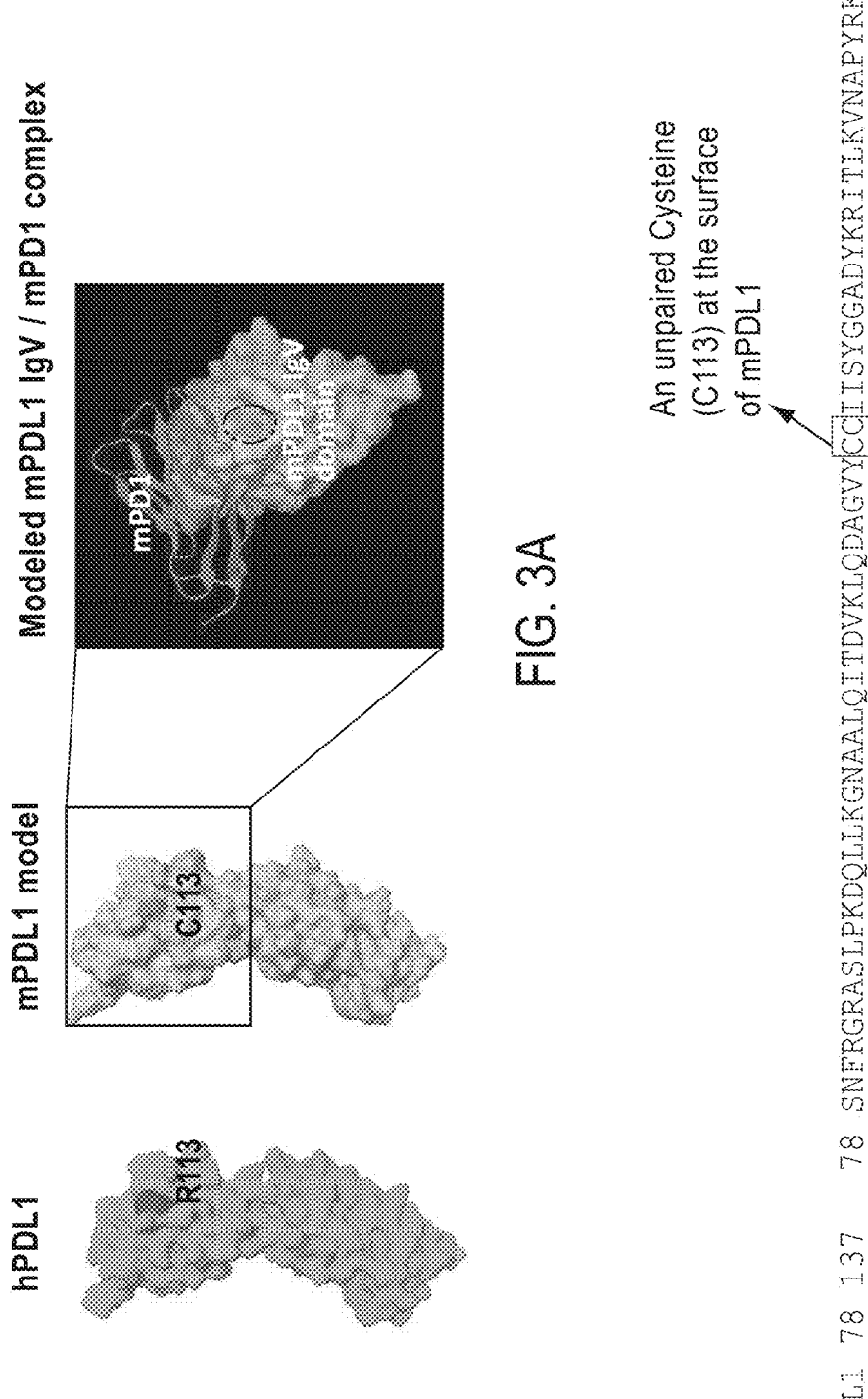
FIG. 3A depicts 3-dimensional models of hPDL1 (left) and mPDL1 (right), highlighting an unpaired cysteine residue (C113) at the surface of mPDL1.
FIG. 3B depicts a partial sequence alignment (78-137 aa) of mPDL1 (top sequence) and hPDL1 (bottom sequence). Figure discloses SEQ ID NOS: 54-55, respectively, in order of appearance.

Alignments and a selected mutated position in mPDL1 are depicted in FIG. 3B. Alignments between mPDL1 and hPDL1 were generated using MacVector. FIG. 3A depicts the 3-dimensional structure of mPDL1 and hPDL1, including a residue that was changed in mPDL1 to improve the yield and stability.

TABLE 3

Figure 2A:
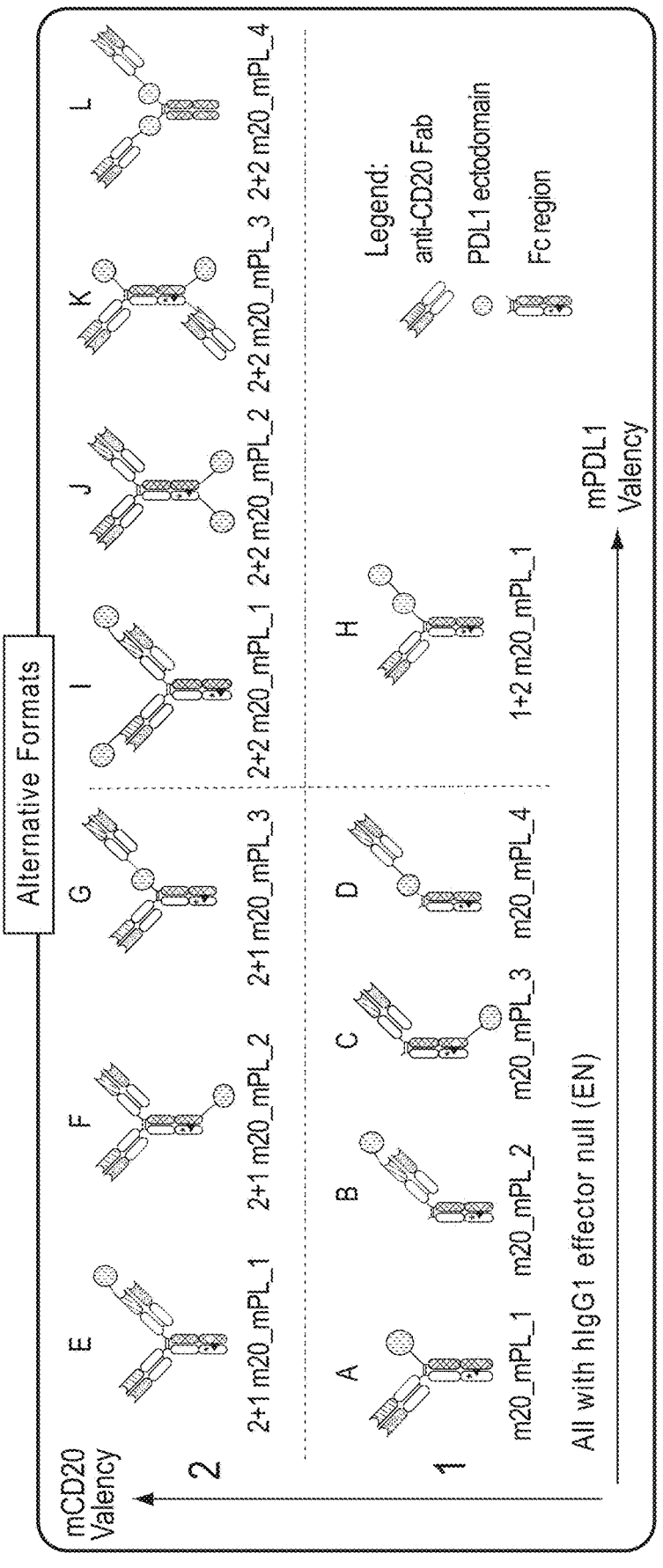
Figure 2B:
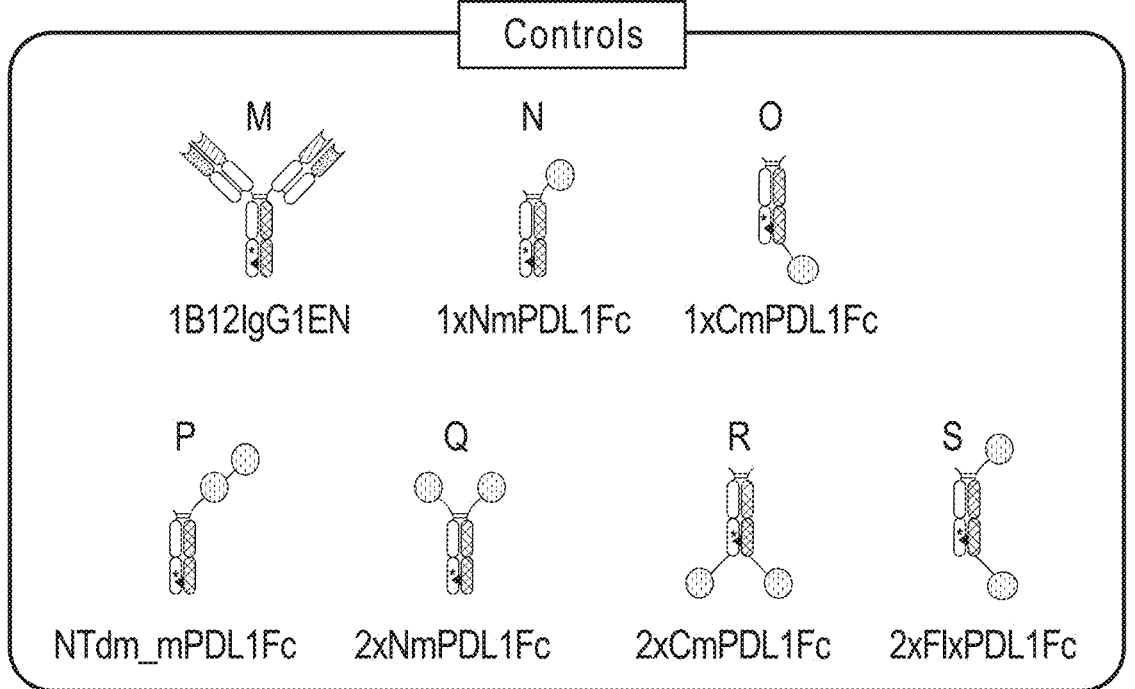

| anti-mCD20 x mPDL1 ectodomain constructs | | |
| --- | --- | --- |
| Molecule Chain | Description | Sequence |
| hIgG1EN-Fc (Hole-Star) | Variant IgG1 with L234A, L235E, G237A, A330S and P331S (EU numbering), and mutations to facilitate heterodimerization with hIgG1EN(Knob) Heterodimerize with: mPDL1 ectodomain-anti-mCD20-Fc to form m20_mPL_2 (FIG. 2A(B)); anti-mCD20-Fc-mPDL1 ectodomain to form m20_mPL_3 (FIG. 2A(C)); anti-mCD20-mPDL1 ectodomain-Fc to form m20_mPL_4 (FIG. 2A(D)); mPDL1 ectodomain-Fc to form 1xNmPDL1Fc (FIG. 2B(N)); Fc-mPDL1 ectodomain to form 1xCmPDL1Fc (FIG. 2B(O)); mPDL1 ectodomain-mPDL1 ectodomain-Fc to form NTdm_mPDL1Fc (FIG. | DKTHTCPPCPAPEAEGAPSVFLFPPKPKDTLMISRTPEVTCVVVDVSHEDPEVKF NWYVDGVEVHNAKTKPREEQYNSTYRVVSVLTVLHQDWLNGKEYKCKVSNKALPS SIEKTISKAKGQPREPQVCTLPPSRDELTKNQVSLSCAVKGFYPSDIAVEWESNG QPENNYKTTPPVLDSDGSFFLVSKLTVDKSRWQQGNVFSCSVMHEALHNRFTQKS LSLSPGK (SEQ ID NO: 37) |

TABLE 3-continued anti-mCD20 x mPDL1 ectodomain constructs

| Molecule Chain | Description | Sequence |
|---|---|---|
| | 2B(P)); or mPDL1 ectodomain-Fc-mPDL1 ectodomain to form 2xF1xPDL1Fc (FIG. 2B(S)) | |
| anti-mCD20-Fc (Hole-Star) | Anti-murine CD20 connected to the N-terminus of Fc Fc is hIgG1EN-Fc(Hole-Star) Heterodimerize with: mPDL1 ectodomain-Fc to form m20_mPL_1 (FIG. 2A(A)); mPDL1 ectodomain-anti-mCD20-Fc to form 2 + 1 m20_mPL_1 (FIG. 2A(E)); anti-mCD20-Fc-mPDL1 to form 2 + 1 m20_mPL_2 (FIG. 2A(F)); anti-mCD20-mPDL1 ectodomain-Fc to form 2 + 1 m20_mPL_3 (FIG. 2A(G)); or mPDL1-mPDL1-Fc to form 1 + 2 m20_mPL_1 (FIG. 2A(H)) | Anti-CD20 Heavy Chain VR+ hIgG1 CH1 + hIgG1EN Fc QVQLQQPGAELVRPGTSVKLSCKASGYTFTSYWMHWIKQRPGQGLEWIGVIDPSD NYTKYNQKFKGKATLTVDTSSSTAYMQLSSLTSEDSAVYFCAREGYYGSSPWFAY WGQGTLVTVSSASTKGPSVFPLAPSSKSTSGGTAALGCLVKDYFPEPVTVSWNSG ALTSGVHTFPAVLQSSGLYSLSSVVTVPSSSLGTQTYICNVNHKPSNTKVDKKVE PKSCDKTHTCPPCPAPEAEGAPSVFLFPPKPKDTLMISRTPEVTCVVVDVSHEDP EVKFNWYVDGVEVHNAKTKPREEQYNSTYRVVSVLTVLHQDWLNGKEYKCKVSNK ALPSSIEKTISKAKGQPREPQVCTLPPSRDELTKNQVSLSCAVKGFYPSDIAVEW ESNGQPENNYKTTPPVLDSDGSFFLVSKLTVDKSRWQQGNVFSCSVMHEALHNRF TQKSLSLSPGK (SEQ ID NO: 38) Anti-CD20 Light Chain VR+ hCKappa QIVMSQSPAILSASPGEKVTMTCRARSSVSYIHWYQQKPGSSPKPWIYATSNLAS GVPGRFSGSGSGTSYSLTITRVEAEDAATYYCQQWSSKPPTFGGGTKLEIKRTVA APSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC (SEQ ID NO: 39) |
| anti-mCD20-Fc(Hole-Star)-anti-mCD20 | A first anti-murine CD20 connected to the N-terminus of Fc, with a second anti-murine CD20 connected to the C-terminus of Fc Fc is hIgG1EN-Fc(Hole-Star) Heterodimerize with mPDL1-Fc-mPDL1 to form 2 + 2 m20_mPL_3 (FIG. 2A(K)) | Anti-CD20 Heavy Chain VR+ hIgG1 CH1 + hIgG1EN Fc + Anti-CD20 Heavy Chain VR+ hIgG1 CH1 QVQLQQPGAELVRPGTSVKLSCKASGYTFTSYWMHWIKQRPGQGLEWIGVIDPSD NYTKYNQKFKGKATLTVDTSSSTAYMQLSSLTSEDSAVYFCAREGYYGSSPWFAY WGQGTLVTVSSASTKGPSVFPLAPSSKSTSGGTAALGCLVKDYFPEPVTVSWNSG ALTSGVHTFPAVLQSSGLYSLSSVVTVPSSSLGTQTYICNVNHKPSNTKVDKKVE PKSCDKTHTCPPCPAPEAEGAPSVFLFPPKPKDTLMISRTPEVTCVVVDVSHEDP EVKFNWYVDGVEVHNAKTKPREEQYNSTYRVVSVLTVLHQDWLNGKEYKCKVSNK ALPSSIEKTISKAKGQPREPQVCTLPPSRDELTKNQVSLSCAVKGFYPSDIAVEW ESNGQPENNYKTTPPVLDSDGSFFLVSKLTVDKSRWQQGNVFSCSVMHEALHNRF TQKSLSLSPGKGGGGSGGGGSGGGGSQVQLQQPGAELVRPGTSVKLSCKASGYTF TSYWMHWIKQRPGQGLEWIGVIDPSDNYTKYNQKFKGKATLTVDTSSSTAYMQLS SLTSEDSAVYFCAREGYYGSSPWFAYWGQGTLVTVSSASTKGPSVFPLAPSSKST SGGTAALGCLVKDYFPEPVTVSWNSGALTSGVHTFPAVLQSSGLYSLSSVVTVPS SSLGTQTYICNVNHKPSNTKVDKKVEPKSCD (SEQ ID NO: 40) Anti-CD20 Light Chain VR+ hCKappa QIVMSQSPAILSASPGEKVTMTCRARSSVSYIHWYQQKPGSSPKPWIYATSNLAS GVPGRFSGSGSGTSYSLTITRVEAEDAATYYCQQWSSKPPTFGGGTKLEIKRTVA APSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC (SEQ ID NO: 39) |
| mPDL1 ectodomain-Fc(Knob) | Murine PDL1 (C113S) ectodomain connected to the N-terminus of Fc Fc is hIgG1EN-Fc(Knob) Heterodimerize with anti-mCD20-Fc to form m20_mPL_1 (FIG. 2A(A)); hIgG1EN-Fc(Hole-Star) to form 1xNmPDL1Fc (FIG. 2B(N)); or mPDL1 ectodomain-Fc(Hole-Star) to form 2xNmPDL1 Fc (FIG. 2B(Q)) | FTITAPKDLYVVEYGSNVTMECRFPVERELDLLALVVYWEKEDEQVIQFVAGEED LKPQHSNFRGRASLPKDQLLKGNAALQITDVKLQDAGVYSCIISYGGADYKRITL KVNAPYRKINQRISVDPATSEHELICQAEGYPEAEVIWTNSDHQPVSGKRSVTTS RTEGMLLNVTSSLRVNATANDVFYCTFWRSQPGQNHTAELIIPELPATHPPQNRT GGGGSDKTHTCPPCPAPEAEGAPSVFLFPPKPKDTLMISRTPEVTCVVVDVSHED PEVKFNWYVDGVEVHNAKTKPREEQYNSTYRVVSVLTVLHQDWLNGKEYKCKVSN KALPSSIEKTISKAKGQPREPQVYTLPPCRDELTKNQVSLWCLVKGFYPSDIAVE WESNGQPENNYKTTPPVLDSDGSFFLYSKLTVDKSRWQQGNVFSCSVMHEALHNH YTQKSLSLSPGK (SEQ ID NO: 41) |
| mPDL1 ectodomain-Fc(Hole-Star) | Murine PDL1 (C113S) ectodomain connected to the N-terminus of Fc Fc is hIgG1EN-Fc(Hole-Star) Heterodimerize with mPDL1 ectodomain-Fc(Knob) to form 2xNmPDL1Fc (FIG. 2B(Q)) | FTITAPKDLYVVEYGSNVTMECRFPVERELDLLALVVYWEKEDEQVIQFVAGEED LKPQHSNFRGRASLPKDQLLKGNAALQITDVKLQDAGVYSCIISYGGADYKRITL KVNAPYRKINQRISVDPATSEHELICQAEGYPEAEVIWTNSDHQPVSGKRSVTTS RTEGMLLNVTSSLRVNATANDVFYCTFWRSQPGQNHTAELIIPELPATHPPQNRT GGGGSDKTHTCPPCPAPEAEGAPSVFLFPPKPKDTLMISRTPEVTCVVVDVSHED PEVKFNWYVDGVEVHNAKTKPREEQYNSTYRVVSVLTVLHQDWLNGKEYKCKVSN KALPSSIEKTISKAKGQPREPQVCTLPPSRDELTKNQVSLSCAVKGFYPSDIAVE WESNGQPENNYKTTPPVLDSDGSFFLYSKLTVDKSRWQQGNVFSCSVMHEALHNR FTQKSLSLSPGK (SEQ ID NO: 42) |
| Fc(Knob)-mPDL1 ecto | Murine PDL1 (C113S) ectodomain connected to the C-terminus of Fc Fc is hIgG1EN-Fc(Knob) Heterodimerize with: | DKTHTCPPCPAPEAEGAPSVFLFPPKPKDTLMISRTPEVTCVVVDVSHEDPEVKF NWYVDGVEVHNAKTKPREEQYNSTYRVVSVLTVLHQDWLNGKEYKCKVSNKALPS SIEKTISKAKGQPREPQVYTLPPCRDELTKNQVSLWCLVKGFYPSDIAVEWESNG QPENNYKTTPPVLDSDGSFFLYSKLTVDKSRWQQGNVFSCSVMHEALHNHYTQKS LSLSPGKGGGGSGGGGSGGGGSFTITAPKDLYVVEYGSNVTMECRFPVERELDLL |

TABLE 3-continued anti-mCD20 x mPDL1 ectodomain constructs

| Molecule Chain | Description | Sequence |
|---|---|---|
| | hIgG1EN-Fc(Hole-Star) to form 1xCmPDL1Fc (FIG. 2B(O)); or Fc(Hole-Star)-mPDL1 ectodomain to form 2xCmPDL1Fc (FIG. 2B(R)) | ALVVYWEKEDEQVIQFVAGEEDLKPQHSNFRGRASLPKDQLLKGNAALQITDVKL QDAGVYSCIISYGGADYKRITLKVNAPYRKINQRISVDPATSEHELICQAEGYPE AEVIWTNSDHQPVSGKRSVTTSRTEGMLLNVTSSLRVNATANDVFYCTFWRSQPG QNHTAELIIPELPATHPPQNRT (SEQ ID NO: 43) |
| Fc(Hole-Star)-mPDL1 ecto | Murine PDL1 (C113S) ectodomain connected to the C-terminus of Fc Fc is hIgG1EN-Fc(Hole-Star) Heterodimerize with Fc(Knob)-mPDL1 ectodomain to form 2xCmPDL1Fc (FIG. 2B(R)) | DKTHTCPPCPAPEAEGAPSVFLFPPPKPKDTLMISRTPEVTCVVVDVSHEDPEVKF NWYVDGVEVHNAKTKPREEQYNSTYRVVSVLTVLHQDWLNGKEYKCKVSNKALPS SIEKTISKAKGQPREPQVCTLPPSRDELTKNQVSLSCAVKGFYPSDIAVEWESNG QPENNYKTTPPVLDSDGSFFLVSKLTVDKSRWQQGNVFSCSVMHEALHNRFTQKS LSLSPGKGGGGSGGGGSGGGGSFTITAPKDLYVVEYGSNVTMECRFPVERELDLL ALVVYWEKEDEQVIQFVAGEEDLKPQHSNFRGRASLPKDQLLKGNAALQITDVKL QDAGVYSCIISYGGADYKRITLKVNAPYRKINQRISVDPATSEHELICQAEGYPE AEVIWTNSDHQPVSGKRSVTTSRTEGMLLNVTSSLRVNATANDVFYCTFWRSQPG QNHTAELIIPELPATHPPQNRT (SEQ ID NO: 44) |
| mPDL1 ectodomain-Fc (Knob)-mPDL1 ectodomain | A first murine PDL1 (C113S) ectodomain connected to the N-terminus of Fc, with a second PDL1 (C113S) ectodomain connected to the C-terminus of Fc Fc is hIgG1EN-Fc(Knob) Heterodimerize with: anti-mCD20-Fc-anti-mCD20 (FIG. 2A(K)); or hIgG1EN-Fc(Hole-Star) to form 2xF1xPDL1Fc (FIG. 2B(S)) | FTITAPKDLYVVEYGSNVTMECRFPVERELDLLALVVYWEKEDEQVIQFVAGEED LKPQHSNFRGRASLPKDQLLKGNAALQITDVKLQDAGVYSCIISYGGADYKRITL KVNAPYRKINQRISVDPATSEHELICQAEGYPEAEVIWTNSDHQPVSGKRSVTTS RTEGMLLNVTSSLRVNATANDVFYCTFWRSQPGQNHTAELIIPELPATHPPQNRT GGGGSDKTHTCPPCPAPEAEGAPSVFLFPPPKPKDTLMISRTPEVTCVVVDVSHED PEVKFNWYVDGVEVHNAKTKPREEQYNSTYRVVSVLTVLHQDWLNGKEYKCKVSN KALPSSIEKTISKAKGQPREPQVYTLPPCRDELTKNQVSLWCLVKGFYPSDIAVE WESNGQPENNYKTTPPVLDSDGSFFLYSKLTVDKSRWQQGNVFSCSVMHEALHNH YTQKSLSLSPGKGGGGSGGGGSGGGGSFTITAPKDLYVVEYGSNVTMECRFPVER ELDLLALVVYWEKEDEQVIQFVAGEEDLKPQHSNFRGRASLPKDQLLKGNAALQI TDVKLQDAGVYSCIISYGGADYKRITLKVNAPYRKINQRISVDPATSEHELICQA EGYPEAEVIWTNSDHQPVSGKRSVTTSRTEGMLLNVTSSLRVNATANDVFYCTFW RSQPGQNHTAELIIPELPATHPPQNRT (SEQ ID NO: 45) |
| mPDL1 ectodomain-mPDL1 ectodomain-Fc(Knob) | A first mPDL1 (C113S) ectodomain connected to the N-terminus of a second mPDL1 ectodomain, with the second mPDL1 (C113S) ectodomain connected to the N-terminus of Fc Fc is hIgG1EN(Knob) Heterodimerize with: anti-mCD20-Fc to form 1 + 2 m20_mPL_1 (FIG. 2A(H)); or hIgG1EN-Fc(Hole-Star) to form NTdm_mPDL1Fc (FIG. 2B(P)) | FTITAPKDLYVVEYGSNVTMECRFPVERELDLLALVVYWEKEDEQVIQFVAGEED LKPQHSNFRGRASLPKDQLLKGNAALQITDVKLQDAGVYSCIISYGGADYKRITL KVNAPYRKINQRISVDPATSEHELICQAEGYPEAEVIWTNSDHQPVSGKRSVTTS RTEGMLLNVTSSLRVNATANDVFYCTFWRSQPGQNHTAELIIPELPATHPPQNRT GGGGSGGGGSGGGGSGGGGSGGGGSGGGGSFTITAPKDLYVVEYGSNVTMECRFP VERELDLLALVVYWEKEDEQVIQFVAGEEDLKPQHSNFRGRASLPKDQLLKGNAA LQITDVKLQDAGVYSCIISYGGADYKRITLKVNAPYRKINQRISVDPATSEHELI CQAEGYPEAEVIWTNSDHQPVSGKRSVTTSRTEGMLLNVTSSLRVNATANDVFYC TFWRSQPGQNHTAELIIPELPATHPPQNRTGGGGSDKTHTCPPCPAPEAEGAPSV FLFPPPKPKDTLMISRTPEVTCVVVDVSHEDPEVKFNWYVDGVEVHNAKTKPREEQ YNSTYRVVSVLTVLHQDWLNGKEYKCKVSNKALPSSIEKTISKAKGQPREPQVYT LPPCRDELTKNQVSLWCLVKGFYPSDIAVEWESNGQPENNYKTTPPVLDSDGSFF LYSKLTVDKSRWQQGNVFSCSVMHEALHNHYTQKSLSLSPGK (SEQ ID NO: 46) |
| mPDL1 ectodomain-anti-mCD20-Fc(Knob) | Murine PDL1 (C113S) ectodomain connected to the N-terminus of anti-murine CD20, with anti-murine CD20 connected to the N-terminus of Fc Fc is hIgG1EN(Knob) Heterodimerize with: hIgG1EN-Fc(Hole-Star) to form m20_mPL_2 (FIG. 2A(B); anti-mCD20-Fc to form 2 + 1 m20_mPL_1 (FIG. 2A(E)); or mPDL1 ectodomain-anti-mCD20-Fc(Hole-Star) to form 2 + 2 m20_mPL_1 (FIG. 2A(I)) | mPDL1 ectodomain + Anti-CD20 Heavy Chain VR+ hIgG1 CH1 + hIgG1EN FTITAPKDLYVVEYGSNVTMECRFPVERELDLLALVVYWEKEDEQVIQFVAGEED LKPQHSNFRGRASLPKDQLLKGNAALQITDVKLQDAGVYSCIISYGGADYKRITL KVNAPYRKINQRISVDPATSEHELICQAEGYPEAEVIWTNSDHQPVSGKRSVTTS RTEGMLLNVTSSLRVNATANDVFYCTFWRSQPGQNHTAELIIPELPATHPPQNRT GGGGSGGGGSGGGGSQVQLQQPGAELVRPGTSVKLSCKASGYTFTSYWMHWIKQR PGQGLEWIGVIDPSDNYTKYNQKFKGKATLTVDTSSSTAYMQLSSLTSEDSAVYF CAREGYYGSSPWFAYWGQGTLVTVSSASTKGPSVFPLAPSSKSTSGGTAALGCLV KDYFPEPVTVSWNSGALTSGVHTFPAVLQSSGLYSLSSVVTVPSSSLGTQTYICN VNHKPSNTKVDKKVEPKSCDKTHTCPPCPAPEAEGAPSVFLFPPPKPKDTLMISRT PEVTCVVVDVSHEDPEVKFNWYVDGVEVHNAKTKPREEQYNSTYRVVSVLTVLHQ DWLNGKEYKCKVSNKALPSSIEKTISKAKGQPREPQVYTLPPCRDELTKNQVSLW CLVKGFYPSDIAVEWESNGQPENNYKTTPPVLDSDGSFFLYSKLTVDKSRWQQGN VFSCSVMHEALHNHYTQKSLSLSPGK (SEQ ID NO: 47) Anti-CD20 Light Chain VR+ hCKappa QIVMSQSPAILSASPGEKVTMTCRARSSVSYIHWYQQKPGSSPKPWIYATSNLAS GVPGRFSGSGSGTSYSLTITRVEAEDAATYYCQQWSSKPPTFGGGTKLEIKRTVA APSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC (SEQ ID NO: 39) |
| mPDL1 ectodomain-anti-mCD20-Fc (Hole-Star) | Murine PDL1 (C113S) ectodomain connected to the N-terminus of anti-murine CD20, with anti-murine CD20 connected to the N-terminus of Fc Fc is hIgG1EN(Hole-Star) Heterodimerize with mPDL1 | mPDL1 ectodomain + Anti-CD20 Heavy Chain VR+ hIgG1 CH1 + hIgG1EN FTITAPKDLYVVEYGSNVTMECRFPVERELDLLALVVYWEKEDEQVIQFVAGEED LKPQHSNFRGRASLPKDQLLKGNAALQITDVKLQDAGVYSCIISYGGADYKRITL KVNAPYRKINQRISVDPATSEHELICQAEGYPEAEVIWTNSDHQPVSGKRSVTTS RTEGMLLNVTSSLRVNATANDVFYCTFWRSQPGQNHTAELIIPELPATHPPQNRT GGGGSGGGGSGGGGSQVQLQQPGAELVRPGTSVKLSCKASGYTFTSYWMHWIKQR PGQGLEWIGVIDPSDNYTKYNQKFKGKATLTVDTSSSTAYMQLSSLTSEDSAVYF |

TABLE 3-continued anti-mCD20 x mPDL1 ectodomain constructs

| Molecule Chain | Description | Sequence |
|---|---|---|
| | ectodomain-anti-mCD20-Fc(Knob) to form 2 + 2 m20_mPL_1 (FIG. 2A(I)) | CAREGYYGSSPWFAYWGQGTLVTVSSASTKGPSVFPLAPSSKSTSGGTAALGCLV KDYFPEPVTVSWNSGALTSGVHTFPAVLQSSGLYSLSSVVTVPSSSLGTQTYICN VNHKPSNTKVDKKVEPKSCDKTHTCPPCPAPEAEGAPSVFLFPPKPKDTLMISRT PEVTCVVVDVSHEDPEVKFNWYVDGVEVHNAKTKPREEQYNSTYRVVSVLTVLHQ DWLNGKEYKCKVSNKALPSSIEKTISKAKGQPREPQVCTLPPSRDELTKNQVSLS CAVKGFYPSDIAVEWESNGQPENNYKTTPPVLDSDGSFFLVSKLTVDKSRWQQGN VFSCSVMHEALHNRFTQKSLSLSPGK (SEQ ID NO: 48)<br>Anti-CD20 Light Chain VR+ hCKappa<br>QIVMSQSPAILSASPGEKVTMTCRARSSVSYIHWYQQKPGSSPKPWIYATSNLAS GVPGRFSGSGSGTSYSLTITRVEAEDAATYYCQQWSSKPPTFGGGTKLEIKRTVA APSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC (SEQ ID NO: 39) |
| anti-mCD20-Fc(Knob)-mPDL1 ecto | Anti-murine CD20 connected to the N-terminus of Fc, with murine PDL1 (C113S) ectodomain connected to the C-terminus of Fc<br>Fc is hIgG1EN(Knob)<br>Heterodimerize with: hIgG1EN-Fc(Hole-Star) to form m20_mPL_3 (FIG. 2A(C));<br>anti-mCD20-Fc to form 2 + 1 m20_mPL_2 (FIG. 2A(F)); or anti-mCD20-Fc-mPDL1 ectodomain to form 2 + 2 m20_mPL_2 (FIG. 2A(J)) | Anti-CD20 Heavy Chain VR+ hIgG1 CH1 + hIgG1EN + mPDL1 ecto<br>QVQLQQPGAELVRPGTSVKLSCKASGYTFTSYWMHWIKQRPGQGLEWIGVIDPSD NYTKYNQKFKGKATLTVDTSSSTAYMQLSSLTSEDSAVYFCAREGYYGSSPWFAY WGQGTLVTVSSASTKGPSVFPLAPSSKSTSGGTAALGCLVKDYFPEPVTVSWNSG ALTSGVHTFPAVLQSSGLYSLSSVVTVPSSSLGTQTYICNVNHKPSNTKVDKKVE PKSCDKTHTCPPCPAPEAEGAPSVFLFPPKPKDTLMISRTPEVTCVVVDVSHEDP EVKFNWYVDGVEVHNAKTKPREEQYNSTYRVVSVLTVLHQDWLNGKEYKCKVSNK ALPSSIEKTISKAKGQPREPQVYTLPPCRDELTKNQVSLWCLVKGFYPSDIAVEW ESNGQPENNYKTTPPVLDSDGSFFLYSKLTVDKSRWQQGNVFSCSVMHEALHNHY TQKSLSLSPGKGGGGSGGGGSGGGGSFTITAPKDLYVVEYGSNVTMECRFPVERE LDLLALVVYWEKEDEQVIQFVAGEEDLKPQHSNFRGRASLPKDQLLKGNAALQIT DVKLQDAGVYSCIISYGGADYKRITLKVNAPYRKINQRISVDPATSEHELICQAE GYPEAEVIWTNSDHQPVSGKRSVTTSRTEGMLLNVTSSLRVNATANDVFYCTFWR SQPGQNHTAELIIPELPATHPPQNRT (SEQ ID NO: 49)<br>Anti-CD20 Light Chain VR+ hCKappa<br>QIVMSQSPAILSASPGEKVTMTCRARSSVSYIHWYQQKPGSSPKPWIYATSNLAS GVPGRFSGSGSGTSYSLTITRVEAEDAATYYCQQWSSKPPTFGGGTKLEIKRTVA APSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC (SEQ ID NO: 39) |
| anti-mCD20-Fc(Hole-Star)-mPDL1 ecto | Anti-murine CD20 connected to the N-terminus of Fc, with murine PDL1 ectodomain connected to the C-terminus of Fc<br>Fc is hIgG1EN(Hole-Star)<br>Heterodimerize with anti-mCD20-Fc(Knob)-mPDL1 ectodomain to form 2 + 2 m20_mPL_2 (FIG. 2A(J)) | Anti-CD20 Heavy Chain VR+ hIgG1 CH1 + hIgG1EN + mPDL1 ecto<br>QVQLQQPGAELVRPGTSVKLSCKASGYTFTSYWMHWIKQRPGQGLEWIGVIDPSD NYTKYNQKFKGKATLTVDTSSSTAYMQLSSLTSEDSAVYFCAREGYYGSSPWFAY WGQGTLVTVSSASTKGPSVFPLAPSSKSTSGGTAALGCLVKDYFPEPVTVSWNSG ALTSGVHTFPAVLQSSGLYSLSSVVTVPSSSLGTQTYICNVNHKPSNTKVDKKVE PKSCDKTHTCPPCPAPEAEGAPSVFLFPPKPKDTLMISRTPEVTCVVVDVSHEDP EVKFNWYVDGVEVHNAKTKPREEQYNSTYRVVSVLTVLHQDWLNGKEYKCKVSNK ALPSSIEKTISKAKGQPREPQVCTLPPSRDELTKNQVSLSCAVKGFYPSDIAVEW ESNGQPENNYKTTPPVLDSDGSFFLVSKLTVDKSRWQQGNVFSCSVMHEALHNRF TQKSLSLSPGKGGGGSGGGGSGGGGSFTITAPKDLYVVEYGSNVTMECRFPVERE LDLLALVVYWEKEDEQVIQFVAGEEDLKPQHSNFRGRASLPKDQLLKGNAALQIT DVKLQDAGVYSCIISYGGADYKRITLKVNAPYRKINQRISVDPATSEHELICQAE GYPEAEVIWTNSDHQPVSGKRSVTTSRTEGMLLNVTSSLRVNATANDVFYCTFWR SQPGQNHTAELIIPELPATHPPQNRT (SEQ ID NO: 50)<br>Anti-CD20 Light Chain VR+ hCKappa<br>QIVMSQSPAILSASPGEKVTMTCRARSSVSYIHWYQQKPGSSPKPWIYATSNLAS GVPGRFSGSGSGTSYSLTITRVEAEDAATYYCQQWSSKPPTFGGGTKLEIKRTVA APSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC (SEQ ID NO: 39) |
| anti-mCD20-mPDL1 ectodomain-Fc(Knob) | Anti-murine CD20 connected to the N-terminus murine PDL1 (C113S) ectodomain, with PDL1 ectodomain connected to the N-terminus of Fc<br>Fc is hIgG1EN(Knob)<br>Heterodimerize with: hIgG1EN-Fc(Hole-Star) to form m20_mPL_4 (FIG. 2A(D)); or anti-mCD20-Fc to form 2 + 1 m20_mPL_3 (FIG. 2A(G)) | Anti-CD20 Heavy Chain VR+ hIgG1 CH1 + mPDL1 ectodomain + hIgG1EN<br>QVQLQQPGAELVRPGTSVKLSCKASGYTFTSYWMHWIKQRPGQGLEWIGVIDPSD NYTKYNQKFKGKATLTVDTSSSTAYMQLSSLTSEDSAVYFCAREGYYGSSPWFAY WGQGTLVTVSSASTKGPSVFPLAPSSKSTSGGTAALGCLVKDYFPEPVTVSWNSG ALTSGVHTFPAVLQSSGLYSLSSVVTVPSSSLGTQTYICNVNHKPSNTKVDKKVE PKSCDGGGGSGGGGSFTITAPKDLYVVEYGSNVTMECRFPVERELDLLALVVYWE KEDEQVIQFVAGEEDLKPQHSNFRGRASLPKDQLLKGNAALQITDVKLQDAGVYS CIISYGGADYKRITLKVNAPYRKINQRISVDPATSEHELICQAEGYPEAEVIWTN SDHQPVSGKRSVTTSRTEGMLLNVTSSLRVNATANDVFYCTFWRSQPGQNHTAEL IIPELPATHPPQNRTGGGGSDKTHTCPPCPAPEAEGAPSVFLFPPKPKDTLMISR TPEVTCVVVDVSHEDPEVKFNWYVDGVEVHNAKTKPREEQYNSTYRVVSVLTVLH QDWLNGKEYKCKVSNKALPSSIEKTISKAKGQPREPQVYTLPPCRDELTKNQVSL WCLVKGFYPSDIAVEWESNGQPENNYKTTPPVLDSDGSFFLYSKLTVDKSRWQQG NVFSCSVMHEALHNHYTQKSLSLSPGK (SEQ ID NO: 51)<br>Anti-CD20 Light Chain VR+ hCKappa<br>QIVMSQSPAILSASPGEKVTMTCRARSSVSYIHWYQQKPGSSPKPWIYATSNLAS GVPGRFSGSGSGTSYSLTITRVEAEDAATYYCQQWSSKPPTFGGGTKLEIKRTVA |

TABLE 3-continued

| anti-mCD20 x mPDL1 ectodomain constructs | | |
| --- | --- | --- |
| Molecule Chain | Description | Sequence |
| | | APSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC (SEQ ID NO: 39) |
| anti-mCD20-mPDL1 ectodomain-Fc | Anti-murine CD20 connected to the N-terminus murine PDL1 (C113S) ectodomain, with PDL1 ectodomain connected to the N-terminus of Fc<br>Fc is hIgG1EN<br>Can homodimerize to form 2 + 2 m20_mPL_4 (FIG. 2A(L)) | Anti-CD20 Heavy Chain VR+ hIgG1 CH1 + mPDL1 ectodomain + hIgG1EN<br>QVQLQQPGAELVRPGTSVKLSCKASGYTFTSYWMHWIKQRPGQGLEWIGVIDPSD NYTKYNQKFKGKATLTVDTSSSTAYMQLSSLTSEDSAVYFCAREGYYGSSPWFAY WGQGTLVTVSSASTKGPSVFPLAPSSKSTSGGTAALGCLVKDYFPEPVTVSWNSG ALTSGVHTFPAVLQSSGLYSLSSVVTVPSSSLGTQTYICNVNHKPSNTKVDKKVE PKSCDGGGGSGGGGSFTITAPKDLYVVEYGSNVTMECRFPVERELDLLALVVYWE KEDEQVIQFVAGEEDLKPQHSNFRGRASLPKDQLLKGNAALQITDVKLQDAGVYS CIISYGGADYKRITLKVNAPYRKINQRISVDPATSEHELICQAEGYPEAEVIWTN SDHQPVSGKRSVTTSRTEGMLLNVTSSLRVNATANDVFYCTFWRSQPGQNHTAEL IIPELPATHPPQNRTGGGGSDKTHTCPPCPAPEAEGAPSVFLFPPKPKDTLMISR TPEVTCVVVDVSHEDPEVKFNWYVDGVEVHNAKTKPREEQYNSTYRVVSVLTVLH QDWLNGKEYKCKVSNKALPSSIEKTISKAKGQPREPQVYTLPPSRDELTKNQVSL TCLVKGFYPSDIAVEWESNGQPENNYKTTPPVLDSDGSFFLYSKLTVDKSRWQQG NVFSCSVMHEALHNHYTQKSLSLSPGK (SEQ ID NO: 52)<br>Anti-CD20 Light Chain VR+ hCKappa<br>QIVMSQSPAILSASPGEKVTMTCRARSSVSYIHWYQQKPGSSPKPWIYATSNLAS GVPGRFSGSGSGTSYSLTITRVEAEDAATYYCQQWSSKPPTFGGGTKLEIKRTVA APSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC (SEQ ID NO: 39) |
| anti-mCD20 (18B12)- Fc(Knob) | 18B12 connected to the N-terminus of Fc<br>Fc is hIgG1EN(Knob)<br>Can heterodimerize with anti-1B12-Fc(Hole-Star) to form 1B12IgG1EN (FIG. 2B(M)) | Anti-1B12 Heavy Chain VR+ hIgG1CH1 + hIgG1EN<br>QVQLQQPGAELVRPGTSVKLSCKASGYTFTSYWMHWIKQRPGQGLEWIGVIDPSD NYTKYNQKFKGKATLTVDTSSSTAYMQLSSLTSEDSAVYFCAREGYYGSSPWFAY WGQGTLVTVSSASTKGPSVFPLAPSSKSTSGGTAALGCLVKDYFPEPVTVSWNSG ALTSGVHTFPAVLQSSGLYSLSSVVTVPSSSLGTQTYICNVNHKPSNTKVDKKVE PKSCDKTHTCPPCPAPEAEGAPSVFLFPPPKPKDTLMISRTPEVTCVVVDVSHEDP EVKFNWYVDGVEVHNAKTKPREEQYNSTYRVVSVLTVLHQDWLNGKEYKCKVSNK ALPSSIEKTISKAKGQPREPQVYTLPPCRDELTKNQVSLWCLVKGFYPSDIAVEW ESNGQPENNYKTTPPVLDSDGSFFLYSKLTVDKSRWQQGNVFSCSVMHEALHNHY TQKSLSLSPGK (SEQ ID NO: 53)<br>Anti-CD20 Light Chain VR+ hCKappa<br>QIVMSQSPAILSASPGEKVTMTCRARSSVSYIHWYQQKPGSSPKPWIYATSNLAS GVPGRFSGSGSGTSYSLTITRVEAEDAATYYCQQWSSKPPTFGGGTKLEIKRTVA APSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC (SEQ ID NO: 39) |
| anti-mCD20 (18B12)- Fc(Hole-Star) | 18B12 connected to the N-terminus of Fc<br>Fc is hIgG1EN(Hole-Star)<br>Can heterodimerize with anti-1B12-Fc(Knob) to form 1B12IgG1EN (FIG. 2B(M)) | Anti-1B12 Heavy Chain VR+ hIgG1 CH1 + hIgG1EN<br>QVQLQQPGAELVRPGTSVKLSCKASGYTFTSYWMHWIKQRPGQGLEWIGVIDPSD NYTKYNQKFKGKATLTVDTSSSTAYMQLSSLTSEDSAVYFCAREGYYGSSPWFAY WGQGTLVTVSSASTKGPSVFPLAPSSKSTSGGTAALGCLVKDYFPEPVTVSWNSG ALTSGVHTFPAVLQSSGLYSLSSVVTVPSSSLGTQTYICNVNHKPSNTKVDKKVE PKSCDKTHTCPPCPAPEAEGAPSVFLFPPPKPKDTLMISRTPEVTCVVVDVSHEDP EVKFNWYVDGVEVHNAKTKPREEQYNSTYRVVSVLTVLHQDWLNGKEYKCKVSNK ALPSSIEKTISKAKGQPREPQVCTLPPSRDELTKNQVSLSCAVKGFYPSDIAVEW ESNGQPENNYKTTPPVLDSDGSFFLVSKLTVDKSRWQQGNVFSCSVMHEALHNRF TQKSLSLSPGK (SEQ ID NO: 38)<br>Anti-CD20 Light Chain VR+ hCKappa<br>QIVMSQSPAILSASPGEKVTMTCRARSSVSYIHWYQQKPGSSPKPWIYATSNLAS GVPGRFSGSGSGTSYSLTITRVEAEDAATYYCQQWSSKPPTFGGGTKLEIKRTVA APSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC (SEQ ID NO: 39) |

7.1.2. Flow Cytometry

Cells (HEK 293, MC38 over-expressing mCD20 or Jurkat over-expressing mPD1) were resuspended in FACS wash (PBS with 1% FBS) at $1 \times 10^6$ cells/mL. The staining was performed in $1 \times 10^5$ cells per well. The antibodies were diluted with a ratio of 1:5 from a starting concentration of $1.3 \times 10^{-07}$ M. The diluted antibodies were then added into the wells containing cells. Cells were stained for 30 min at 2-8° C. and washed twice with FACS wash buffer. APC-conjugated goat anti-human IgG (Jackson Immuno Research, 109-607-003, 1:400) was added to stain the cells for 30 min at 2-8° C. Following washing, cells were fixed in 2% paraformaldehyde for 30 min at 2-8° C. After two washes, stained cells were analyzed using BD LSR-Fortessa™ FACS instrument. The results were analyzed by FlowJo®. FSC/SSC gates were used to select mononuclear cells.

For spinal cord T cell infiltration flow cytometry analysis, single cell suspension of spinal cord were first prepared by collagenase D (Roche, 11088882001) digestion and Per-coll® (GE Healthcare, 17-0891-02) gradient separation. Cells were resuspended in FACS wash and stained following the protocol above with LIVE/DEAD™ Fixable Blue Dead Cell Stain Kit (Thermofisher Scientific, L34962), anti-mouse CD45-BV750 (BioLegend, 103157, 1:200 dilution), anti-mouse CD4-BUV563 (BD Bioscience, 612923, 1:200 dilution), and anti-mouse CD8a-BUV805 (BD Bioscience, 564920, 1:100 dilution). Cells were analyzed by BD FACSymphony® Cell Analyzer. The results were analyzed by OMIQ™ cytometry software.

7.1.3. Luciferase Reporter Assay: Anti-mCD20×mPDL1 Ectodomain Molecules

Figure 5A:
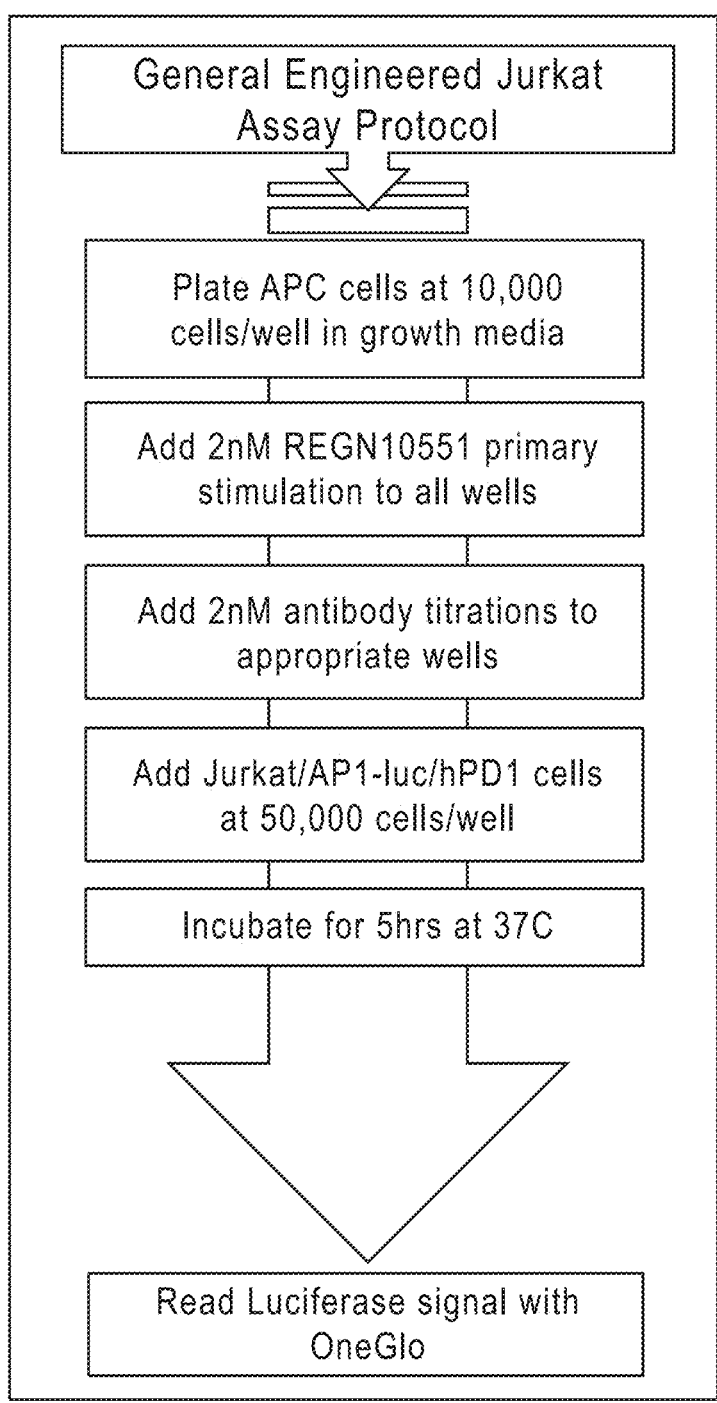
FIGS. 5A-5B depict the luciferase assay protocol.

A luciferase-based reporter assay was used to evaluate the ability of anti-mCD20×mPDL1 ectodomain molecules to agonize mouse PD1 (mPD1) on Jurkat cells in the presence of mouse CD20 (mCD20) presented on HEK293 cells. The overall design of the reporter assay is depicted in FIGS. 5A and B. AP1 is a transcription factor involved in the regulation of gene expression during T cell activation (Samelson 2002, PMID: 11861607). A bispecific antibody (bsAb) binding to human CD3 and CD22, CD3 bsAb (REGN10551), is used to stimulate T cell activation through engagement of antigen on target cells and receptor on T cells, similar to a previously described CD3×CD20 bsAb (Smith et al. 2015, PMID: 26659273). Engagement of mPD1 on Jurkat cells via mCD20-anchored mCD20×mPDL1 results in PD1 agonism-driven inhibition of luciferase signal.

7.1.3.1. Engineering of Jurkat/AP1-luc/mPD1 Cells

Jurkat/AP1-luc/mPD1 cells were generated by sequential transduction of Jurkat E6-1 cells (ATCC #TIB-152) with AP1 (activator-protein 1)-luciferase reporter lentivirus (QIAGEN CLS-011L) followed by mPD1 ORF-containing lentivirus (mPD1 NM_008798).

7.1.3.2. Engineering of HEK293/hCD22/mCD20 Cells

HEK293/hCD22/mCD20 cells were generated by sequential lentiviral transduction using human CD22 ORF-encoding lentivirus (NP_00762.2), followed by mCD20 ORF-encoding lentivirus (NP_031667.1).

7.1.3.3. Luciferase Assay Set Up

For the bioassay, HEK293/CD22/mCD20 target cells were seeded at 10,000 or 20,000 cells/well into 96-well plates in assay media (RPMI 1640 supplemented with 10% fetal bovine serum and L-glutamine-penicillin-streptomycin) and incubated overnight at 37° C. in 5% $CO_2$. The next day, Jurkat/AP1-luc/mPD1 reporter cells were added at 30,000 or 50,000 cells/well to wells containing the cultured target cells. Molecules of the present disclosure or control antibodies were then serially diluted in assay media 1:3 to final concentrations ranging from 100 nM to 1 pM (with an additional condition without test molecule) and added to the cells along with 1 nM or 2.5 nM of CD3 bsAb. To obtain a range of activation, CD3 bsAb was serially diluted 1:3 to final concentrations ranging from 100 nM to 1.69 pM (with an additional condition without bispecific mAb) and added to cells. After 5 hours of incubation at 37° C./5% $CO^2$, luciferase activity was detected on an Envision™ multilabel plate reader (PerkinElmer) after the addition of ONE-Glo™ (Promega) reagent. All conditions were tested in duplicate. The EC50/IC50 values were determined with GraphPad Prism™ software using nonlinear regression (4-parameter logistics). The percentage of inhibition was calculated based on the relative luminescence unit (RLU) values using the equation:

$$\% \text{ Inhibition} = 100 \times \frac{RLU_{Baseline} - RLU_{Inhibition}}{RLU_{Baseline} - RLU_{Background}}$$

In this equation "RLUBaseline" is the luminescence value from the cells treated with constant amount of CD3 bsAb without test molecule, "RLUInhibition" is the luminescence value at the highest concentration of test molecule with constant amount of CD3 bsAb, and "RLUBackground" is the luminescence value from cells without any CD3 bsAb or test molecules.

7.1.4. Determination of Oligomerization State of Anti-mCD20×mPDL1 Ectodomain Molecules by Size-Exclusion Chromatography Size-exclusion ultra-performance liquid chromatography (SE-UPLC) was employed to assess the size heterogeneity of anti-mCD20×mPDL1 ectodomain molecules. SE-UPLC analysis was conducted on a Waters Acquity® UPLC H-Class system where 10 µg of each protein sample was injected onto an Acquity® BEH SEC column (200 Å, 1.7 µm, 4.6×300 mm) and the flow rate was set at 0.3 mL/min. Mobile phase buffer contained 10 mM sodium phosphate, 500 mM NaCl, pH 7.0. Eluting samples were detected by UV absorbance at 280 nm using a photodiode array module.

7.1.5. Thermal Stability

Differential Scanning Fluorimetry (DSF) was employed to assess thermal stability of anti-mCD20×mPDL1 ectodomain molecules. DSF analysis was conducted on a ThermoFisher QuantStudio™ 5 system. Stock solutions of each sample were diluted to 0.2 mg/mL in 1×PBS-Glycerol pH 7.4 and transferred to a 96-well plate. An excess (8×) of Sypro Orange™ fluorescent dye, which preferentially binds to buried hydrophobic residues as a protein unfolds, was added to each well and thermal stability profiles were subsequently determined on a linear thermal ramp from 25° C. to 95° C. over 20 minutes.

7.1.6. Percent Assembly

The assembly of the bifunctional fusion molecules was assayed by high-throughput analysis on a Cliper LabChip GX™ as per the manufacturer's protocol (Perkin Elmer, Waltham, MA). Briefly, the sample buffer was prepared by mixing 7 ml of HT protein express sample buffer with either 240 µl BME (reducing) or 25 mM iodoacetamide (IAM, for non-reducing assay). Samples were normalized to 0.5 mg/ml with sample buffer and then heated at 70° C. for 10 minutes. 70 µl of water was added to each sample before loading onto the instrument. The chip was prepared according to the manufacturer's instruction. Electropherogram of the samples were analyzed using the LabChip GX software. Peaks from non-reduced electropherogram indicate the % intact antibody.

7.1.7. Activity of Anti-mCD20×mPDL1 Ectodomain Molecules in Pre-diabetic NOD Mice 10-week-old pre-diabetic Non-Obese Diabetic (NOD) mice (The Jackson Laboratory) were treated intraperitoneally twice per week with 1, 0.1, or 0.01 mg/kg of select anti-mCD20×mPDL1 ectodomain molecules for the duration of the experiment (e.g., until mice 28-weeks old). Blood glucose levels were monitored bi-weekly, while body weight was monitored weekly. The overall experimental design is depicted in FIG. 7.

7.1.8. Activity of Anti-mCD20×mPDL1 Ectodomain Molecules in Experimental Autoimmune Encephalomyelitis/Multiple Sclerosis Mouse Model Administration of immunodominant 35-55 epitope of myelin oligodendrocyte glycoprotein ($MOG_{35-55}$) in mice produces anti-MOG antibodies that cause demyelination and a chronic experimental autoimmune encephalomyelitis (EAE), which is a commonly used animal model of multiple sclerosis (MS).

EAE was induced in wildtype C57BL/6 mice (10-12 week, male, The Jackson Laboratory) by s.c. delivery of 200 mg $MOG_{35-55}$ in CFA on day 1. Given that administration of pertussis toxin facilitates migration of T cells to the central nervous system by weakening the blood-brain barrier, the mice were also i.p. injected with 200 ng pertussis toxin on day 1 and day 2. Body weight and EAE development was monitored on days 1, 2, 7, 10, 14, 18, and 20. EAE monitoring scores were recorded on a scale of 0-5 as follows: 0: healthy; 1: limp tail; 2: abnormal gait and/or righting reflex defect; 3: partial hindleg paralysis; 4: complete hindleg paralysis; and 5: complete hindleg and partial front leg paralysis or moribund.

Starting on day 2, mice were dosed with i.p. injections of select anti-mCD20×mPDL1 ectodomain molecules or appropriate control molecules twice per week. The endpoint tissue harvest was carried out at the peak of disease on day 20. Spinal cord infiltrates were used for flow cytometry and spleen MOG-specific T cell response was assessed with ELISPOT.

7.2. Example 1: Production and Stability of Bispecific Anti-mCD20-mPDL1 Ectodomain Agonists

7.2.1. Overview

Mammalian expression vectors for individual heavy chains and light chains were created by DNA synthesis and cloning in ready to use constructs in pcDNA™ 3.4 Topo™ expression system from Life Technologies (Carlsbad, CA). For expressing molecules, DNAs of heavy chains and universal light chain were co-transfected into Expi293™ cells (ThermoFisher Scientific) following the manufacturer's protocol. 50 ml of cell culture medium was harvested and processed for purification via a HiTrap® Protein A FF or Mab Select SuRe® column (GE Healthcare). For functional confirmation, selected MBMs were scaled up to 2 L and subject to a series of purification procedures including size exclusion chromatography as the final step.

7.2.2. Results

Various anti-mCD20×mPDL1 ectodomain molecules (FIG. 2A) were expressed and purified via one-step Mab-Select SuRe® column from Expi293™ Freestyle™ cells (Table 4), with the total yield ranges between 2.7-7.7 mg. In general, molecules with 1:1 valency ratio (anti mCD20: mPDL1 ecto) displayed higher yield (4.1-7.7 mg) than those with 2:1 or 2:2 (Table 4).

TABLE 4

| Production summary of anti-mCD20 × mPDL1 ectodomain fusion molecules | | | | | |
|---|---|---|---|---|---|
| Molecule ID (FIGS. 2A and 2B) | Molecule | Structural Format | Target Arrangement | MW (kDa) | Total yield (mg) from 50 ml |
| A | m20_mPL_1 | KiH-1 × N-Ligand | mPD1 × mCD20 | 123.2 | 5.5 |
| B | m20_mPL_2 | KiH-1 + N-Fusion | mPD1 – mCD20 | 123.8 | 7.7 |
| C | m20_mPL_3 | KiH-1 + C-Fusion | mCD20/mPD1 | 123.8 | 5.2 |
| D | m20_mPL_4 | KiH-1 + N-Fusion | mCD20 – mPDL1 | 100 | 4.1 |
| E | 2 + 1 m20_mPL_1 | KiH-2 + 1 N-Fusion | (mPD1 – mCD20) × mCD20 | 171.0 | 3.2 |
| F | 2 + 1 m20_mPL_2 | KiH-2 + 1 C-Fusion | (mCD20/mPD1) × mCD20 | 171.0 | 2.3 |
| G | 2 + 1 m20_mPL_3 | KiH-2 + 1 H-Fusion | (mCD20 – mPD1) × mCD20 | 171.1 | 2.9 |
| H | 1 + 2 m20_mPL_1 | KiH-1 × 1 + 1 N-Fusion | (mPD1 – mPD1) × mCD20 | 149.8 | 3.7 |
| I | 2 + 2 m20_mPL_1 | KiH-2 + 2 N-Fusion | (mPD1 – mCD20) × (mPD1 – mCD20) | 196.7 | 4.5 |
| J | 2 + 2 m20_mPL_2 | KiH-2 + 2 C-Fusion | (mCD20/mPD1) × (mCD20/mPD1) | 196.7 | 2.8 |
| K | 2 + 2 m20_mPL_3 | KiH-2 × 2 Fusion | (mPD1/mPD1) × (mCD20/mCD20) | 197.1 | 2.7 |
| L | 2 + 2 m20_mPL_4 | 2 + 2 H-Fusion | (mCD20 – mPD1) × (mCD20 – mPD1) | 200 | 19.2* |
| M | 1B12IgG1EN | IgG | mCD20 × mCD20 | 145.3 | 4.8 |
| N | 1 × NmPDL1Fc | KiH-N-Fusion | mPD1 | 76.0 | 11.2 |
| O | 1 × CmPDL1Fc | KiH-C-Fusion | mPD1 | 76.7 | 7.9 |
| P | NTdm_mPDL1Fc | KiH-N-Fusion | mPD1 – mPD1 | 125.8 | 5.2 |

TABLE 4-continued

| Production summary of anti-mCD20 × mPDL1 ectodomain fusion molecules | | | | | |
|---|---|---|---|---|---|
| Molecule ID (FIGS. 2A and 2B) | Molecule | Structural Format | Target Arrangement | MW (kDa) | Total yield (mg) from 50 ml |
| Q | 2 × NmPDL1Fc | Fusion-Fc | mPD1 × mPD1 | 101.1 | 10.0 |
| R | 2 × CmPDL1Fc | Fc-Fusion | mPD1 × mPD1 | 102.3 | 3.9 |
| S | 2 × Fl × PDL1Fc | KiH-2 × 0 Fusion | mPD1/mPD1 | 101.7 | 6.4 |

*Total yield from 200 ml culture after Protein A and size exclusion chromatography;
KiH: Knob-into-Hole;
x: Crossover between Hc:
–: Tandem fusion;
/: Separated by Fc After one step affinity purification, high molecular weight (HMVV) % and monomer % were examined by SE-UPLC, while thermal stability was monitored by Differential Scanning Fluorimetry (DSF) (Table 5). The majority of anti-mCD20×mPDL1 ectodomain fusion molecules displayed greater than 85% monomeric species without additional size exclusion chromatography (SEC) (Table 3, Molecules A-L in FIG. 1). For 2+2 m20_mPL_4 (L), after two column purification including an SEC step, the monomer percentage has increased to 99% (Table 5). All anti-mCD20×mPDL1 ectodomain fusions possessed similar thermal stability measured by DSF with Tm1 at around 60° C. (Table 3). Moreover, all bi-functional fusions had excellent assembly between heavy chains determined by capillary electrophoresis SDS (CE-SDS) (Table 5).

7.3.1. Results

Figure 4A:
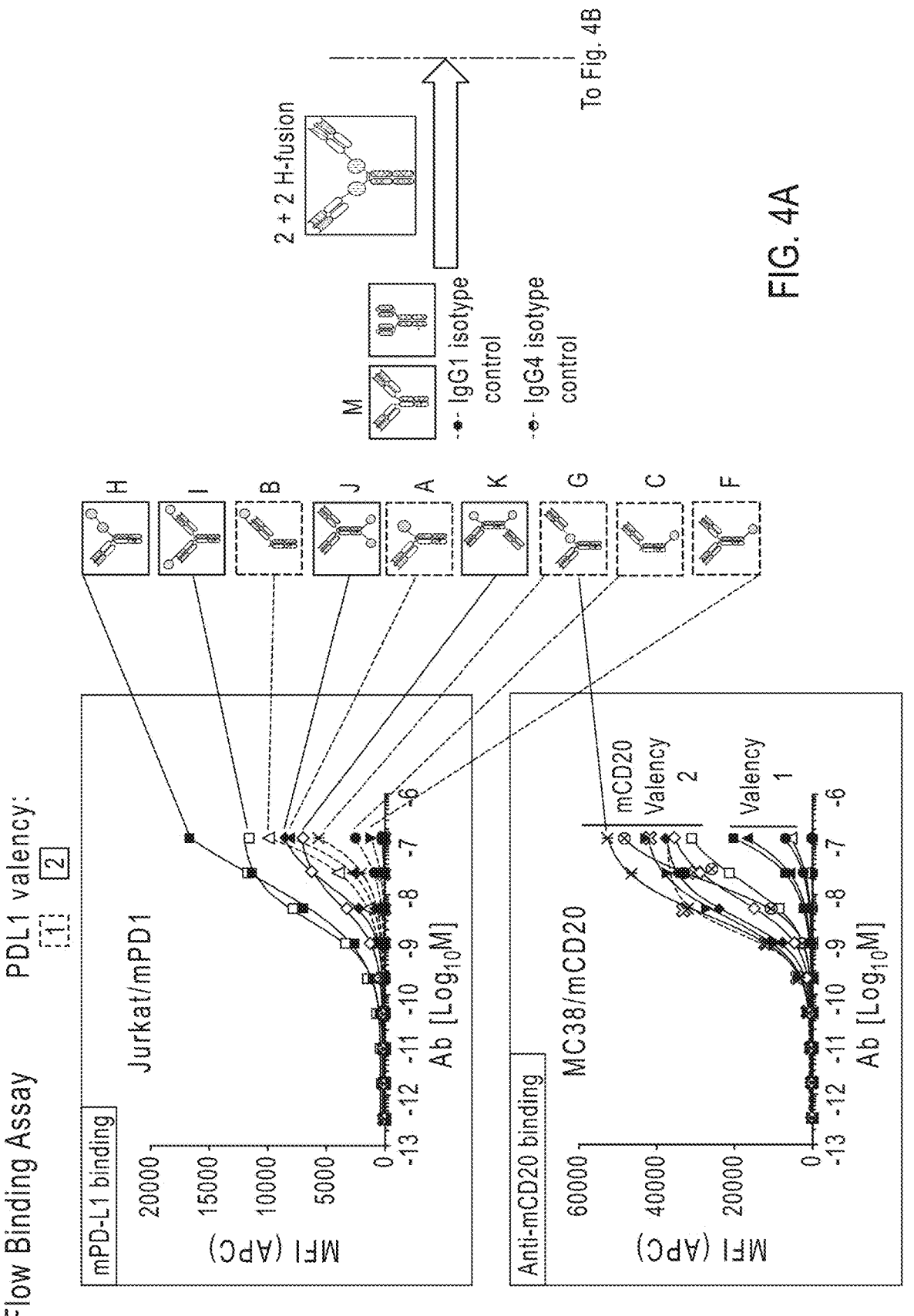
FIGS. 4A and 4B depict traces from flow binding studies and represent mPDL1 binding (top panels) or anti-mCD20 binding (bottom panels) by the indicated CD20-PD1 binding molecules (anti-mCD20×mPDL1 ectodomain) on Jurkat/mPD1 and MC38/mCD20 or HEK293/mCD20 cells, respectively.
Figure 4B:
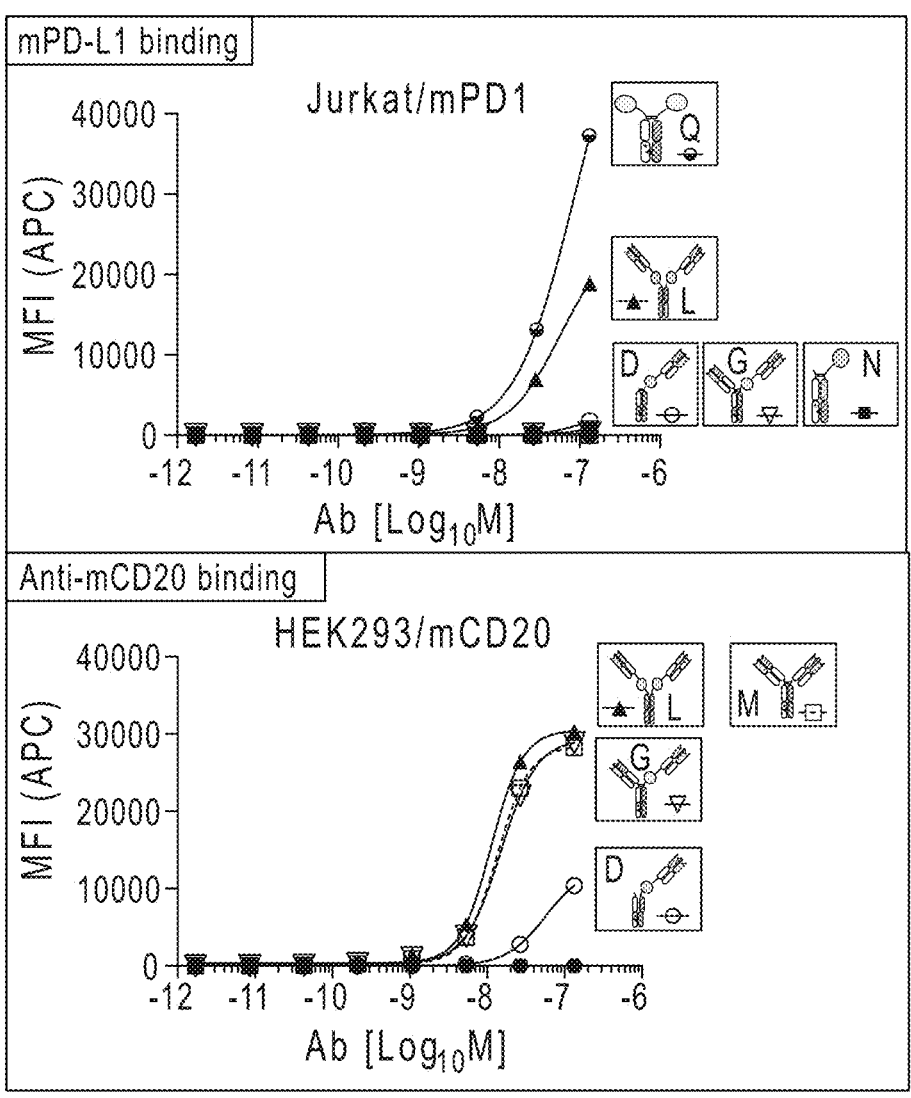

Binding curves are shown in FIGS. 4A and 4B. Higher potency and maximal MFI in binding were observed with bivalent molecules relative to monovalent molecules of similar format for both mPD1 and mCD20 binding. In particular, although 2+2 m20_mPL_4 (L) shared similar binding as 2+1 m20_mPL_3 (G) (FIGS. 4A and 4B; Table 6) to HEK293/mCD20 cells, 2+2 m20_mPL_4 (L) demonstrated stronger binding to Jurkat/mPD1 cells than 2+1 m20_mPL_3 (G) as a result of increased valency for mPD1 binding. Across both bivalent and monovalent molecules, binding signal appeared to be orientation-dependent, with

TABLE 5

| Monomeric purity (SE-UPLC), thermal stability (DSF) and assembly from 1-step purified anti mCD20 × mPDL1 ectodomain fusions and controls | | | | | | |
|---|---|---|---|---|---|---|
| Molecule ID | | SE-UPLC | | Thermal stability | | Caliper ce SDS |
| (FIGS. 2A and 2B) | Molecule | HMW % | Monomer % | Tm1 ° C. | Tm2 ° C. | Assembly % |
| A | m20_mPL_1 | 12 | 87 | 60.5 | NA | 100 |
| B | m20_mPL_2 | 15 | 80 | 61.5 | NA | 99 |
| C | m20_mPL_3 | 8 | 88 | 61.3 | NA | 99 |
| D | m20_mPL_4 | ND | ND | 61.6 | NA | 100 |
| E | 2 + 1 m20_mPL_1 | 14 | 74 | 62 | 85.4 | 95 |
| F | 2 + 1 m20_mPL_2 | 7 | 92 | 60.7 | 86.4 | 98 |
| G | 2 + 1 m20_mPL_3 | 11 | 86 | 61.2 | NA | 100 |
| H | 1 + 2 m20_mPL_1 | 8 | 86 | 61.6 | 85.6 | 100 |
| I | 2 + 2 m20_mPL_1 | 15 | 80 | 62.2 | 85.4 | 100 |
| J | 2 + 2 m20_mPL_2 | 7 | 91 | 61.3 | 85.5 | 98 |
| K | 2 + 2 m20_mPL_3 | 9 | 86 | 62.2 | 86.8 | 100 |
| L | 2 + 2 m20_mPL_4 | 1* | 99* | 59.7 | NA | 100 |
| M | 1B12lgG1EN | 10 | 83 | 58.5 | NA | 51 |
| N | 1xNmPDL1Fc | 6 | 91 | 59 | NA | 98 |
| O | 1xCmPDL1Fc | 4 | 93 | 60.6 | NA | 100 |
| P | NTdm_mPDL1Fc | 40 | 60 | 51.5 | NA | 62 |
| Q | 2xNmPDL1Fc | 5 | 92 | 59.2 | NA | 87 |
| R | 2xCmPDL1Fc | 3 | 95 | 60.5 | NA | 100 |
| S | 2xFlxPDL1Fc | 7 | 87 | 61.5 | NA | 100 |

ND: Not done.
NA: Not available
*Characterization from 200 ml culture after Protein A and SEC purification

7.3. Example 2: Binding Characterization of Anti-mCD20×mPDL1 Ectodomain Molecules The ability of anti-mCD20×mPDL1 ectodomain molecules to bind to their two targets on cell surface was assessed in a flow binding assay.

N-terminal anti-mCD20 and hPDL1 ectodomain orientation relative to Fc domain having generally higher potency and maximal MFI. Anti-mCD20 or mPDL1 ectodomain demonstrated reduced binding when positioned between an N-terminal moiety and the hinge region before Fc (FIGS. 4A and 4B; Table 6).

7.4. Example 3: mPDL1 Agonism by Anti-mCD20×mPDL1 Ectodomain Molecules

Figure 5B:
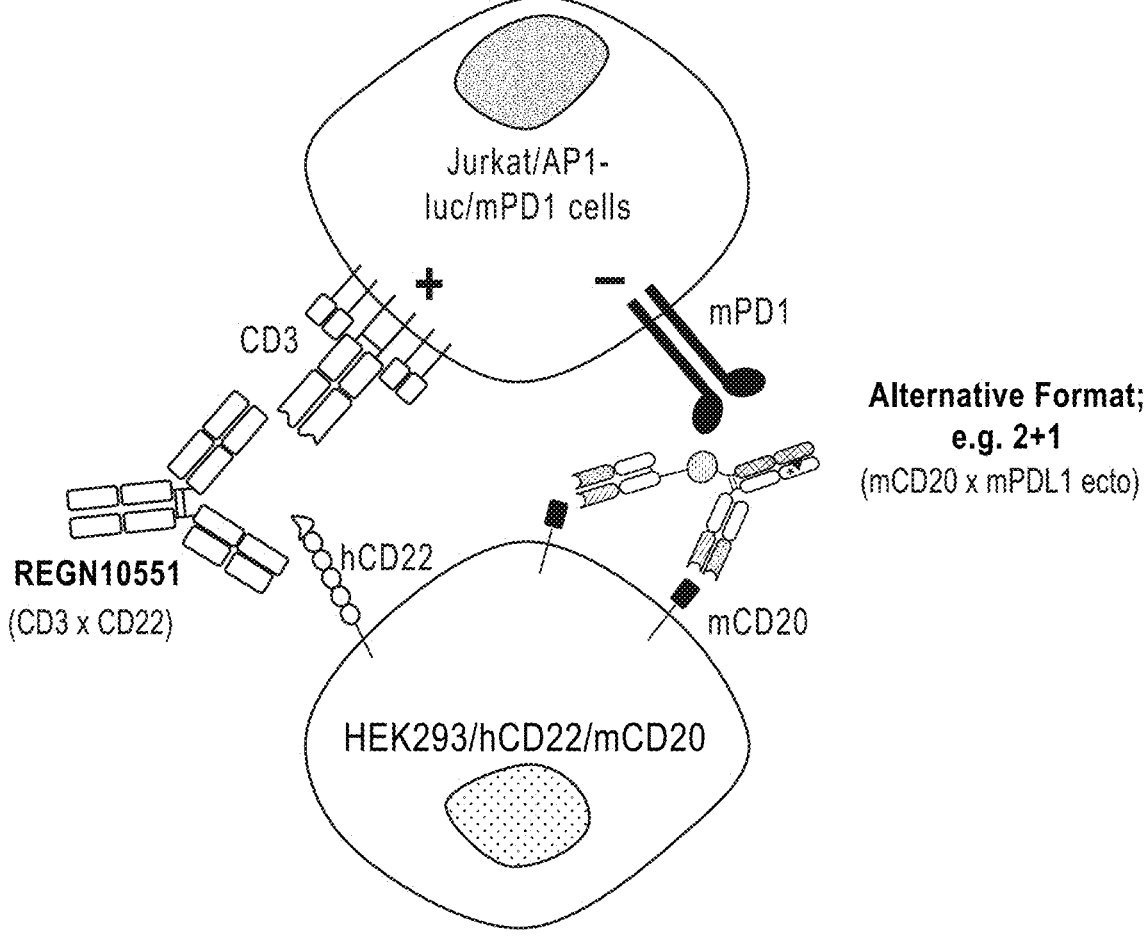

Utilizing the bioassay depicted in FIG. 5 and described in Section 7.1.3, mPD1 agonism by anti-mCD20×mPDL1 ectodomain molecules was studied.

7.4.1. Results

Figure 6A:
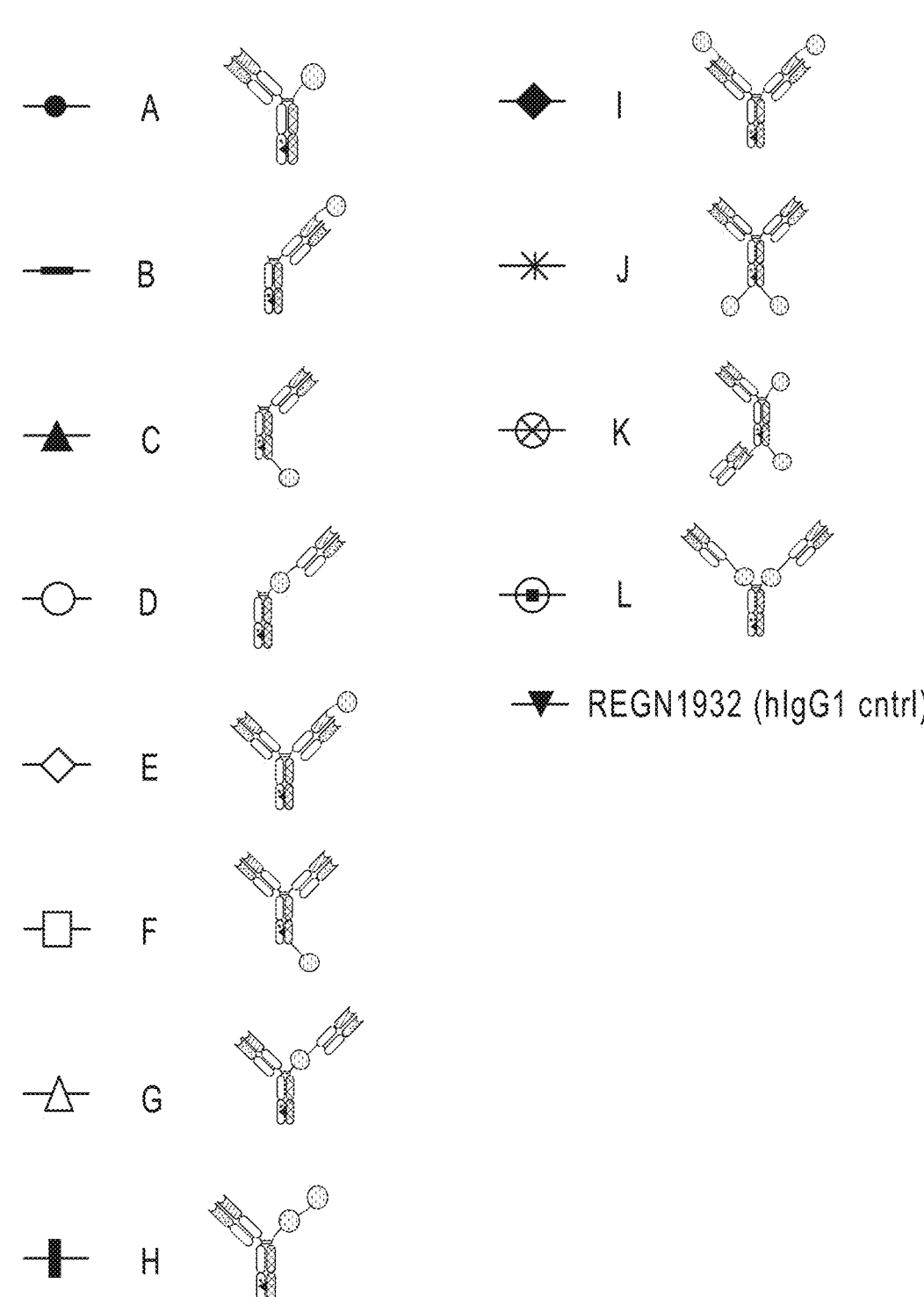
Figures 6B, 6C:
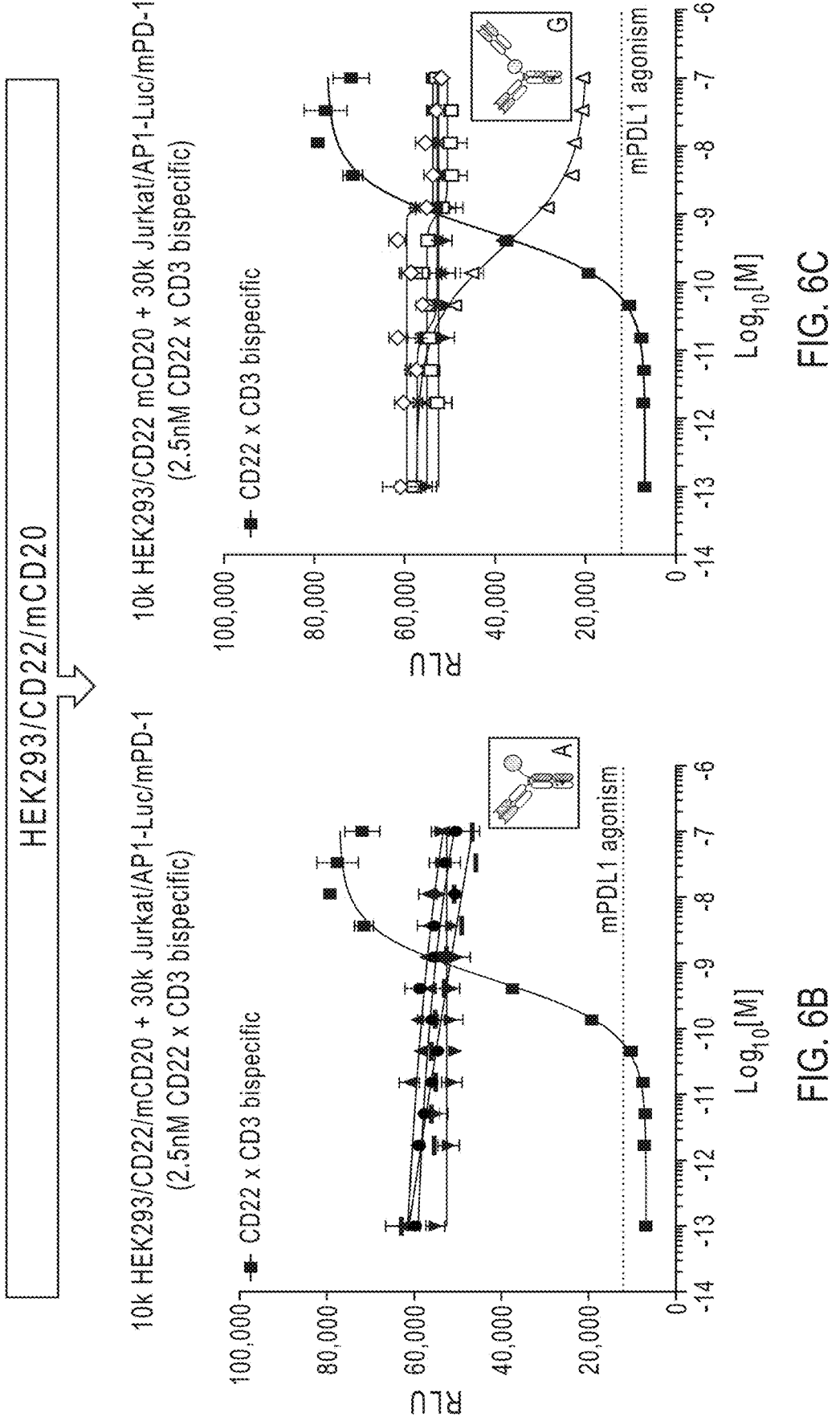
Figures 6D, 6E:
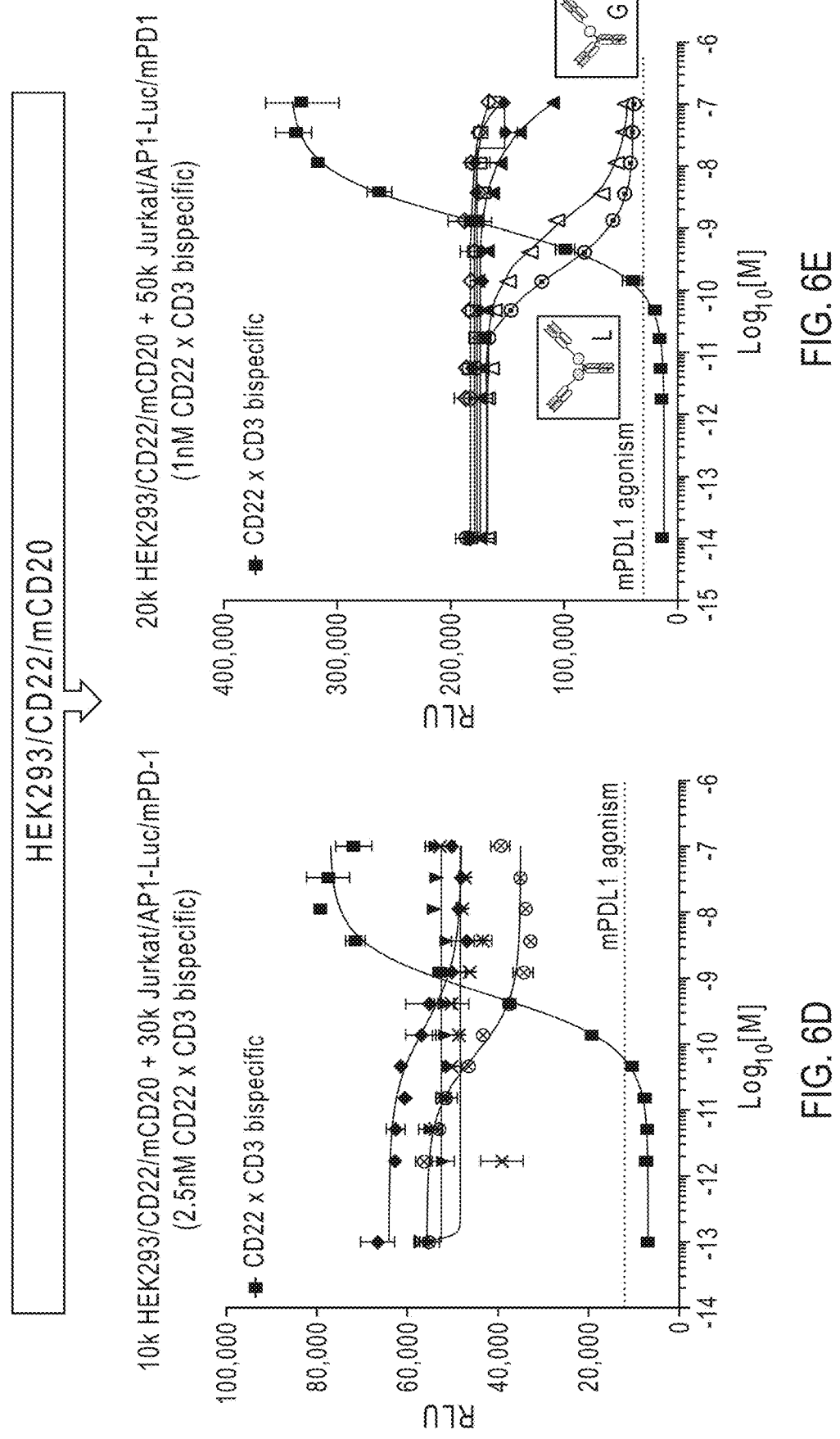
Figure 8A:
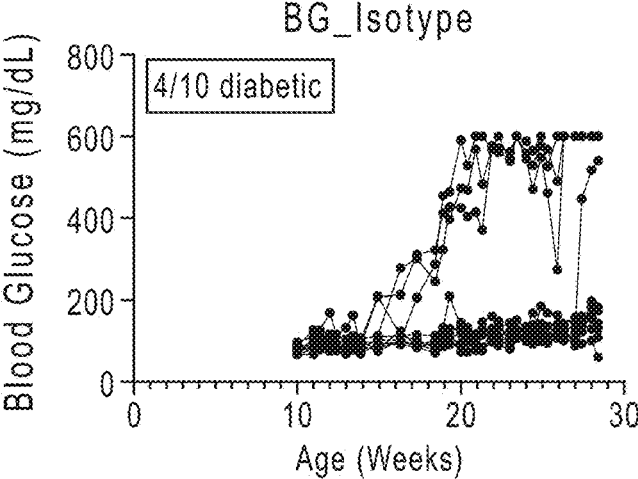
Figure 8B:
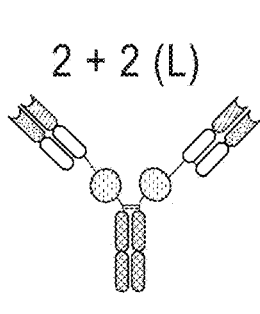
Figure 8B:
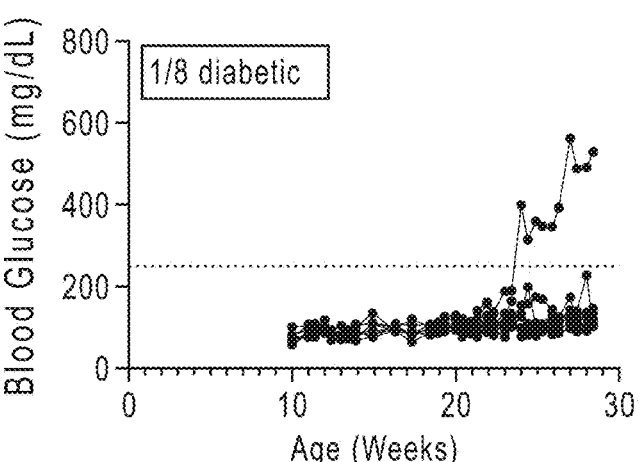
Figure 8C:
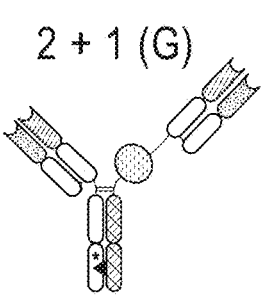
Figure 8C:
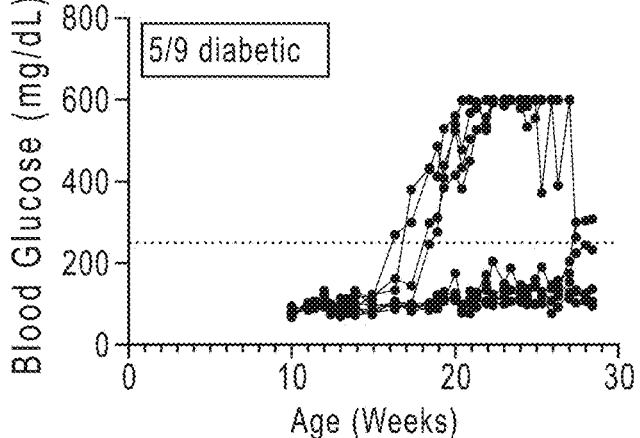
Figure 8D:
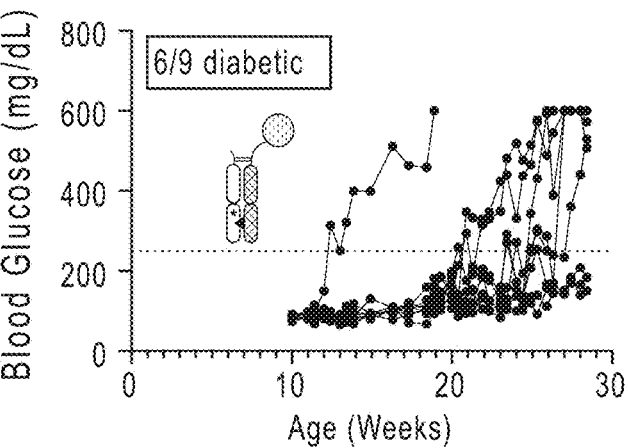
Figure 8E:
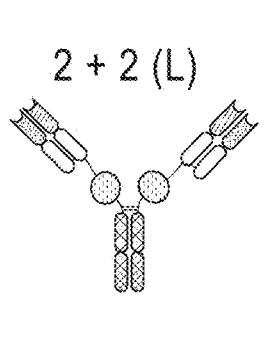
Figure 8E:
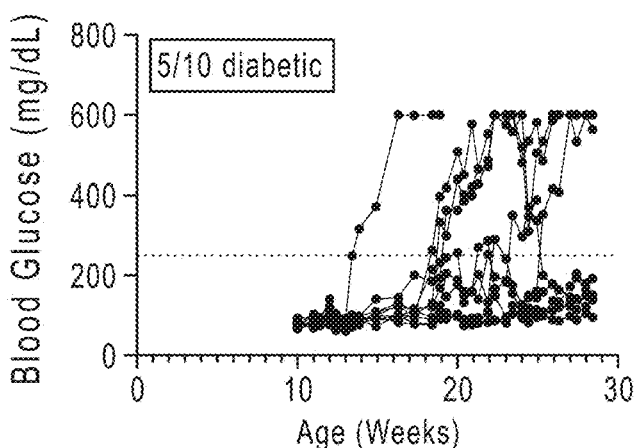
Figure 8F:
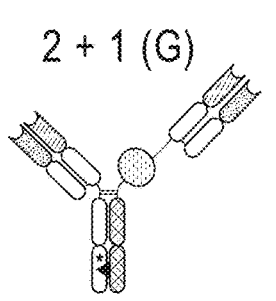
Figure 8F:
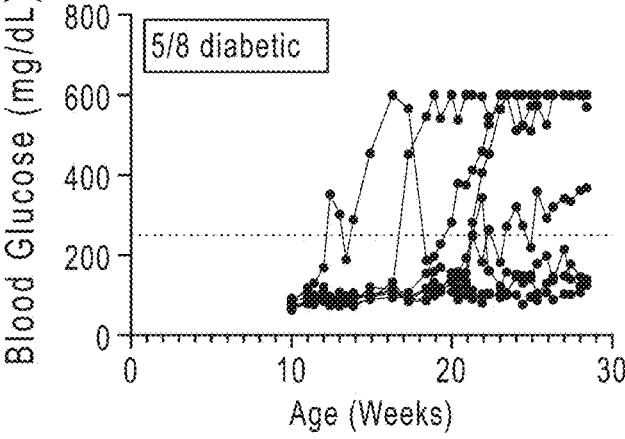
Figure 8G:
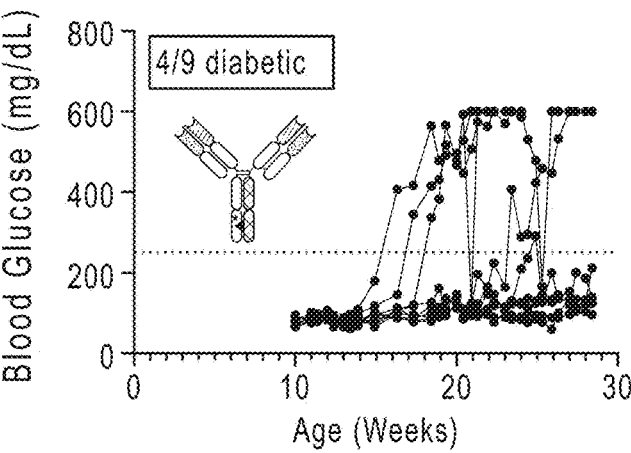
Figure 8H:
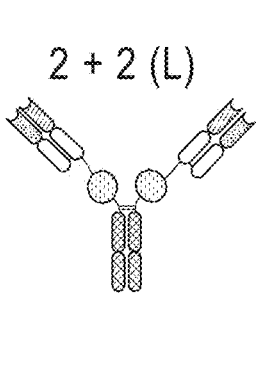
Figure 8H:
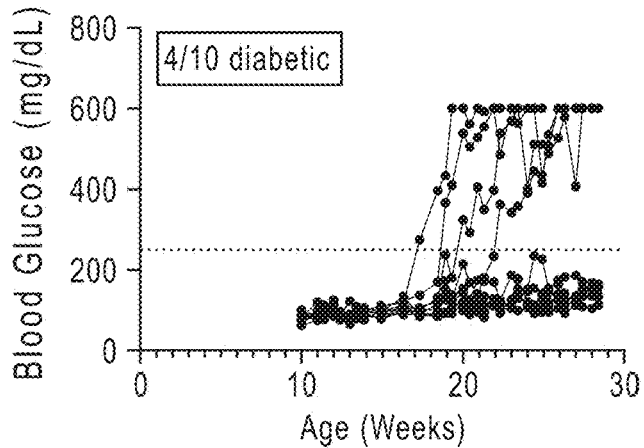
Figure 8I:
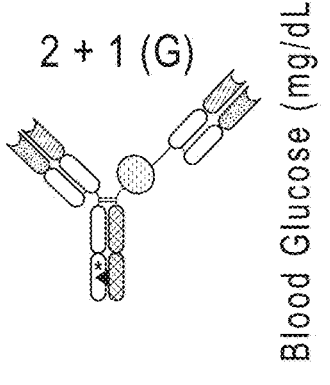
Figure 8I:
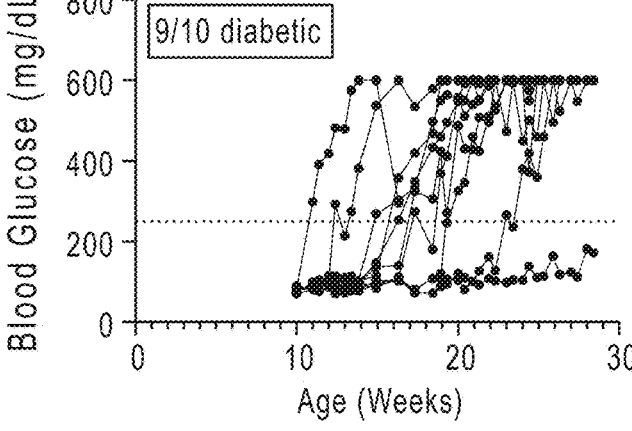

Results from the luciferase assay are depicted in FIG. 6 and Table 6. Nineteen molecules of the present disclosure were tested for PD1 agonism and regulation of T-cell signaling thereof using HEK293/CD22/mCD20 and Jurkat/AP1-luc/mPD1 reporter cells with CD3 bsAb. As shown in Table 6, four out of nineteen molecules of the present disclosure showed inhibition of T cell signaling with IC50 ecules including cell-based flow binding and in vitro bioassay results. Results from the luciferase assay are depicted in FIGS. 6A-6E. Molecules 2+2 m20_mPL_4 and 2+1 m20_mPL_3 (G and L, respectively, in Table 6) exhibited strongest PD1 agonism. 2+2 m20_mPL_4 revealed strongest binding to mPD1 and mCD20 by cell-based flow analysis, however 2+1 m20_mPL_3 revealed only moderate binding to mPD1-expressing cells, suggesting clustering of mPD1 via bivalent binding of mCD20 in the presence of both APC and effector cells is required. Overall, similar cell-binding affinity (mPD1 or mCD20) did not translate into similar PD1 agonism, for example F vs. G and K vs. L (FIG. 6A and Table 6), indicating both valency and structural arrangement of CD20 and mPDL1 ectodomain arms are important to confer the activity.

TABLE 6

| | | Cell Based Flow Binding | | | | | | Bioassay | | | |
| | | MC38/mCD20 | | HEK293/mCD20 | | Jurkat/mPD1 | | 2.5 nM CD3 bsAb (EC50 = 6.27E−10 M) | | 1nM CD3 bsAb (EC50 = 1.15E−09 M) | |
| Number ID | Molecule | EC50 (M) | Max MFI | EC50 (M) | Max MFI | EC50 (M) | Max MFI | IC50 (M) | Max % inhibition | IC50 (M) | Max % inhibition |
|---|---|---|---|---|---|---|---|---|---|---|---|
| A | m20_mPL_1 | 6.25E−07 | 16791 | NT | NT | ND | 8154 | WB/NB | 18 | NT | NT |
| B | m20_mPL_2 | 5.47E−07 | 5570 | NT | NT | ND | 9949 | WB/NB | 29 | NT | NT |
| C | m20_mPL_3 | ND | 7505 | NT | NT | ND | 2611 | WB/NB | 17 | NT | NT |
| D | m20_mPL_4 | NT | NT | ND | 10382 | ND | 1757 | NT | NT | >100 nM | 40 |
| E | 2 + 1 m20_mPL_1 | 6.40E−09 | 39112 | NT | NT | 1.24E−07 | 13369 | WB/NB | 16 | NT | NT |
| F | 2 + 1 m20_mPL_2 | 3.52E−09 | 42719 | NT | NT | ND | 1192 | WB/NB | 10 | NT | NT |
| G | 2 + 1 m20_mPL_3 | 3.93E−09 | 52855 | 1.50E−08 | 28862 | ND | 5629 | 3.16E−10 | 74 | 7.70E−10 | 80 |
| H | 1 + 2 m20_mPL_1 | ND | 20343 | NT | NT | 2.24E−08 | 16700 | WB/NB | 11 | NT | NT |
| I | 2 + 2 m20_mPL_1 | 1.81E−08 | 31023 | NT | NT | 2.95E−09 | 11598 | 1.92E−10 | 27 | NT | NT |
| J | 2 + 2 m20_mPL_2 | 3.45E−09 | 37275 | NT | NT | 1.51E−08 | 8505 | WB/NB | 8 | NT | NT |
| K | 2 + 2 m20_mPL_3 | 8.42E−09 | 35294 | NT | NT | 6.31E−09 | 6982 | 6.50E−11 | 33 | NT | NT |
| L | 2 + 2 m20_mPL_4 | NT | NT | 1.13E−08 | 30334 | ND | 18890 | NT | NT | 1.91E−10 | 84 |
| M | 1B12IgG1EN | 1.71E−09 | 41989 | 1.35E−08 | 28240 | NB | 118 | WB/NB | 0 | WB/NB | 19 |
| N | 1xNmPDL1Fc | NB | 129 | NB | 13.4 | ND | 3403 | WB/NB | 12 | WB/NB | 13 |
| O | 1xCmPDL1Fc | NB | 84.7 | NT | NT | ND | 1196 | WB/NB | −2 | NT | NT |
| P | NTdm_mPDL1Fc | NB | 167 | NT | NT | ND | 7895 | WB/NB | −7 | NT | NT |
| Q | 2xNmPDL1Fc | NB | 112 | NB | 12 | 4.70E−08 | 11577 | WB/NB | 2 | WB/NB | 12 |
| R | 2xCmPDL1Fc | NB | 85.7 | NT | NT | ND | 4639 | WB/NB | 8 | NT | NT |
| S | 2xFlxPDL1Fc | NB | 91.4 | NT | NT | 9.43E−09 | 6819 | WB/NB | −10 | NT | NT |
| | 18B12-scFvFc | 1.80E−08 | 48302 | NT | NT | NB | 198 | NT | NT | NT | NT |
| | Single arm mPDL1 WT-Fc | NB | 94.9 | NT | NT | ND | 495 | NT | NT | NT | NT |
| | REGN1932 (hIgG1 control) | NB | 140 | NB | 14.3 | NB | 90.4 | WB/NB | 3 | NT | NT |

WB/NB: Weak or no blocking
NB: No binding
ND: Not determined
NT: Not Tested values ranging 65-770 pM with maximum inhibition ranging 27-84%. Molecules 2+2 m20_MPL_4 and 2+1 m20_MPL_3 (G and L, respectively; Table 6) exhibited strongest PD1 agonism with maximum inhibition of 74% to 84% (FIGS. 6C and 6E). Fifteen out of 19 molecules showed weak or no inhibition with maximum inhibition ranging from −10 to 40%. An isoform control antibody did not show inhibition of signaling. CD3 bsAb showed activation of T cell signaling with EC50 values of 627 pM and 1.15 nM.

7.5. Example 4: Data Summary for In Vitro Assays with Anti-mCD20×mPDL1 Ectodomain Molecules Table 6 provides a summary of the in vitro data collected with the various anti-mCD20×mPDL1 ectodomain mol-

7.6. Example 5: In Vivo Efficacy of Anti-mCD20×mPDL1 Ectodomain Molecules

The ability of selected 2+2 and 2+1 anti-mCD20×mPDL1 ectodomain molecules to prevent the onset of type 1 diabetes (T1D) was assessed in pre-diabetic NOD mice. The experimental design is depicted in FIG. 7 and described in Section 7.1.7.

7.6.1. Results

Individual animal data are shown in FIGS. 8A-8I. FIGS. 9A and 9B depict the percent of diabetes-free mice at each indicated timepoint. Normally, 80-90% of NOD mice develop diabetes around age 25 weeks. In this experiment, however, only about 30% of mice developed diabetes by 27 weeks. While there was a lower diabetes incidence in control NOD mice, there was a clear trend of protection with higher doses of the (2+2) anti-mCD20×mPDL1 ectodomain molecule, 2+2 m20_mPL_4 (molecule L in FIG. 2A) but not with the (2+1 anti-mCD20×mPDL1 ectodomain molecule, 2+1 m20_mPL_3 (molecule G in FIG. 2A) (FIGS. 9A and 9B).

7.7. Example 6: Anti-mCD20×mPDL1 Ectodomain Molecule-Induced Reduction of Autoimmune T-Cell Infiltration Infiltration of T-cells has been linked to the development of autoimmune diseases, such as multiple sclerosis (Kaskow and Baecher-Allan, 2018. Cold Spring Harb Perspect Med. 8(4): a029025) and the autoimmune models of diabetes (Bettini and Vignali, 2011. Curr Opinion in Immunology, 23(6):754-760). The protective role of the (2+2) anti-mCD20×mPDL1 ectodomain molecule, 2+2 m20_mPL_4, against T-cell infiltration was assessed via flow cytometry as described in Section 7.1.2.

7.7.1. Results

In one assessment, populations of proliferating (activated) and less-activated islet specific CD8+ T cells were analyzed in of NOD mice described in Section 7.1.7 that were dosed with 0.1 or 1 mg/kg 2+2 m20_mPL_4 or a control molecule. Treatment with 1 mg/kg 2+2 m20_mPL_4 was associated with a marked percent increase of the less activated cluster of CD8+ T cells (FIG. 10A). Although the percentage of proliferating cluster of cells did not differ across the conditions (FIG. 10B), the ratio of less activated and proliferating cluster of cells was higher in pancreas tissues isolated from NOD mice treated with 1 mg/kg of 2+2 m20_mPL_4 (FIG. 10C), indicating that this treatment was able to reduce pancreatic infiltration of activated autoimmune T cells.

In another assessment, spinal cord infiltration of T cells was evaluated in a mouse model of multiple sclerosis described in Section 7.1.8. In spinal cords of mice treated with 1 mg/kg of 2+2 m20_mPL_4, there were substantially fewer CD3+ (FIG. 11A), CD4+ (FIG. 11B), and CD8+ (FIG. 11C) T cells, relative to spinal cords of mice that received control treatments at the same dosage. Hence, treatment with 2+2 m20_mPL_4 was able to reduce spinal cord infiltration of T-cells in a multiple sclerosis model.

8. SPECIFIC EMBODIMENTS, CITATION OF REFERENCES

While various specific embodiments have been illustrated and described, it will be appreciated that various changes can be made without departing from the spirit and scope of the disclosure(s). The present disclosure is exemplified by the numbered embodiments set forth below.

1. A protein comprising
(a) at least one CD20 targeting moiety;
(b) at least one PD1 agonist moiety;
(c) at least one dimerization moiety; and
(d) optionally, one or more linker moieties separating one or more moieties in the protein,
optionally wherein:
    (i) moieties of the protein are arranged, from N- to C-terminus, in the order of CD20 targeting moiety—PD1 agonist moiety—dimerization moiety;

(ii) moieties of the protein are arranged, from N- to C-terminus, in the order of dimerization moiety—PD1 agonist moiety—CD20 targeting moiety;
    (iii) the CD20 targeting moiety is an anti-CD20 Fab, the PD1 agonist moiety is the ectodomain of PDL1 or a PD1-binding portion thereof, and the dimerization moiety is an Fc domain, and the light chain of the Fab is not fused to the ectodomain of PDL1 or a PD1-binding portion thereof;
    (iv) the CD20 targeting moiety is an anti-CD20 Fab, the PD1 agonist moiety is the ectodomain of PDL1 or a PD1-binding portion thereof, and the dimerization moiety is an Fc domain, and the PD1 agonist moiety is not N-terminal to a VH of the anti-CD20 Fab;
    (v) the CD20 targeting moiety is an anti-CD20 Fab, the PD1 agonist moiety is the ectodomain of PDL1 or a PD1-binding portion thereof, and the dimerization moiety is an Fc domain, and the PD1 agonist moiety is not C-terminal to the Fc domain;
    (vi) the CD20 targeting moiety is an anti-CD20 Fab, the PD1 agonist moiety is the ectodomain of PDL1 or a PD1-binding portion thereof, and the dimerization moiety is an Fc domain, and the protein is monovalent for the CD20 targeting moiety and/or the PD1 agonist moiety;
    (vii) the protein is asymmetrical;
    (viii) the protein comprises an Fc heterodimer; or
    (ix) any combination of two or more of the foregoing (i) through (viii).

2. The protein of embodiment 1, wherein the at least one CD20 targeting moiety is an antigen-binding fragment of an anti-CD20 antibody.

3. The protein of embodiment 2, wherein the antigen-binding fragment of the anti-CD20 antibody is in the form of a Fab, a Fv or an scFv.

4. The protein of embodiment 2 or embodiment 3, wherein the anti-CD20 antibody comprises:
(a) complementarity-determining regions ("CDRs") having CDR sequences of rituximab, ocrelizumab, obinutuzumab, ofatumumab, ibritumomab ituxetan, tositumomab, ublituximab, ocaratuzumab, TRU-015, or veltuzumab;
(b) all 6 CDR sequences of rituximab, ocrelizumab, obinutuzumab, ofatumumab, ibritumomab ituxetan, tositumomab, ublituximab, ocaratuzumab, TRU-015, or veltuzumab;
(c) at least the heavy chain CDR sequences (CDR-H1, CDR-H2, CDR-H3) of a rituximab, ocrelizumab, obinutuzumab, ofatumumab, ibritumomab ituxetan, tositumomab, ublituximab, ocaratuzumab, TRU-015, or veltuzumab and the light chain CDR sequences of a universal light chain;
(d) a VH comprising the amino acid sequence of the VH of rituximab, ocrelizumab, obinutuzumab, ofatumumab, ibritumomab ituxetan, tositumomab, ublituximab, ocaratuzumab, TRU-015, or veltuzumab and a VL comprising the amino acid sequence of the same antibody; or
(e) a VH comprising the amino acid sequence of the VH of rituximab, ocrelizumab, obinutuzumab, ofatumumab, ibritumomab ituxetan, tositumomab, ublituximab, ocaratuzumab, TRU-015, or veltuzumab and a VL comprising a universal light chain VL sequence.

5. The protein of embodiment 2 or embodiment 3, wherein the anti-CD20 antibody binds to:

(a) a topological domain of CD20;

(b) a transmembrane domain of CD20; or (c) a region of CD20 displayed extracellularly on a surface of a cell (e.g., a B cell).

6. The protein of embodiment 2 or embodiment 3, wherein the anti-CD20 antibody:

(a) is selected from rituximab, ocrelizumab, obinutuzumab, ofatumumab, ibritumomab ituxetan, tositumomab, ublituximab, ocaratuzumab, TRU-015, and veltuzumab (b) competes for binding to CD20 with and/or binds to the same epitope as an anti-CD20 antibody selected from rituximab, ocrelizumab, obinutuzumab, ofatumumab, ibritumomab ituxetan, tositumomab, ublituximab, ocaratuzumab, TRU-015, and veltuzumab.

7. The protein of any one of embodiments 1 to 6, wherein the at least one PD1 agonist moiety comprises an amino acid sequence having at least 90% sequence identity to a PD1-binding portion of the extracellular domain of PDL1, optionally wherein PDL1 is human or murine PDL1.

8. The protein of embodiment 7, wherein the PD1 agonist moiety comprises an amino acid sequence having at least 95% sequence identity to a PD1-binding portion of the extracellular domain of PDL1, optionally wherein PDL1 is human or murine PDL1.

9. The protein of embodiment 7, wherein the PD1 agonist moiety comprises an amino acid sequence having at least 97% sequence identity to a PD1-binding portion of the extracellular domain of PDL1, optionally wherein PDL1 is human or murine PDL1.

10. The protein of embodiment 7, wherein the PD1 agonist moiety comprises an amino acid sequence having at least 98% sequence identity to a PD1-binding portion of the extracellular domain of PDL1, optionally wherein PDL1 is human or murine PDL1.

11. The protein of embodiment 7, wherein the PD1 agonist moiety comprises an amino acid sequence having at least 99% sequence identity to a PD1-binding portion of the extracellular domain of PDL1, optionally wherein PDL1 is human or murine PDL1.

12. The protein of embodiment 7, wherein the PD1 agonist moiety comprises the amino acid sequence of a PD1-binding portion of the extracellular domain of PDL1, optionally wherein PDL1 is human or murine PDL1.

13. The protein of any one of embodiments 7 to 12, wherein the PD1-binding portion of the extracellular domain of PDL1 comprises amino acids 19-134 of human PDL1 or amino acids 19-134 of murine PDL1.

14. The protein of any one of embodiments 7 to 12, wherein the PD1-binding portion of the extracellular domain of PDL1 comprises or consists of the PDL1 ectodomain, optionally wherein PDL1 is human or murine PDL1.

15. The protein of any one of embodiments 1 to 6, wherein the at least one PD1 agonist moiety comprises an amino acid sequence having at least 90% sequence identity to a PD1-binding portion of the extracellular domain of PDL2, optionally wherein PDL2 is human or murine PDL2.

16. The protein of embodiment 15, wherein the PD1 agonist moiety comprises an amino acid sequence having at least 95% sequence identity to a PD1-binding portion of the extracellular domain of PDL2, optionally wherein PDL2 is human or murine PDL2.

17. The protein of embodiment 15, wherein the PD1 agonist moiety comprises an amino acid sequence having at least 97% sequence identity to a PD1-binding portion of the extracellular domain of PDL2, optionally wherein PDL2 is human or murine PDL2.

18. The protein of embodiment 15, wherein the PD1 agonist moiety comprises an amino acid sequence having at least 98% sequence identity to a PD1-binding portion of the extracellular domain of PDL2, optionally wherein PDL1 is human or murine PDL2.

19. The protein of embodiment 15, wherein the PD1 agonist moiety comprises an amino acid sequence having at least 99% sequence identity to a PD1-binding portion of the extracellular domain of PDL2, optionally wherein PDL2 is human or murine PDL2.

20. The protein of embodiment 15, wherein the PD1 agonist moiety comprises the amino acid sequence of a PD1-binding portion of the extracellular domain of PDL2, optionally wherein PDL2 is human or murine PDL2.

21. The protein of any one of embodiments 15 to 20, wherein the PD1-binding portion of the extracellular domain of PDL2 comprises amino acids 20-121 of human PDL2 or amino acids 20-121 of murine PDL2.

22. The protein of any one of embodiments 15 to 20, wherein the PD1-binding portion of the extracellular domain of PDL2 comprises or consists of the PDL2 ectodomain, optionally wherein PDL2 is human or murine PDL2.

23. The protein of any one of embodiments 1 to 22, which comprises one or more linker moieties.

24. The protein of embodiment 23 wherein at least one CD20 targeting moiety and at least one PD1 agonist moiety are separated by a linker moiety.

25. The protein of embodiment 23 or embodiment 24 wherein at least one CD20 targeting moiety and at least at least one dimerization moiety are separated by a linker moiety.

26. The protein of any one of embodiments 23 to 25 wherein at least one PD1 agonist moiety and at least at least one dimerization moiety are separated by a linker moiety.

27. The protein of any one of embodiments 21 to 26, wherein each linker moiety is (a) at least 5 or at least 10 amino acids in length, (b) up to 20, up to 25 or up to 30 amino acids in length and/or (c) is 5-15 amino acids or 5-20 amino acids in length.

28. The protein of any one of embodiments 21 to 27, wherein at least one linker moiety comprises a glycine-serine linker.

29. The protein of embodiment 28, wherein the glycine-serine linker comprises the sequence GaS (SEQ ID NO: 14) or a multimer thereof.

30. The protein of embodiment 29, wherein the multimer comprises 2, 3, 4, 5, or more repeats of the amino acid sequence $G_4S$ (SEQ ID NO: 56).

31. The protein of any one of embodiments 1 to 30 which comprises a monomer according to Exemplary Monomer 1 and a monomer according to Exemplary Monomer 2.

32. The protein of embodiment 31, wherein Exemplary Monomer 1 comprises or consists of, in an N- to C-terminal orientation, a CD20 targeting moiety (e.g., anti-CD20 Fab, Fv or scFV), an optional linker moiety and a dimerization moiety.

33. The protein of embodiment 30, wherein Exemplary Monomer 1 is composed of a single polypeptide chain.

34. The protein of embodiment 30, wherein Exemplary Monomer 1 is composed of two polypeptide chains.

35. The protein of any one of embodiments 29 to 34, wherein Exemplary Monomer 2 comprises or consists of, in an N- to C-terminal orientation, a PD1 agonist moiety (e.g., a moiety comprising (i) the amino acid sequence of the extracellular domain of PDL1 or PDL2; (ii) a fragment of (i) which is capable of binding to PD1; or (iii) an amino acid sequence which has at least 90% sequence identity to (i) or (ii)), an optional linker moiety, and a dimerization moiety.

36. The protein of any one of embodiments 31 to 35, which has the configuration depicted in FIG. 1A.

37. The protein of any one of embodiments 1 to 30 which comprises a monomer according to Exemplary Monomer 3 and a monomer according to Exemplary Monomer 4.

38. The protein of embodiment 37, wherein Exemplary Monomer 3 comprises or consists of, in an N- to C-terminal orientation, an optional linker moiety and a dimerization moiety.

39. The protein of embodiment 37 or embodiment 38, wherein Exemplary Monomer 4 comprises or consists of, in an N- to C-terminal orientation, a PD1 agonist moiety (e.g., a moiety comprising (i) the amino acid sequence of the extracellular domain of PDL1 or PDL2; (ii) a fragment of (i) which is capable of binding to PD1; or (iii) an amino acid sequence which has at least 90% sequence identity to (i) or (ii)), an optional linker moiety, a CD20 targeting moiety (e.g., anti-CD20 Fab, Fv or scFV), an optional linker moiety and a dimerization moiety.

40. The protein of embodiment 39, wherein Exemplary Monomer 4 is composed of a single polypeptide chain.

41. The protein of embodiment 39, wherein Exemplary Monomer 4 is composed of two polypeptide chains.

42. The protein of any one of embodiments 37 to 39 which has the configuration depicted in FIG. 1B.

43. The protein of any one of embodiments 1 to 30 which comprises a monomer according to Exemplary Monomer 3 and a monomer according to Exemplary Monomer 5.

44. The protein of embodiment 43, wherein Exemplary Monomer 3 comprises or consists of, in an N- to C-terminal orientation, an optional linker moiety and a dimerization moiety.

45. The protein of embodiment 43 or embodiment 44, wherein Exemplary Monomer 5 comprises or consists of, in an N- to C-terminal orientation, a CD20 targeting moiety (e.g., anti-CD20 Fab, Fv or scFV), an optional linker moiety, a dimerization moiety, and a PD1 agonist moiety (e.g., a moiety comprising (i) the amino acid sequence of the extracellular domain of PDL1 or PDL2; (ii) a fragment of (i) which is capable of binding to PD1; or (iii) an amino acid sequence which has at least 90% sequence identity to (i) or (ii)).

46. The protein of embodiment 45, wherein Exemplary Monomer 5 is composed of a single polypeptide chain.

47. The protein of embodiment 45, wherein Exemplary Monomer 5 is composed of two polypeptide chains.

48. The protein of any one of embodiments 43 to 47, which has the configuration depicted in FIG. 1C.

49. The protein of any one of embodiments 1 to 30 which comprises a monomer according to Exemplary Monomer 3 and a monomer according to Exemplary Monomer 6.

50. The protein of embodiment 49, wherein Exemplary Monomer 3 comprises or consists of, in an N- to C-terminal orientation, an optional linker moiety and a dimerization moiety.

51. The protein of embodiment 49 or embodiment 50, wherein Exemplary Monomer 6 comprises or consists of, in an N- to C-terminal orientation, a CD20 targeting moiety (e.g., anti-CD20 Fab, Fv or scFV), an optional linker moiety, a PD1 agonist moiety (e.g., a moiety comprising (i) the amino acid sequence of the extracellular domain of PDL1 or PDL2; (ii) a fragment of (i) which is capable of binding to PD1; or (iii) an amino acid sequence which has at least 90% sequence identity to (i) or (ii)), an optional linker moiety and a dimerization moiety.

52. The protein of any one of embodiments 49 to 51, wherein Exemplary Monomer 6 is composed of a single polypeptide chain.

53. The protein of any one of embodiments 49 to 51, wherein Exemplary Monomer 6 is composed of two polypeptide chains.

54. The protein of any one of embodiments 49 to 53, which has the configuration depicted in FIG. 1D.

55. The protein of any one of embodiments 1 to 30 which comprises a monomer according to Exemplary Monomer 1 and a monomer according to Exemplary Monomer 4.

56. The protein of embodiment 55, wherein Exemplary Monomer 1 comprises or consists of, in an N- to C-terminal orientation, a CD20 targeting moiety (e.g., anti-CD20 Fab, Fv or scFV), an optional linker moiety and a dimerization moiety.

57. The protein of embodiment 56, wherein Exemplary Monomer 1 is composed of a single polypeptide chain.

58. The protein of embodiment 56, wherein Exemplary Monomer 1 is composed of two polypeptide chains.

59. The protein of any one of embodiments 55 to 58, wherein Exemplary Monomer 4 comprises or consists of, in an N- to C-terminal orientation, a PD1 agonist moiety (e.g., a moiety comprising (i) the amino acid sequence of the extracellular domain of PDL1 or PDL2; (ii) a fragment of (i) which is capable of binding to PD1; or (iii) an amino acid sequence which has at least 90% sequence identity to (i) or (ii)), an optional linker moiety, a CD20 targeting moiety (e.g., anti-CD20 Fab, Fv or scFV), an optional linker moiety and a dimerization moiety.

60. The protein of embodiment 59, wherein Exemplary Monomer 4 is composed of a single polypeptide chain.

61. The protein of embodiment 59, wherein Exemplary Monomer 4 is composed of two polypeptide chains.

62. The protein of any one of embodiments 55 to 61, which has the configuration depicted in FIG. 1E.

63. The protein of any one of embodiments 1 to 30 which comprises a monomer according to Exemplary Monomer 1 and a monomer according to Exemplary Monomer 5.

64. The protein of embodiment 63, wherein Exemplary Monomer 1 comprises or consists of, in an N- to C-terminal orientation, a CD20 targeting moiety (e.g., anti-CD20 Fab, Fv or scFV), an optional linker moiety and a dimerization moiety.

65. The protein of embodiment 64, wherein Exemplary Monomer 1 is composed of a single polypeptide chain.

66. The protein of embodiment 64, wherein Exemplary Monomer 1 is composed of two polypeptide chains.

67. The protein of any one of embodiments 63 to 66, wherein Exemplary Monomer 5 comprises or consists of, in an N- to C-terminal orientation, a CD20 targeting moiety (e.g., anti-CD20 Fab, Fv or scFV), an optional linker moiety, a dimerization moiety, and a PD1 agonist moiety (e.g., a moiety comprising (i) the amino acid sequence of the extracellular domain of PDL1 or PDL2; (ii) a fragment of (i) which is capable of binding to PD1; or (iii) an amino acid sequence which has at least 90% sequence identity to (i) or (ii)).

68. The protein of embodiment 67, wherein Exemplary Monomer 5 is composed of a single polypeptide chain.

69. The protein of embodiment 67, wherein Exemplary Monomer 5 is composed of two polypeptide chains.

70. The protein of any one of embodiments 63 to 69, which has the configuration depicted in FIG. 1F.

71. The protein of any one of embodiments 1 to 30 which comprises a monomer according to Exemplary Monomer 1 and a monomer according to Exemplary Monomer 6.

72. The protein of embodiment 71, wherein Exemplary Monomer 1 comprises or consists of, in an N- to C-terminal orientation, a CD20 targeting moiety (e.g., anti-CD20 Fab, Fv or scFV), an optional linker moiety and a dimerization moiety.

73. The protein of embodiment 72, wherein Exemplary Monomer 1 is composed of a single polypeptide chain.

74. The protein of embodiment 72, wherein Exemplary Monomer 1 is composed of two polypeptide chains.

75. The protein of any one of embodiments 71 to 74, wherein Exemplary Monomer 6 comprises or consists of, in an N- to C-terminal orientation, a CD20 targeting moiety (e.g., anti-CD20 Fab, Fv or scFV), an optional linker moiety, a PD1 agonist moiety (e.g., a moiety comprising (i) the amino acid sequence of the extracellular domain of PDL1 or PDL2; (ii) a fragment of (i) which is capable of binding to PD1; or (iii) an amino acid sequence which has at least 90% sequence identity to (i) or (ii)), an optional linker moiety and a dimerization moiety.

76. The protein of embodiment 75, wherein Exemplary Monomer 6 is composed of a single polypeptide chain.

77. The protein of embodiment 75, wherein Exemplary Monomer 6 is composed of two polypeptide chains.

78. The protein of any one of embodiments 71 to 77, which has the configuration depicted in FIG. 1G.

79. The protein of any one of embodiments 1 to 30 which comprises a monomer according to Exemplary Monomer 1 and a monomer according to Exemplary Monomer 7.

80. The protein of embodiment 79, wherein Exemplary Monomer 1 comprises or consists of, in an N- to C-terminal orientation, a CD20 targeting moiety (e.g., anti-CD20 Fab, Fv or scFV), an optional linker moiety and a dimerization moiety.

81. The protein of embodiment 80, wherein Exemplary Monomer 1 is composed of a single polypeptide chain.

82. The protein of embodiment 80, wherein Exemplary Monomer 1 is composed of two polypeptide chains.

83. The protein of any one of embodiments 79 to 82, wherein Exemplary Monomer 7 comprises or consists of, in an N- to C-terminal orientation, a PD1 agonist moiety (e.g., a moiety comprising (i) the amino acid sequence of the extracellular domain of PDL1 or PDL2; (ii) a fragment of (i) which is capable of binding to PD1; or (iii) an amino acid sequence which has at least 90% sequence identity to (i) or (ii)), an optional linker moiety, a PD1 agonist moiety (e.g., a moiety comprising (i) the amino acid sequence of the extracellular domain of PDL1 or PDL2; (ii) a fragment of (i) which is capable of binding to PD1; or (iii) an amino acid sequence which has at least 90% sequence identity to (i) or (ii)), an optional linker moiety and a dimerization moiety.

84. The protein of any one of embodiments 79 to 83, which has the configuration depicted in FIG. 1H.

85. The protein of any one of embodiments 1 to 30 which comprises two monomers according to Exemplary Monomer 4.

86. The protein of embodiment 85, wherein each Exemplary Monomer 4 comprises or consists of, in an N- to C-terminal orientation, a PD1 agonist moiety (e.g., a moiety comprising (i) the amino acid sequence of the extracellular domain of PDL1 or PDL2; (ii) a fragment of (i) which is capable of binding to PD1; or (iii) an amino acid sequence which has at least 90% sequence identity to (i) or (ii)), an optional linker moiety, a CD20 targeting moiety (e.g., anti-CD20 Fab, Fv or scFV), an optional linker moiety and a dimerization moiety.

87. The protein of embodiment 86, wherein each Exemplary Monomer 4 is composed of a single polypeptide chain.

88. The protein of embodiment 86, wherein each Exemplary Monomer 4 is composed of two polypeptide chains.

89. The protein of any one of embodiments 85 to 88, which has the configuration depicted in FIG. 1I.

90. The protein of any one of embodiments 1 to 30 which comprises two monomers according to Exemplary Monomer 5.

91. The protein of embodiment 90, wherein each Exemplary Monomer 5 comprises or consists of, in an N- to C-terminal orientation, a CD20 targeting moiety (e.g., anti-CD20 Fab, Fv or scFV), an optional linker moiety, a dimerization moiety, and a PD1 agonist moiety (e.g., a moiety comprising (i) the amino acid sequence of the extracellular domain of PDL1 or PDL2; (ii) a fragment of (i) which is capable of binding to PD1; or (iii) an amino acid sequence which has at least 90% sequence identity to (i) or (ii)).

92. The protein of embodiment 91, wherein each Exemplary Monomer 5 is composed of a single polypeptide chain.

93. The protein of embodiment 91, wherein each Exemplary Monomer 5 is composed of two polypeptide chains.

94. The protein of any one of embodiments 90 to 93, which has the configuration depicted in FIG. 1J.

95. The protein of any one of embodiments 1 to 30 which comprises a monomer according to Exemplary Monomer 8 and a monomer according to Exemplary Monomer 9.

96. The protein of embodiment 95, wherein Exemplary Monomer 8 comprises or consists of, in an N- to C-terminal orientation, a CD20 targeting moiety (e.g., anti-CD20 Fab, Fv or scFV), an optional linker moiety, a dimerization moiety, an optional linker moiety, and a CD20 targeting moiety (e.g., anti-CD20 Fab, Fv or scFV).

97. The protein of embodiment 96, wherein each Exemplary Monomer 8 is composed of a single polypeptide chain.

98. The protein of embodiment 96, wherein each Exemplary Monomer 8 is composed of two polypeptide chains.

99. The protein of embodiment 96, wherein each Exemplary Monomer 8 is composed of three polypeptide chains.

100. The protein of any one of embodiments 95 to 99, wherein Exemplary Monomer 9 comprises or consists of, in an N- to C-terminal orientation, a PD1 agonist moiety (e.g., a moiety comprising (i) the amino acid sequence of the extracellular domain of PDL1 or PDL2; (ii) a fragment of (i) which is capable of binding to PD1; or (iii) an amino acid sequence which has at least 90% sequence identity to (i) or (ii)), an optional linker moiety, a dimerization moiety, an optional linker moiety, a PD1 agonist moiety (e.g., a moiety comprising (i) the amino acid sequence of the extracellular domain of PDL1 or PDL2; (ii) a fragment of (i) which is capable of binding to PD1; or (iii) an amino acid sequence which has at least 90% sequence identity to (i) or (ii)).

101. The protein of any one of embodiments 95 to 100, which has the configuration depicted in FIG. 1K.

102. The protein of any one of embodiments 1 to 30 which comprises two monomers according to Exemplary Monomer 6.

103. The protein of embodiment 102, wherein each Exemplary Monomer 6 comprises or consists of, in an N- to C-terminal orientation, a CD20 targeting moiety (e.g., anti-CD20 Fab, Fv or scFV), an optional linker moiety, a PD1 agonist moiety (e.g., a moiety comprising (i) the amino acid sequence of the extracellular domain of PDL1 or PDL2; (ii)

a fragment of (i) which is capable of binding to PD1; or (iii) an amino acid sequence which has at least 90% sequence identity to (i) or (ii)), an optional linker moiety and a dimerization moiety.

104. The protein of embodiment 103, wherein each Exemplary Monomer 6 is composed of a single polypeptide chain.

105. The protein of embodiment 103, wherein each Exemplary Monomer 6 is composed of two polypeptide chains.

106. The protein of any one of embodiments 102 to 104, which has the configuration depicted in FIG. 1L.

107. The protein of any one of embodiments 1 to 54 and 79 to 84, which comprises one CD20 targeting moiety.

108. The protein of embodiment 107, which comprises one PD1 agonist moiety.

109. The protein of embodiment 108, which has the configuration depicted in FIG. 1A.

110. The protein of embodiment 108, which has the configuration depicted in FIG. 1B.

111. The protein of embodiment 108, which has the configuration depicted in FIG. 1C.

112. The protein of embodiment 108, which has the configuration depicted in FIG. 1D.

113. The protein of embodiment 107, which comprises two PD1 agonist moieties.

114. The protein of embodiment 113, wherein the two PD1 agonist moieties are identical.

115. The protein of embodiment 113 or embodiment 114, which has the configuration depicted in FIG. 1H.

116. The protein of any one of embodiments 1 to 106, which comprises two CD20 targeting moieties.

117. The protein of embodiment 116, wherein the two CD20 targeting moieties are identical.

118. The protein of embodiment 116 or embodiment 117, which comprises one PD1 agonist moiety.

119. The protein of embodiment 118, which has the configuration depicted in FIG. 1E.

120. The protein of embodiment 118, which has the configuration depicted in FIG. 1F.

121. The protein of embodiment 118, which has the configuration depicted in FIG. 1G.

122. The protein of embodiment 116 or embodiment 117, which comprises two PD1 agonist moieties.

123. The protein of embodiment 122, wherein the two PD1 agonist moieties are identical.

124. The protein of embodiment 122 or embodiment 123, which has the configuration depicted in FIG. 1I.

125. The protein of embodiment 122 or embodiment 123, which has the configuration depicted in FIG. 1J.

126. The protein of embodiment 122 or embodiment 123, which has the configuration depicted in FIG. 1K.

127. The protein of embodiment 122 or embodiment 123, which has the configuration depicted in FIG. 1L.

128. The molecule of any one of embodiments 1 to 127 wherein the CD20 targeting moiety binds to an extracellular domain of human CD20.

129. The molecule of any one of embodiments 1 to 128 wherein the PD1 agonist moiety agonizes human PD1.

130. The molecule of any one of embodiments 1 to 127 wherein the CD20 targeting moiety binds to an extracellular domain of murine CD20.

131. The molecule of any one of embodiments 1 to 127 and 130 wherein the PD1 agonist moiety agonizes murine PD1.

132. The protein of any one of embodiments 1 to 131, wherein the at least one dimerization moiety is or comprises an Fc domain.

133. The protein of embodiment 132, wherein the Fc domain is a human Fc domain.

134. The protein of embodiment 132 or embodiment 133, wherein the Fc domain is an IgG1, IgG2, IgG3, or IgG4 Fc domain.

135. The protein of any one of embodiments 132 to 134, wherein the Fc domain has reduced effector function.

136. The protein of any one of embodiments 132 to 135, wherein the Fc domain is an IgG4 Fc domain.

137. The protein of any one of embodiments 132 to 136, wherein the Fc domain comprises the amino acid sequence

```
                                        (SEQ ID NO: 32)
ESKYGPPCPPCPAPPVAGPSVFLFPPKPKDTLMISRTPEVTCVVVDVSQ

EDPEVQFNWYVDGVEVHNAKTKPREEQFNSTYRVVSVLTVLHQDWLNGK

EYKCKVSNKGLPSSIEKTISKAKGQPREPQVYTLPPSQEEMTKNQVSLT

CLVKGFYPSDIAVEWESNGQPENNYKTTPPVLDSDGSFFLYSRLTVDKS

RWQEGNVFSCSVMHEALHNHYTQKSLSLSLGK or a portion thereof.
```

138. The protein of any one of embodiments 132 to 137, which comprises an Fc dimer.

139. The protein of embodiment 138, wherein the Fc dimer is an Fc homodimer.

140. The protein of embodiment 138, wherein the Fc dimer is an Fc heterodimer.

141. The protein of embodiment 140, wherein the Fc heterodimer comprises knob-in-hole mutations.

142. The protein of embodiment 140 or embodiment 141, wherein the Fc heterodimer comprises star mutations.

143. The protein of embodiment 1, wherein moieties of the protein are arranged, from N- to C-terminus, in the order of CD20 targeting moiety—PD1 agonist moiety—dimerization moiety.

144. The protein of embodiment 1, wherein moieties of the protein are arranged, from N- to C-terminus, in the order of dimerization moiety—PD1 agonist moiety—CD20 targeting moiety.

145. The protein of embodiment 1, wherein the CD20 targeting moiety is an anti-CD20 Fab, the PD1 agonist moiety is the ectodomain of PDL1, and the dimerization moiety is an Fc domain, and the light chain of the Fab is not fused to the ectodomain of PDL1 or PD1-binding portion thereof.

146. The protein of embodiment 1, wherein the CD20 targeting moiety is an anti-CD20 Fab, the PD1 agonist moiety is the ectodomain of PDL1, and the dimerization moiety is an Fc domain, and the PD1 agonist moiety is not N-terminal to a VH of the anti-CD20 Fab.

147. The protein of embodiment 1, wherein the CD20 targeting moiety is an anti-CD20 Fab, the PD1 agonist moiety is the ectodomain of PDL1, and the dimerization moiety is an Fc domain, and the PD1 agonist moiety is not C-terminal to the Fc domain.

148. The protein of embodiment 1, wherein the CD20 targeting moiety is an anti-CD20 Fab, the PD1 agonist moiety is the ectodomain of PDL1, and the dimerization moiety is an Fc domain, and the protein is monovalent for the CD20 targeting moiety and/or the PD1 agonist moiety.

149. The protein of embodiment 1, wherein the protein is asymmetrical.

150. A nucleic acid or plurality of nucleic acids encoding the protein of any one of embodiments 1 to 149.

151. A host cell engineered to express protein of any one of embodiments 1 to 149 or the nucleic acid(s) of embodiment 150.

152. A method of producing the protein of any one of embodiments 1 to 149, comprising culturing the host cell of embodiment 151 and recovering the protein expressed thereby.

153. A pharmaceutical composition comprising the protein of any one of embodiments 1 to 149 and an excipient.

154. A method of treating a subject suffering from an immune disorder or condition associated with T cell dysregulation, comprising administering to the subject an effective amount of the protein of any one of embodiments 1 to 149 or the pharmaceutical composition of embodiment 153.

155. The method of embodiment 154, wherein the immune disorder or condition is type 1 diabetes, primary biliary cholangitis (PBC), Goodpasture's syndrome, amyloidosis, ankylosing spondylitis, anti-glomerular basement membrane nephritis, anti-tubular basement membrane nephritis, antiphospholipid syndrome, autoimmune hepatitis, autoimmune oophoritis, graft vs. host disease (GVHD), autoimmune pancreatitis, autoimmune retinopathy, Behcet's disease, Crohn's disease, Devic's disease, systemic lupus erythematosus (SLE), Dressler's syndrome, fibrosing alveolitis, glomerulonephritis, Graves' disease, Guillain-Barre syndrome, IgA Nephropathy, IgG4-related sclerosing disease, immune thrombocytopenic purpura (ITP), microscopic polyangiitis (MPA), mixed connective tissue disease (MCTD), multiple sclerosis, polyneuropathy, organomegaly, endocrinopathy, monoclonal syndrome (POEMS), polyarteritis nodosa, rheumatoid arthritis, Schmidt syndrome, scleritis, scleroderma, Sjögren's syndrome, sperm or testicular autoimmunity, stiff person syndrome (SPS), Takayasu's arteritis, temporal arteritis, giant cell arteritis, thrombocytopenic purpura (TTP), Tolosa-Hunt syndrome (THS), or vasculitis.

156. The method of embodiment 154, wherein the immune disorder or condition is type 1 diabetes.

157. The method of embodiment 156, wherein the type 1 diabetes is pediatric onset type 1 diabetes.

158. The method of embodiment 156, wherein the type 1 diabetes is adult onset type 1 diabetes.

159. The method of embodiment 156, wherein the subject is a pediatric patient.

160. The method of any one of embodiments 156 to 158, wherein the subject is an adult patient.

161. The method of embodiment 154, wherein the immune disorder or condition is systemic lupus erythematosus.

162. The method of embodiment 154, wherein the immune disorder or condition is Crohn's disease.

163. The method of embodiment 154, wherein the immune disorder or condition is graft vs. host disease (GVHD).

164. The method of any one of embodiments 154 to 163, wherein the protein of any one of embodiments 1 to 149 or the pharmaceutical composition of embodiment 153 is administered as a single dose.

165. The method of any one of embodiments 154 to 164, wherein the administration of the protein of any one of embodiments 1 to 149 or the pharmaceutical composition of embodiment 153 is not repeated.

166. The method of any one of embodiments 154 to 165, wherein the method represses a cellular immune response in the subject.

167. The method of embodiment 166, wherein the method represses the immune system of the subject.

168. The method of embodiment 167, wherein the method decreases T cell function in the subject.

169. The method of embodiment 167, wherein the method decreases B cell function in the subject.

170. The method of embodiment 167, wherein the method decreases T cell responsiveness in the subject.

171. A method of repressing a cellular autoimmune response in a subject comprising administering to the subject an effective amount of the protein of any one of embodiments 1 to 149 or the pharmaceutical composition of embodiment 153.

172. The method of embodiment 171, wherein the method decreases T cell function in the subject.

173. The method of embodiment 171, wherein the method decreases B cell function in the subject.

174. The method of embodiment 171, wherein the method decreases T cell responsiveness in the subject.

175. The method of any one of embodiments 154 to 174, further comprising administering to the subject an additional therapeutic agent.

176. The method of embodiment 175, wherein the additional therapeutic agent is or comprises an immunomodulatory agent, a cytostatic agent, an inhibitor of cell adhesion, a cytotoxic agent, an activator of cell apoptosis, or an agent that increases the sensitivity of cells to apoptotic inducers.

177. The method of embodiment 175, wherein the additional therapeutic agent is or comprises CAR-expressing cells.

178. The method of embodiment 177, wherein the CAR-expressing cells are CAR-expressing Treg cells.

179. A method of localized PD1 agonism comprising administering to a subject an effective amount of the protein of any one of embodiments 1 to 149 or the pharmaceutical composition of embodiment 153.

180. The method of embodiment 179, wherein administering the protein or pharmaceutical composition localizes PD1 agonism to B cells in the subject.

181. A method of locally modulating an immune response in a target tissue or cell that expresses CD20 comprising administering to a subject an effective amount of the protein of any one of embodiments 1 to 149 or the pharmaceutical composition of embodiment 153.

182. The method of embodiment 181, wherein administering the protein or pharmaceutical composition modulates an immune response in a B cell in the subject.

183. A method of characterizing the ability of a molecule type I to agonize PD1 comprising:

(a) culturing a cell type I that stably expresses CD3, stably expresses an AP1-luciferase reporter gene, and stably expresses PD1 together with a cell type II that stably expresses CD22 and stably expresses CD20;

(b) incubating the cultured cells of step a) in the presence or absence of the molecule type I and a molecule type II; and (c) after step b), measuring luciferase activity in the cultured cells, wherein the molecule type I is a multi-specific antigen-binding molecule comprising: i) a first binding specificity that binds to an ectodomain of CD20; and ii) a second binding specificity that binds to PD1, wherein the molecule type II is a multi-specific antigen-binding molecule comprising: i) a first binding specificity that binds to an ectodomain of CD3; and ii)

a second binding specificity that binds to an ectodo-main of CD22, and wherein the presence of the molecule type II causes an increase in luciferase activity and the presence of the molecule type I causes a reduction in the luciferase activity caused by the molecule type II and wherein the amount of reduction in luciferase activity is indicative of the ability of the molecule type I to agonize PD1.

184. The method of embodiment 183, wherein PD1 is mPD1.

185. The method of embodiment 183, wherein the cell type I is a Jurkat E6-1 cell.

186. The method of embodiment 183, wherein the cell type I is transduced to express the AP1-luciferase reporter gene.

187. The method of embodiment 183, wherein the cell type I is transduced to express the PD1 gene.

188. The method of embodiments 186 or 187, wherein the cell type I is transduced with a lentivirus.

189. The method of embodiment 183, wherein the CD20 is a mCD20.

190. The method of embodiment 183, wherein the cell type II is an HEK293 cell.

191. The method of embodiment 183, wherein the cell type II is transduced to express CD22.

192. The method of embodiment 183, wherein the cell type II is transduced to express the CD20 gene.

193. The method of embodiments 191 or 192, wherein the cell type II is transduced with a lentivirus.

194. The method of embodiment 183, wherein cells of the cell type II were seeded prior to cells of the cell type I.

195. The method of embodiment 183, wherein the cultured cells are incubated in in the presence of the molecule type II, in the presence of a control antibody molecule and in the absence of the molecule type I.

196. The method of embodiment 183, wherein the cultured cells are incubated in the presence of the molecule type I and the molecule type II.

197. The method of embodiment 183, wherein the molecule of type I comprises an ectodomain of PDL1.

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended

What is claimed is:

1. A protein comprising a first monomer and a second monomer, wherein:

(a) the first monomer comprises, in N- to C-terminal orientation:
   (i) a first anti-CD20 Fab;
   (ii) a first linker moiety;
   (iii) a first mature PDL1 ectodomain;
   (iv) a second linker moiety; and
   (v) a first Fc domain; and (b) the second monomer comprises, in N- to C-terminal orientation
   (i) a second anti-CD20 Fab;
   (ii) a third linker moiety; and
   (iii) a second Fc domain;

wherein the first linker moiety, the second linker moiety, and the third linker moiety are 5-30 amino acids in length.

2. The protein of claim 1, wherein the first mature PDL1 ectodomain comprises the amino acid sequence of amino acids 19-238 of SEQ ID NO:2.

3. The protein of claim 1, wherein the first linker moiety or the second linker moiety comprises a glycine-serine linker.

4. The protein of claim 1, which is monovalent for the first mature PDL1 ectodomain.

5. The protein of claim 1, wherein the first anti-CD20 Fab binds to an extracellular domain of human CD20.

6. The protein of claim 1, wherein the first anti-CD20 Fab binds to an extracellular domain of murine CD20.

7. The protein of claim 1, wherein the first mature PDL1 ectodomain agonizes murine PD1.

8. The protein of claim 1, wherein the first anti-CD20 Fab and the second anti-CD20 Fab are identical.

9. The protein of claim 1, wherein the first monomer comprises a first polypeptide chain and a second polypeptide chain and the second monomer comprises a third polypeptide chain and a fourth polypeptide chain, wherein:

(a) the first polypeptide chain comprises, in an N- to C-terminal orientation, the VH of the first anti-CD20 Fab, the CH1 domain of the first anti-CD20 Fab, the first linker moiety, the first mature PDL1 ectodomain, the second linker moiety, and the first Fc domain;

(b) the second polypeptide chain comprises, in an N- to C-terminal orientation, the VL of the first anti-CD20 Fab and the CL domain of the first anti-CD20 Fab;

(c) the third polypeptide chain comprises, in an N- to C-terminal orientation, the VH of the second anti-CD20 Fab, the CH1 domain of the second anti-CD20 Fab, the third linker moiety, and the second Fc domain; and (d) the fourth polypeptide chain comprises, in an N- to C-terminal orientation, the VL of the second anti-CD20 Fab and the CL domain of the second anti-CD20 Fab; wherein the protein is monovalent for the first mature PDL1 ectodomain.

10. The protein of claim 1, wherein the second monomer comprises, in an N- to C-terminal orientation, the second anti-CD20 Fab, the third linker moiety, a second mature PDL1 ectodomain, a fourth linker moiety, and the second Fc domain; wherein the fourth linker moiety is 5-30 amino acids in length.

11. The protein of claim 10, wherein the first mature PDL1 ectodomain and the second mature PDL1 ectodomain are identical.

12. The protein of claim 10, wherein the first monomer comprises a first polypeptide chain and a second polypeptide chain and the second monomer comprises a third polypeptide chain and a fourth polypeptide chain, wherein:

(a) the first polypeptide chain comprises, in an N- to C-terminal orientation, the VH of the first anti-CD20 Fab, the CH1 domain of the first anti-CD20 Fab, the first linker moiety, the first mature PDL1 ectodomain, the second linker moiety, and the first Fc domain;

(b) the second polypeptide chain comprises, in an N- to C-terminal orientation, the VL of the first anti-CD20 Fab and the CL domain of the first anti-CD20 Fab;

(c) the third polypeptide chain comprises, in an N- to C-terminal orientation, the VH of the second anti-CD20 Fab, the CH1 domain of the second anti-CD20 Fab, the third linker moiety, the second mature PDL1 ectodomain, the fourth linker moiety, and the second Fc domain; and (d) the fourth polypeptide chain comprises, in an N- to C-terminal orientation, the VL of the second anti-CD20 Fab and the CL domain of the second anti-CD20 Fab.

13. The protein of claim 12, wherein the first anti-CD20 Fab and the second anti-CD20 Fab are identical.

14. A nucleic acid or plurality of nucleic acids encoding the protein of claim 1.

15. A host cell engineered to express the protein of claim 1.

16. A method of producing a protein comprising culturing the host cell of claim 15 and recovering the protein expressed thereby.

17. A pharmaceutical composition comprising the protein of claim 1 and an excipient.

18. A method of treating a subject suffering from an immune disorder or condition associated with T cell dysregulation, comprising administering to the subject an effective amount of the protein of claim 1.

19. The method of claim 18, wherein the immune disorder or condition is type 1 diabetes.

20. A method of repressing a cellular autoimmune response in a subject comprising administering to the subject an effective amount of the protein of claim 1.

* * * * *